(12) United States Patent
Akiyama et al.

(10) Patent No.: US 7,358,348 B2
(45) Date of Patent: Apr. 15, 2008

(54) β-CATENIN NUCLEAR LOCALIZED PROTEIN

(75) Inventors: Tetsu Akiyama, Tokyo (JP); Shungo Adachi, Tokyo (JP)

(73) Assignee: Kyowa Hakko Kogyo Co., Ltd., Tokyo (JP)

( * ) Notice: Subject to any disclaimer, the term of this patent is extended or adjusted under 35 U.S.C. 154(b) by 552 days.

(21) Appl. No.: 10/381,247

(22) PCT Filed: Sep. 19, 2001

(86) PCT No.: PCT/JP01/08140

§ 371 (c)(1),
(2), (4) Date: Jul. 28, 2003

(87) PCT Pub. No.: WO02/24738

PCT Pub. Date: Mar. 28, 2002

(65) Prior Publication Data

US 2004/0073001 A1    Apr. 15, 2004

(30) Foreign Application Priority Data

Sep. 22, 2000    (JP) ............................. 2000-287876

(51) Int. Cl.
C07H 21/02    (2006.01)
(52) U.S. Cl. .................................... 536/23.1
(58) Field of Classification Search ................ 536/23.1
See application file for complete search history.

(56) References Cited

U.S. PATENT DOCUMENTS 5,658,784 A * 8/1997 Eckner et al. .............. 435/325
2002/0086986 A1* 7/2002 Basler et al. ............... 536/23.2

FOREIGN PATENT DOCUMENTS

| WO | WO 00/58473 A2 | 10/2000 |
| WO | WO 01/75067 A2 | 10/2001 |
| WO | WO 01/75067 A3 | 10/2001 |
| WO | WO 01/92523 A2 | 12/2001 |
| WO | WO 01/92523 A3 | 12/2001 |

OTHER PUBLICATIONS

Simcha et al (The Journal of Cell Biology, Mar. 1998, 6(15): 1433-1448).*
Tockman et al (Cancer Res., 1992, 52:2711s-2718s).*
Gura (Science, 1997, 278:1041-1042.).*
Hecht et al (The EMBO Journal, Apr. 17, 2000, 19(9): 1839-1850).*
Prieve et al., "Nuclear Localization and Formation of β-Catenin-Lymphoid Enhancer Factor 1 Complexes Are Not Sufficient for Activation of Gene Expression", *Mol. Cell Biol.* 19(6): 4503-4515 (1999).
Ertl et al., "The Extracellular Matrix of *Volvox carteri*: Molecular Structure of the Cellular Compartment",*J. Cell Biol.* 109(6): 3493-3501 (1989).
Godl et al., "Differential targeting of closely related ECM glycoproteins: the pherophorin family from *Volvox*", *Embo Journal* 16(1): 25-34 (1997).
Tago et al., "Inhibition of Wnt signaling by ICAT, a novel β-catenin-interacting protein", *Genes and Development*, 14(14): 1741-1749 (2000).
Willis et al., Molecular Cloning of Translocation t(1;14)(q21;q32) Defines a Novel Gene (*BCL9*) at Chromosome 1q21, *Blood* 91(6): 1873-1881 (1998).

* cited by examiner

*Primary Examiner*—Misook Yu
*Assistant Examiner*—Sean E Aeder
(74) *Attorney, Agent, or Firm*—Townsend and Townsend and Crew LLP

(57) ABSTRACT

The present invention provides a novel β-catenin nuclear localizing protein and DNA encoding the protein. Furthermore, the use of the β-catenin nuclear localizing protein and the DNA encoding the protein provides a diagnostic agent and therapeutic agent for diseases such as cancer which is related to nuclear localization of β-catenin.

6 Claims, 2 Drawing Sheets

FIG. 1

```
mouse B9L                                                      MRILANKTRLPH
human bcl9                                                     MHSSN 13 PRRREAP-GSPPLSPRGHC--------PPAPAKPM-HPE---NKLTNHGKTGNGGAQSQHQNVN
   6 *KV*SSPS*NTQSKSKQEVMVRTVMS*SGN*QLDS*FS*Q**Q*GSAS***--------

64 QGPT-CNLGSKGVGAGSHGAKANQISPSNS-SLKNPQAGVSPFSSLKGKVKRERSVSVDS
  61 ---*SP*D---**----S*G*TP**LP-G*GG*MG*G-----NGA*G**I*A**

122 GEQREAGTPSLDSEAKEVAPRSKRRCVLERKQPYSGDEWCSGPDSEEDDKPIAAAHNCNV
 108 FDDP*NDDI-----------------------------------------**S

182 AD-----------PAMVTPQLGPGQTAQLPLSESSAPGPQHGPQPGLRPDVPGGGGGGVPG
 128 **HIKSQDSQHT*HSM**S-------N*TA*R*ST------*S**QTTATE*--------T*A

232 -KPPSQFVYVFTTHLANTAAEAVLQGRAESILAYHQQNVPRAKLDQA------------
 170 Q*T*AKV*-**S*EMK****K*QV*T*VSF*I**ISNN*TERSTAPLNTQISALRN

278 -PKVPPTPEPLPLNTP---SAGTPQSQP-PPLPPPPPAPGSAPPALPPEGPPEDTSQDLAP
 230 D**PL*QQP*V*A*QDQN*SQNTRL***I*A*A*K*AAP*RP*DR*S*---GVENK*T*

334 NSVG---AASTGGGTGGTHPNTPTAATANNPLPPG-------GDPGSAPGSALLGEATPTGNG
 288 =***SP*S=*PLPPDGSTPNNR*VT*VSQ*SNSSSA**KAP*--------PP*VSS*

387 QRNLVGS---EGLSKEQLEHRERSLQTLRDIERLLLRSGETEPFLKGPPGGAGEGGPPAGA
 340 EPPTL*ENPD*Q************Q*M*FPD--*K**-*I-------QS*-

445 PSAAQPPPSAPPGGLKKYEEPLQSMISQTQSLG---GPPLEHEVPGHPQG----------GD
 389 --------*QN*GVLD*PQ**P*G*I*A*MA*S****KGP**RTDVGA*FG***HRDVPFSPDE

494 M-GQQMNMMMQRLGQDSL---TPEQVAWRKLQEEYYEEKRRKEEQIGLHGGRPLQDM-VG
 445 *VPPS**SQSGTI*P*H*DHM****I**LKL*Q*F*******P**VVVQQCS-****M*H

549 MGGMMG---RGPPPPYHSKPGDQCAPGMGAQLRGPMD---VQDPNQLRPGPPFPGPRFPGNQ
 504 QH*PR*VV********QMT*SEGW***-*TE----*FSDGINM*HS*P*RGMA*H*NM**S*

605 MQRVPGFGGMQSMPME---VPMNAMQRPVRPGMAWNEDLPPIGGPSNFAQNAVPYPG---
 560 *-*L**AINSEGPN-*PAS**GLS*VS*PD**V*K*PDGRP-------RGI

659 -GQGEAERFMTPR-VREELLRHQLLEKRSMGMQRPLGMAGSGMGQSMEMERMIQ-AHRQ
 612 FS*P*RG**FPN*QGLSMFQQA**Q-L*L---*P***ME*IRP**N*PGSQ*H

715 MDPA---MFPGQMTGGDGLAGTPMGIEFGGGRGLLSPPMGQSGLREVDPPMGPGN------
 669 *E*GNNPI**R--------IPV*-----*P***SR*DFP-KG*IP*Q****RELEFG

767 ---LNMNMNVNMNMNMNLNVQMTPQQQMLMSQKMRGPGDMMGPQGLSPEEMARVRAQNSS
 711 MVPSG*KGD**L*V**GS*SI------***------EA*AG****LKL*P-GG*

824 GMMGGPQKMLMPSQFPNGGQQGFSGGQGPYQAMPQDMG--------NTPDMFSPDQSSVPMG
 756 D*LPAQ***V-*LP*GEHP**EYGM*PR*FLP*S*GP*SNSGLR*LREP*IG***RT---

878 TVGTARLSHMP-LP---PASNPPGSVHLAS---NRGLGRRPSDLTISINQMGSPGMGHLKSP
 811 ---NS******P**LN*S***T-*LNT*PPVQ*****K*LD****GS*VH***INP****

933 TLSQVHSPLVTSPSANLKSPQTPSQMVPLPSTNPPGP-------LKSPQVLSSSLGVRSPTG
 867 *MHQMLG*G********LAGMLA------AAAASI*PG*A------AA

988 SPSRLKSPSMAVPSPGWVASPKTAMPSPGVSQNKQPPLSINSSSTLGNVEQGALPPSAPR
 917 VH*LPA*TS*PPLQ***IPP*HKA**TMA*PAM*****S*GP**PTAS

1048 NSSSA---PPANPSSGLMNPSLPFTSSPDPTPSQNPLSLMMSQMSKYAMPSSTPLYHNAIK
 977 QPA*VNI*GSL***--------T*Y*MP*EL**I*R*F*******D*

1106 TIATSDDELLPDR-PLLP------PPPPPQGSGPGISNNQPNQMHMNPAAAQ---SPMGMN
1031 *V*S***CSP*A*S*N**SMNNM*---------*M**NTGN*RI*SGPVVPMPTL**T

1157 LPGQQPLSHEPPPTMLPSPTPLGSNIPLHPNAQGTGGSSQNSMMMAPGGPDSLNAPCGPV
1084 -----*****S---NQM***NAV*P***P*GVPM*P*LM*H*PI*-----HG*QEP*M--*

1217 PSSSQMMSFP---PRLQQPHGAMAPTGAGGP-GLQQHYPSGMALP-------PEDLPT-
1131 *QGR---*G**QGF*PV*S*-PQQV*FPHN**S*G*GSF*G**GF*GEGPLGR*SN**QSS

1264 ------QPPGPIPPQQHLMGKGMTGRMGDAYPPGVLPGVASVLNDPELSEVIRPTPTGIP
1188 ADAALCK*G**GG*DSFTV-------L*NSM*-------FTD*Q***GA**

1318 EFDLSRIIPSEKPSSTLQYFPKSENQPPKAQP--PNLHLMNLQNMMAEQTPSRPPNLPGQ
1233 **********Q******RG*-V*GRK**QG*GPGFSHM*GGA*RMGLA***M

1376 QG---------VQRGLSMSMCHPGQMSLLGRTGVPP---QQGMVPHGLHQGVMSPPQGLMT
1292 G*PGPVGTPDIPL*TAP---HNPM*----RAFL**M---*P*HRM***A*ST*P

1425 QQNFMLM----------KQRGVGGEVYTQPPHMLSP                       1450
1343 G*P-T**SNPAAAVGMIPG*D**PA*-L**H*GPVG**GMMMSMQGMMGPNRTS     1394
```

β-CATENIN NUCLEAR LOCALIZED PROTEIN

TECHNICAL FIELD

The present invention relates to a novel protein that binds to β-catenin and localizes β-catenin into the nucleus, DNA encoding the protein, antibody recognizing the protein, therapeutic agent comprising the protein, DNA, or antibody., and diagnostic agent comprising the antibody.

BACKGROUND ART

The adenomatous polyposis coli (APC) gene is a gene isolated as a causative gene of familial adenomatous polyposis (FAP) (Kinzler, K. W. and Vogelstein, B., Cell 87: 159 (1996)). However, abnormality of the APC gene is not only reported in FAP but also in 70 to 80% of the cases of sporadic colon cancer. The onset of colon cancer is considered to be triggered by stepwise mutations of multiple genes including besides APC, such genes as K-ras, p53, and DCC. Since mutations in the APC gene are found in the earliest stage among these genes, it is considered that the abnormality of the APC gene ha's to be caused first in the onset of colon cancer.

In order to clarify the mechanism underlying carcinogenesis associated with the APC gene abnormality, it is necessary to determine the functions of the gene product, APC. APC, which is a protein about 300 kDa in size, has been reported to bind with β-catenin, glycogen synthase kinase-3β (GSK-3β), as well as DLG in cells (Rubinfeld, B. et al., Science 262: 1731 (1993); Su, L. K. et al., Science 262: 1734 (1993); Rubinfeld, B. et al., Science 272: 1023 (1996); Matsumine, A. et al., Science 272: 1020 (1996)). Regarding functions of the APC, it has been reported that the intracellular level of β-catenin is rapidly reduced when wild-type APC is expressed in colon cancer cell line SW480 having mutations in the APC gene (Munemitsu, S. et al., Proc. Natl. Acad. Sci. USA 92: 3046 (1995)). The central region containing a 7-repetitive sequence structure is essential for the function of APC and coincides with a region where mutations are found in many colon cancer cases. It has also been reported that the intracellular β-catenin level is elevated in these colon cancer cells (Munemitsu, S. et al., Proc. Natl. Acad. Sci. USA 92: 3046 (1995); Rubinfeld, B. et al., Cancer Res. 57: 4624 (1997)).

β-Catenin is also known as a membrane-skeletal protein for cell adhesion molecule cadherin and also reported to participate in the signal transduction of Wnt proteins described below (Cadigan, K. M. and Nusse, R., Genes Dev. 11: 3286 (1997)). The Wnt gene family is a large gene family which has a variety of functions in the processes of early embryogenesis and morphogenesis of animals; the family consists of about 20 types of genes in mouse and the genes are conserved among a variety of animals including African clawed frog (*Xenopus laevis*), fruit fly (*Drosophila melanogaster*), and nematoda (*Caenorhabditis elegans*). When Wnt binds to its receptor Frizzled, the activity of glycogen synthase kinase-3β (GSK-3β) is inhibited through an intracellular signaling molecule Dishevelled (Dsh) Since the phosphorylation of β-catenin mediated by GSK-3β causes the degradation of β-catenin, the inhibition of GSK-3β activity results in accumulation of β-catenin in cells. β-Catenin binds to a transcription factor (hereinafter abbreviated as TCF) belonging to the Lef/Tcf family to form a complex and thereby activates the TCF as a transcription factor. Thus, the accumulation of β-catenin results in the formation of the β-catenin/TCF complex, which translocates to the nucleus and thereby stimulates the transcription of target genes. Among Tcfs, Tcf-4 is specifically expressed in the epithelium of colon, and thus it is believed that β-catenin mainly forms a complex with Tcf-4 in colon cancer (Korinek, V. et al., Science 275: 1784 (1997)). In addition, it has been reported that there are some colon cancer cells and melanoma cells where the APC gene is wild-type but the β-catenin gene has mutation and is not regulated by GSK-3β (Morin, P. J. et al., Science 275: 1787 (1997); Rubinfeld, B. et al., Science 275: 1790 (1997)). It has been estimated that, β-catenin constantly accumulates in these cells, which results in transcriptional activation by the β-catenin/TCF complex.

Based on the above-described findings, β-catenin may be greatly involved in the onset of colon cancer. Therefore, a substance capable of inhibiting the function of β-catenin through the binding thereto may be associated with the onset of colon cancer and the like and may be useful for the treatment, diagnosis, and such thereof. As a molecule binding to β-catenin, a protein, Axin, has been reported which negatively regulates the signal transduction system of Wnt proteins (Zeng, L. et al., Cell 90: 181 (1997)). Axin binds to GSK-3β and thereby stimulates the phosphorylation of β-catenin (Ikeda, S. et al., EMBO J. 17: 1371 (1998)). Furthermore, it has been reported that Axin also binds to APC and β-catenin to stimulate the degradation of β-catenin and thereby reducing the level of β-catenin in cells (Kishida, S. et al., J. Biol. Chem. 273: 10823 (1998); Rubinfeld, B. et al., Current Biology 8: 573 (1998); Nakamura, T. et al., Genes Cells 3: 395 (1998)). However, no protein that binds to β-catenin and has the function to localize β-catenin into the nucleus is known.

The bc19 protein (Willis T. G. et al., Blood 91: 1871 (1998)) is a product of a gene that has been cloned from the translocation site of chromosome 1 in the CEMO-1 cell line, which was established from a patient with precursor B-cell acute lymphoblastic leukemia, and the expression level of the gene is abnormally high in CEMO-1 cells. However, its association with β-catenin, such as binding to β-catenin, remains unknown.

It is desired in the art to isolate and clarify the structure of proteins and DNA encoding the protein that are useful in the treatment and diagnosis of cancer by elucidating the mechanism of the onset of cancer (including colon cancer, wherein β-catenin plays a role) through the analysis of proteins that binds to β-catenin and regulate its function and genes encoding them.

DISCLOSURE OF THE INVENTION

An objective of the present invention is to provide a protein that binds to β-catenin and has the activity to localize β-catenin into the nucleus, DNA encoding the protein, antibody recognizing the protein, therapeutic agent comprising the protein or the DNA, and diagnostic agent comprising the antibody, all of which are useful for the treatment and diagnosis of cancer.

The present invention relates to:
(1) a protein comprising the amino acid sequence of amino acid residues 292 to 439 in the amino acid sequence represented by SEQ ID NO: 2;
(2) the protein according to above (1), wherein the protein comprises the amino acid sequence represented by SEQ ID NO: 2 or 4;
(3) a protein comprising the amino acid sequence represented by SEQ ID NO: 10;

(4) a protein comprising the amino acid sequence represented by SEQ ID NOs: 10 and 12;
(5) a protein consisting of the amino acid sequence, wherein one or more amino acids are added, deleted, or substituted in the amino acid sequence of the protein according. to any one of above (1) to (4), and said protein binding to β-catenin and having the activity to localize β-catenin into the nucleus;
(6) a protein consisting of the amino acid sequence having a homology of 60% or more to the amino acid sequence of the protein according to any one of above (1) to (4), and said protein binding to β-catenin and having the activity to localize β-catenin into the nucleus;
(7) the protein according to above (3) or (4), wherein the protein consists of the amino acid sequence having a homology of 60% or more to the amino acid sequence represented by SEQ ID NO: 2, and binds to β-catenin and has the activity to localize β-catenin into the nucleus;
(8) a protein comprising the amino acid sequence represented by SEQ ID NO: 12;
(9) a polypeptide comprising 5 to 60 continuous amino acid residues in the amino acid sequence of the protein according to any one of above (1) to (8);
(10) a DNA encoding the protein or the polypeptide of any one of above (1) to (9);
(11) a DNA comprising the nucleotide sequence of nucleotides 874 to 1317 in the nucleotide sequence represented by SEQ ID NO: 1;
(12) the DNA according to above (11),wherein the DNA comprises the nucleotide sequence represented by SEQ ID NO: 1 or 3;
(13) a DNA encoding a protein that binds to β-catenin and has the activity to localize β-catenin into the nucleus, and comprising the nucleotide sequence of the following [1] or [2]:
  [1] the nucleotide sequence represented by SEQ ID NO: 9; and
  [2] the nucleotide sequence represented by SEQ ID NOs: 9 and 11;
(14) a DNA hybridizing to the DNA of any one of above (10) to (13) under stringent conditions, which encodes a protein that binds to β-catenin and has the activity to localize β-catenin into the nucleus;
(15) a DNA comprising the nucleotide sequence represented by SEQ ID NOs: 9 and 11, and consisting of the nucleotide sequence having a homology of 60% or more to the nucleotide sequence of SEQ ID NO: 2, and encoding a protein that binds to β-catenin and has the activity to localize β-catenin into the nucleus;
(16) a DNA comprising the nucleotide sequence represented by SEQ ID NO: 11;
(17) a recombinant DNA obtainable by inserting the DNA according to any one of above (10) to (16) into a vector;
(18) a transformant obtainable by introducing the recombinant DNA according to above (17) into a host cell;
(19) a process for producing the protein or the polypeptide according to any one of above (1) to (9), which comprises the steps of:
  culturing the transformant of above (18) in a culture medium;
  producing and accumulating the protein or the polypeptide according to any one of above. (1) to (9) in the culture; and
  recovering the protein or the polypeptide from the culture;
(20) an oligonucleotide comprising 10 to 60 continuous nucleotides of the nucleotide sequence of the DNA according to any one of above (10) to (16) or a nucleotide sequence complementary thereto, or a derivative of the oligonucleotides;
(21) a method of detecting or quantifying, at the mRNA level, the expression level of the protein according to any one of above (3) to (7), using the DNA according to any one of above (10) to (16), or the oligonucleotide or derivative thereof according to above (20);
(22) a method of detecting a disease wherein the expression level of the protein according to any one of above (3) to (7) is increased or decreased in patient compared to normal healthy subject by measuring and comparing the expression level of the protein in normal healthy subject and test subject at the mRNA level by using the DNA according to any one of above (10) to (16), or the oligonucleotide or derivative thereof according to above (20);
(23) a diagnostic agent for a disease that exhibits increased or decreased expression level of the protein according to any one of above (3) to (7) in patient compared to normal healthy subject upon a measurment and comparison of the expression level of the protein at the mRNA level, wherein the diagnostic agent comprises the DNA according to any one of above (10) to (16), or the oligonucleotide or derivative thereof according to above (20);
(24) a method of detecting a mutation in a gene encoding the protein according to any one of above (3) to (7) using the DNA according to any one of above (10) to (16), or the oligonucleotide or derivative thereof according to above (20);
(25) a method of detecting a disease which has a mutation in a gene encoding the protein according to any one of above (3) to (7) using the DNA according to any one of above (10) to (16), or the oligonucleotide or derivative thereof according to above (20);
(26) a diagnostic agent for a disease which has a mutation in a gene encoding the protein according to any one of above (3) to (7), comprising the DNA according to any one of above (10) to (16) or the oligonucleotide or derivative thereof according to above (20);
(27) a method of inhibiting the expression of the protein according to any one of above (3) to (7) at the transcriptional level using the DNA according to any one of above (10) to (16), or the oligonucleotide or derivative thereof according to above (20);
(28) a method of inhibiting the nuclear localization of β-catenin, using an oligonucleotide or a DNA selected from the group of: (i) the DNA according to any one of above (10) to (16); (ii) the oligonucleotide or derivative thereof according to above (20); (iii) a DNA encoding bc19 protein; (iv) an oligonucleotide comprising 10 to 60 continuous nucleotides of the nucleotide sequence of the DNA encoding bc19 protein; and (v) an oligonucleotide comprising a nucleotide sequence complementary to the oligonucleotide of (iv), or a derivative thereof;
(29) a therapeutic agent for cancer. comprising an oligonucleotide or a DNA selected from the group of: (i) the DNA according to any one of above (10) to (16); (ii) the oligonucleotide or derivative thereof according to above (20); (iii) a DNA encoding bc19 protein; (iv) an oligonucleotide comprising 10 to 60 continuous nucleotides of the nucleotide sequence of the DNA encoding bc19 protein; and (v) an oligonucleotide comprising a nucleotide sequence complementary to the oligonucleotide of (iv), or a derivative thereof;
(30) a vector for gene therapy comprising the DNA according to any one of above (10) to (16);
(31) a non-human transgenic animal generated by introducing the DNA according to any one of above (10) to (16);
(32) a method of using the non-human transgenic animal according to above (31), or a non-human transgenic animal generated by introducing a DNA encoding bc19 protein as an animal model for carcinogenesis;
(33) a method of evaluating a therapeutic agent for cancer using the transgenic animal according to above (31)., or a transgenic animal generated by introducing a DNA encoding bc19 protein;
(34) a genetically defective non-human animal, wherein the function of a protein to bind to β-catenin and to localize β-catenin into the nucleus is lost or lowered due to the deletion of all or a part of the DNA according to any one of above (10) to (16);
(35) a method of screening for a substance that inhibits the binding of bc19 protein and β-catenin, comprising the steps of:
comparing the binding of bc19 protein and β-catenin in the absence [1] and presence [2] of a test sample; and
selecting a substance that inhibits the binding of the bc19 protein and β-catenin from the test sample;
(36) a method of screening for a substance that inhibits the binding of β-catenin and the protein according to any one of above (1) to (7), comprising the steps of:
comparing the binding of β-catenin and the protein in the absence [1] and presence [2] of a test sample; and
selecting a substance that inhibits the binding of β-catenin and the protein according to any one of above (1) to (7) from the test sample;
(37) a compound obtainable by the screening method according to above (35) or (36), or a pharmaceutically acceptable salt thereof;
(38) a therapeutic agent for cancer comprising the compound or pharmaceutically acceptable salt thereof according to above (37);
(39) an antibody recognizing the protein or the polypeptide according to any one of above (1) to (9);
(40) a method of immunologically detecting or quantifying the protein according to any one of above (1) to (7) using the antibody according to above (39);
(41) a neutralizing antibody that binds to the protein according to any one of above (1) to (7), and thereby inhibiting the activity of the protein to bind to β-catenin to localize β-catenin into the nucleus;
(42) a neutralizing antibody that binds to bc19 protein, and thereby inhibiting the activity of the bc19 protein to bind to β-catenin to localize β-catenin into the nucleus;
(43) a method of detecting a disease wherein the expression level of the protein according to any one of above (3) to (7) is increased or decreased in patient compared to normal healthy subject, by quantifying and comparing the expression level of the protein in normal healthy subject and a test subject by using the antibody according to above (39);
(44) a diagnostic agent comprising the antibody according to above (39), for a disease wherein the expression level of the protein according to any one of above (3) to (7) is increased or decreased in patient compared to normal healthy subjects;
(45) a method of inhibiting the transcriptional activation by a complex of β-catenin and transcription factor belonging to the Lef/Tcf family by inhibiting the function of the protein according to any one of above (1) to (7) by using the antibody according to above (41);
(46) a method of inhibiting the transcriptional activation by a complex of β-catenin and transcription factor belonging to the Lef/Tcf family by inhibiting the function of bc19 protein by using the antibody according to above (42); and
(47) a therapeutic agent for cancer comprising the antibody according to above (41) or (42).

The proteins or the polypeptides of the present invention include:
(a) a protein comprising the amino acid sequence of amino acid residues 292 to 439 in the amino acid sequence represented by SEQ ID NO: 2;
(b) the protein according to (a), wherein the protein comprises the amino acid sequence represented by SEQ ID NO: 2 or 4;
(c) a protein comprising the amino acid sequence represented by SEQ ID NO: 10;
(d) a protein comprising the amino acid sequence represented by SEQ ID NOs: 10 and 12;
(e) a protein consisting of the amino acid sequence, wherein one or more amino acids are added, deleted, or substituted in the amino acid sequence of the protein according to any one of above (a) to (d), and said protein binding to β-catenin and having the activity to localize catenin into the nucleus;
(f) a protein consisting of the amino acid sequence having a homology of 60% or more to the amino acid sequence of the protein according to any one of above (a) to (d), and said protein binding to β-catenin and having the activity to localize β-catenin into the nucleus;
(g) the protein according to above (c) or (d), wherein the protein consists of the amino acid sequence having a homology of 60% or more to the amino acid sequence represented by SEQ ID NO: 2, and binds to β-catenin and has the activity to localize β-catenin into the nucleus;
(h) a protein comprising the amino acid sequence represented by SEQ ID NO: 12; and
(i) a polypeptide comprising 5 to 60 continuous amino acid residues in the amino acid sequence of the protein according to any one of above (a) to (h).

The above-mentioned addition, deletion or substitution of amino acid(s) can be performed by introducing a site specific mutation into a DNA encoding the protein comprising the amino acid sequence represented by SEQ ID NO: 2 by site-directed mutagenesis as described in the literature (Zoller M. J. and Smith M., Nucleic Acids Res. 10: 6487 (1982); Dalbadie-McFarland G. et al., Proc. Natl. Acad. Sci. USA 79: 6409 (1982); Wells J. A. et al., Gene 34: 315 (1985); Carter P. et al., Nucleic Acids Res. 13: 4431 (1985); Kunkel T. A., Proc. Natl. Acad. Sci. USA 82: 488 (1985), etc.).

The number of amino acids to be added, deleted, or substituted are not specifically limited; however it is a number that can be added, deleted, or substituted by conventional methods, such as the above-mentioned site-directed mutagenesis, which number is one to several tens, preferably 1 to 20, more preferably 1 to 10, and further more preferably 1 to 5.

Alternatively, PCR can be performed using a pair of PCR primers which has a sequence introduced with a desired mutation (addition, deletion, or substitution) at respective 5'-terminus (Ho S. N. et al., Gene 77: 51 (1989)) to introduce a mutation into a DNA encoding the protein comprising the amino acid sequence represented by SEQ ID NO: 2. Specifically, first, using the DNA as a template, PCR is performed with a sense primer that corresponds to the 5'-terminus of the DNA and an antisense primer that corresponds to the sequence immediately before (5'-terminal to) a mutation site and contains a sequence complementary to a mutated sequence to amplify fragment A (a mutation introduced at its 3'-end) extending from the 5'-end of the DNA to the mutation site. Next, using the same DNA as a template, PCR is performed with a sense primer that corresponds to the sequence immediately after (3'-terminal to) the mutation site and comprises the mutated sequence on its 5'-terminus, and an antisense primer that corresponds to the 3'-terminus of the DNA to amplify fragment B extending from the mutation site to the 3'-end of the DNA that is introduced with a mutation at its 5'-end. These amplified fragments are purified respectively. Then, by mixing these fragments and conducting PCR without adding a template or primers, the sense strand of the fragment A and the antisense strand of the fragment B hybridize due to their common mutation sites, and the PCR reaction proceeds the hybridized strand as a template and primers to amplify the DNA introduced with the mutation.

On the other hand, a DNA encoding a partial fragment, a kind of deletion mutant, of the β-catenin nuclear localizing protein can be obtained by performing PCR with a set of primers that correspond to the nucleotide sequence at both ends of an arbitrary DNA fragment of a DNA encoding the protein having the amino acid sequence represented by SEQ ID NO: 2 using the DNA as a template.

The protein of the present invention preferably has a homology of at least 60% or more, normally 80% or more, and particularly 95% or more to the amino acid sequence represented by SEQ ID NO: 2 so as to retain the function to localize β-catenin into the nucleus.

The homology of amino acid sequences and nucleotide sequences can be determined using BLAST, an algorithm developed by Karlin and Altschul (Proc. Natl. Acad. Sci. USA 90: 5873 (1993)), or FASTA (Methods Enzymol. 183: 63 (1990)). Programs called BLASTN and BLASTX have been developed based on the BLAST algorithim (J. Mel. Biol. 215: 403 (1990)). For BLASTN analysis of a nucleotide sequence based on BLAST, the parameters are set, for example, at score=100, and wordlength=12. For BLASTX analysis of an amino acid sequence based on BLAST, the parameters are set, for example, score=50, and wordlength=3. When the BLAST and Gapped BLAST programs are used, default parameters in both programs are used. Specific procedures to perform these analyses are known to those skilled in the art and are available in the web site of National Center for Biotechnology Information (NCBI, National Library of Medicine, Building 38A, Bethesda, Md. 20894, U.S.A.).

An example of the protein comprising the amino acid sequence, wherein one or more amino acid residues are added, deleted, or substituted in the amino acid sequence represented by SEQ ID NO: 2, binding to β-catenin and having the activity to localize β-catenin into the nucleus includes a protein consisting of the amino acid sequence represented by SEQ ID NO: 4, which is a partial fragment corresponding to the residues 245 to 564 of the amino acid sequence represented by SEQ ID NO: 2.

The DNA of the present invention includes:

(j) a DNA encoding the above protein or polypeptide of the present invention, (k) a DNA comprising the nucleotide sequence of nucleotides 874 to 1317 in the nucleotide sequence represented by SEQ ID NO: 1;

(1) the DNA according to above (k), wherein the DNA comprises the nucleotide sequence of SEQ ID NO: 1 or 3;

(m) a DNA encoding a protein that binds to /β-catenin and has the activity to localize β-catenin into the nucleus, and comprising the nucleotide sequence of the following [1] or [2]:

[1] the nucleotide sequence represented by SEQ ID NO: 9; and

[2] the nucleotide sequence represented by SEQ ID NOs: 9 and 11;

(n) a DNA hybridizing to the DNA of any one of above (j) to (in) under stringent conditions, and encoding a protein that binds to β-catenin and has the activity to localize /β-catenin into the nucleus;

(o) a DNA comprising the nucleotide sequence represented by SEQ ID NOs: 9 and 11, and consisting of the nucleotide sequence having a homology of 60% or more to the nucleotide sequence of SEQ ID NO: 2, and encoding a protein that binds to β-catenin and has the activity to localize β-catenin into the nucleus; or (p) a DNA comprising the nucleotide sequence represented by SEQ ID NO: 11.

A DNA hybridizing. under stringent conditions means, for instance, those DNAs that can be obtained by colony hybridization method, plaque hybridization method, southern blot hybridization method, and such using the DNA of the present invention, such as the DNA having the nucleotide sequence represented by SEQ ID NO: 1, or partial fragment thereof, as a probe. Specifically, such DNA include those identified by immobilizing a DNA derived from a colony or plaque on a filter, subjecting the filter to hybridization in the presence of 0.7 to 1.0 mol/L NaCl at 65° C., and then washing the filter with 0.1 to 2×SSC solution (1×SSC: 150 mmol/L NaCl, 15 mmol/L sodium citrate) at 65° C. Hybridization can be performed according to methods described in "Molecular Cloning, A Laboratory Manual, Second Edition", Cold Spring Harbor Laboratory Press (1989) (hereinafter abbreviated as Molecular Cloning, Second Edition), "Current Protocols in Molecular Biology", Supplement 1-38, John Wiley & Sons (1987-1997) (hereinafter abbreviated as Current Protocols in Molecular Biology) "DNA cloning 1: Core Techniques, A Practical Approach, Second Edition", Oxford University (1995), and the like. Specifically, hybridizable DNAs include DNAs that have a homology of at least 60% or more, preferably 70% or more, more preferably 80% or more, further more preferably 90% or more, still further more preferably 95% or more, and most preferably 98% or more to the nucleotide sequence of SEQ ID NO: 1.

The oligonucleotides of the present invention include those comprising a. sequence of 10 to 60 nucleotides in the nucleotide sequence of the DNA of the present invention. However, oligonucleotides consisting of known nucleotide sequences, such as ESTs or genome draft sequences that are already published, are excluded from the oligonucleotides of the present invention.

The present invention is described below in detail. In the following description, a protein that binds to β-catenin and has the activity to localize β-catenin into the nucleus is referred to as a "β-catenin nuclear localizing protein", and the β-catenin nuclear localizing protein of the present invention having a novel amino acid sequence is referred to as a "bc19 like protein (hereinafter abbreviated as B9L protein)" due to its homology to bc19.

1. DNA Encoding β-Catenin Nuclear Localizing Protein, and Oligonucleotide Comprising Partial Sequence of the DNA

1) Preparation of DNA Encoding B9L Protein

DNAs encoding the B9L protein of the present invention (hereinafter abbreviated as B9L DNA) include a full-length B9L cDNA, a genomic DNA corresponding to. the full-length B9L cDNA, the region within the full-length B9L cDNA that encodes the B9L protein (DNA comprising the nucleotide sequence represented by SEQ ID NO: 1), and a DNA encoding the amino acid sequence represented by. SEQ ID NO: 2.

A B9L cDNA can be obtained by the yeast two-hybrid system (Fields S. et al., Nature 340: 245 (1989)).

The yeast two-hybrid system is a method for detecting the binding between a protein X of interest (generally called "bait" in the method) and a protein Y to be tested utilizing an yeast transcription factor Z, such as GAL4, that separately has a DNA binding domain (BD) and a transcriptional activation domain (AD). First, a plasmid (bait plasmid) that can express X in a host yeast cell as a fusion protein with the DNA binding domain of a transcription factor Z (hereinafter referred to as BD-X) is prepared. Next, another plasmid that can express Y in a host yeast cell as a fusion protein with the transcriptional activation domain of the transcription factor Z (hereinafter referred to as AD-Y) is prepared. Both plasmids are introduced into a host yeast cell to simultaneously express BD-X and AD-Y. Yeast cells having a genotype that can express a reporter gene under the control of a promoter which activates upon the binding of the transcription factor Z are used as the host. When the protein Y has a characteristic to bind to the protein X, BD-X and AD-Y bind to form a complex, which then binds to the promoter via the DNA binding domain (BD), and activates transcription through the transcriptional activation domain (AD) to express the reporter gene. Therefore, the expression of the reporter gene can be utilized as a marker to detect the binding between the proteins X and Y. A transformant carrying a cDNA encoding a protein Y that binds to the protein X can be isolated by screening transformants using proteins derived from a cDNA library as test protein Y and the expression of the reporter gene as a marker. Furthermore, a cDNA of interest can be cloned by isolating plasmid from the transformant.

A procedure for the cloning of B9L cDNA according to the above-mentioned method is specifically described below, using an armadillo domain of mouse β-catenin (hereinafter abbreviated as mβ-catenin arm) and yeast GAL4 as an example of bait X and transcription factor Z, respectively.

(1) Preparation of Bait Plasmid

In the present invention, mβ-catenin arm (which corresponds to the amino acid sequence of the residues 128 to 683 in mouse β-catenin) was used as bait. To prepare a bait plasmid, a DNA encoding mβ-catenin arm (hereinafter abbreviated as mβ-catenin arm DNA) which serves as the bait is necessary. Since the entire nucleotide sequence of mouse β-catenin cDNA is known to those skilled in the art (GenBank accession No: M90364; Buts, S. et al, Science 257: 1142 (1992)), the nucleotide sequence corresponding to mβ-catenin arm DNA can readily be recognized. Accordingly, an mβ-catenin arm DNA can be amplified and isolated by the RT-PCR method shown below (McPherson, M. J. et al., "PCR, A practical Approach," Oxford University Press (1991)).

Specifically, RNA is isolated from a mouse tissue or cells expressing β-catenin; cDNA is synthesized from the RNA; PCR is carried out using the cDNA as a template, a sense primer containing the nucleotide sequence corresponding to the 5' end of mβ-catenin arm DNA, and an antisense primer containing a nucleotide sequence complementary to the 3' end of the nucleotide sequence. When the 5' end of each primer for amplification is designed to have a sequence of a restriction-enzyme recognition site of a cloning vector for bait plasmid as described below, then the amplified fragment can be efficiently inserted into the cloning vector for bait plasmid. as described below by utilizing the restriction enzyme sites. If the primers are intended to have the restriction-enzyme recognition sequences for cloning, the primers are designed such that codons of the transcriptional activation domain of the transcription factor are in frame with those of mβ-catenin arm when inserted into the cloning vector.

The vector (to be preferably used to insert the mβ-catenin arm DNA prepared by the above-mentioned method) includes a vector capable of replicating in yeast *Saccharomyces cerevisiae*, and which has an appropriate marker gene for transformation, e.g., genes for amino acid biosynthesis. such as TRP1 and LEU2, and can express the DNA-binding domain of GAL4 (hereinafter abbreviated as GAL4 BD) under the regulation of a promoter for expression in yeast, e.g., alcohol dehydrogenase (ADH) promoter. In such cases, it is preferable to use a vector having appropriate restriction enzyme sites at a C-terminal portion of GAL4 BD for the insertion of mβ-catenin arm DNA, and capable of replicating in *Escherichia coil* because of convenience to handle, e.g., to purify the vector DNA, as well as having a detectable marker for transformation in *E. coli*, e.g., the ampicillin-resistance gene. Such vectors include pGBT9 (Clontech), pAS1 (Durfee, T. et al., Genes and Development 7: 555 (1993)), pAS2-1 (Clontech), and the like.

The mβ-catenin arm DNA prepared above is isolated and then inserted at a restriction enzyme site on the C-terminal side of GAL4 BD in the vector in frame of codon.

(2) Preparation of cDNA Library for Two-Hybrid System

In order to prepare a cDNA library for the expression of a fusion protein with the transcriptional activation domain of GAL4, the vector to be used can preferably replicate in yeast *Saccharomyces cerevisiae,* has an appropriate marker gene for transformation, e.g., genes for amino acid biosynthesis in yeast, such as TRP1 and LEU2, and can express the transcriptional activation domain of GAL4 (hereinafter abbreviated as GAL4 AD) under the regulation of a promoter for expression in yeast, e.g., alcohol dehydrogenase (ADH) promoter. In such cases, it is preferable to use a vector having appropriate restriction enzyme sites at a C-terminal portion of GAL4 AD, and capable of replicating also in *E. coli* because of convenience to handle, e.g., to purify the vector DNA, as well as having a detectable marker for transformation in *E. coli*, e.g., the ampicillin-resistance gene. Such vectors include pGAD (Chien, C. T. et al., Proc. Natl. Acad. Sci. USA 88: 9578 (1991)), pGAD424 (Clontech), pACT (Durfee, T. et al., Genes and Development 7: 555 (1993)), pACT2-1 (Clontech), and the like.

Proteins interacting with β-catenin in cells are predicted to be expressed in the same cells and tissues as β-catenin. β-catenin is reported as being widely expressed in adult and embryo tissues. Thus, it is possible to prepare a cDNA library by preparing cDNA from mouse tissues and cells where β-catenin is predicted to be expressed and inserting it at a restriction enzyme site on the C-terminal side of GAL4 AD in the above-mentioned vector for the expression of. fusion protein. In such cases, when the cDNA and GAL4 AD are in the same orientation and are in frame, then the fusion protein between GAL4 AD and the protein encoded by the cDNA can be expressed. Alternatively, it is possible to use a commercially available library usable in the yeast two-hybrid system, e.g., MATCHMAKER cDNA library (Clontech).

(3) Screening of cDNA by Yeast Two-Hybrid System

An yeast to be used for the introduction of the bait plasmid prepared in (1) and the cDNA library prepared in (2) includes yeasts belonging to *Saccharomyces cerevisiae*, into which the above-mentioned bait plasmid and cDNA library can be introduced, and further, it is required: (a) that the maker gene for transformation in the plasmid to be introduced and the gene of transcription factor GAL4 used in the two-hybrid system are incapable of being expressed due to their deletions or mutations; and (b) that a nucleotide sequence to which GAL4 BD can bind has been inserted in the promoter region of an appropriate reporter gene. In this case, it is preferable to use a reporter gene of which transcription is readily detected when initiated by the binding with the bait, for example, genes for amino acid biosynthesis, e.g., HIS3, etc. (in this case, the gene should be different from that used as the maker for transformation of the bait plasmid), the *E. coli* β-galactosidase gene lacZ that is detectable in yeast, and the like. For example, the host yeast includes *Saccharomyces cerevisiae* CG1945 strain (Clontech), HF7C strain (Clontech), Y153 strain (Durfee, T. et al., Genes and Development 7: 555 (1993)) CGY1::171 strain (Gill, G. and Ptashne, M., Cell 51: 121 (1987)), and the like.

The bait plasmid prepared in (1) and the cDNA library prepared in (2) can be introduced into this host yeast to select transformants containing the cDNA encoding a protein capable of binding to mβ-catenin arm using the expression of a reporter gene as a marker. For example, colonies grown on a minimum medium without histidine are selected when the HIS3 gene for histidine biosynthesis is used as the reporter gene, or colonies expressing blue color in the presence of X-gal is selected when the *E. coli* lacZ gene is used as the reporter gene.

Since selected colonies of transformant contain both types of plasmids, the bait plasmid and cDNA library, only the plasmid of cDNA library is isolated according to the method as described in references (Glover, D. M. and Hames, B. D., "DNA Cloning 2, Expression Systems, (A Practical Approach Series 149), Second Edition," Oxford University Press (1995); Chien, C. T. et al., Proc. Natl. Acad. Sci. USA 88: 9578 (1991)). Specifically, a whole DNA comprising the plasmid is isolated from the colony followed by the transformation of *E. coli* therewith. In this case, the host *E. coli* to be used is a strain that does not express a gene corresponding to the marker gene contained in the cDNA library, so that the expression of the maker gene in a transformant introduced with the maker gene can be detected. Some transformants introduced with the marker gene derived from the cDNA library are selected from the transformants, and plasmid DNAs are isolated from the selected transformants to obtain cDNA clones.

(4) Analysis of Nucleotide Sequences of cDNA Clones

Nucleotide sequences of the cDNA clones obtained in (3) can be determined, using the intact cDNA clones or alternatively after fragments of cDNA moiety are digested with appropriate restriction enzymes and subcloned into appropriate cloning vectors, e.g., pUC118, by a commonly used method for analyzing nucleotide sequence, e.g., the dideoxy-sequencing method by Sanger et al., (Proc. Natl. Acad. Sci. USA 74: 5463 (1977)) or DNA sequencer provided by Perkin Elmer, etc.

The novelty of the resulting nucleotide sequence of cDNA can be determined, by verifying that the sequence of cDNA does not exhibit significant homology to nucleotide sequences of known genes deposited in databases in the search of nucleotide sequence databases, such as GenBank, EMBL, and DDBJ, using a program for homology search, such as BLAST.

When the nucleotide sequence is novel, then, as described in (2), the cDNA clone obtained in (3) should encode a fusion protein wherein the B9L protein is connected to the C-terminus of GAL4 AD in frame. Accordingly, amino acid sequence of a protein encoded by the cDNA can be deduced by translating the revealed nucleotide sequence of cDNA to amino acid sequence in the same frame as the translational frame of GAL4 AD.

Further, known genes exhibiting homology to the protein encoded by the cDNA can be selected by searching amino acid sequence databases, such as Genpept, PIR, and Swiss-Prot, for this amino acid sequence with a program for homology search, such as BLAST, FASTA, and FrameSearch.

A cDNA having a novel nucleotide sequence as obtained above includes, for example, a cDNA comprising the nucleotide sequence represented by SEQ ID NO: 3. The cDNA encodes a protein comprising a novel amino acid sequence represented by SEQ ID NO: 4.

However, cDNAs obtained in this way are likely to be a non-full-length cDNA that fail to encode the entire protein of interest. In such cases, the entire amino acid sequence of the protein of interest can be revealed by obtaining a full-length cDNA with method shown in following (5), and translating the nucleotide sequence of the obtained full-length cDNA to the amino acid sequence in the same frame as translating the non-full-length cDNA. The nucleotide sequence of each codon of the region encoding the B9L protein is not restricted to those used in the cDNA, and includes any nucleotide sequence of any codons encoding the same amino acids so long as they encode as a whole the amino acid sequence of the entire B9L protein.

(5) Cloning of Full-Length B9L cDNA

When it is predicted that the length of B9L cDNA obtained in (3) is not full length based on a nucleotide sequence analysis in (4) as well as information on the length of mRNA obtained by Northern blot hybridization as described below, the full-length B9L cDNA can be prepared by the following method.

(5-1) Screening of cDNA Library

The cDNA library prepared in (2) which expresses the fusion protein, or a cDNA library prepared from tissues or cells expressing β-catenin where the B9L protein is presumed to be co-expressed or cells where β-catenin mRNA is detected by Northern blotting as described below, etc., is screened by colony hybridization or plaque hybridization using, as a probe, the whole cDNA obtained in (3) or a part thereof, and then cDNA clones with the length that are presumed to be full-length are selected from among the positive clones. The preparation of cDNA library and hybridization can be performed by methods described in "Molecular Cloning, Second Edition,". Alternatively, it is possible to use commercially available cDNA libraries from Clontech or others. The nucleotide sequence of full-length mouse B9L cDNA and the amino acid sequence of entire mouse B9L protein can be revealed by determining the nucleotide sequence of the resulting cDNA clones by the same method as described in (4).

(5-2) Rapid-Amplification of cDNA Ends (RACE) Method

Complementary DNAs are prepared from tissues or cells that are predicted to express the B9L protein, and then an adapter oligonucleotide is added to both ends of the cDNAs. Complementary DNA fragments containing a part extended to the 5' or 3' direction from the cDNA obtained in (3) can be obtained by 5'-RACE (rapid amplification of cDNA ends) or 3'-RACE (Frohman, M. A., Proc. Natl. Acad. Sci. USA 85: 8998 (1988)) wherein PCR is carried out using a primer from the nucleotide sequence of this adapter and a primer designed based on the nucleotide sequence of the cDNA clone obtained in (3). The nucleotide sequence of the full-length B9L cDNA can be revealed by determining the nucleotide sequence of the resulting cDNA according to the same method as described in (4).

(5-3) Use of EST Nucleotide Sequence

When the nucleotide sequence of B9L cDNA determined in (4) is analyzed by searching public nucleotide sequence databases for homology, identical sequences to the cDNA may be found among partial sequences of random cDNA clones, ESTs, even when there is no identical nucleotide sequence among known genes. In such cases, these ESTs and other ESTs containing nucleotide sequences identical to the ESTs and ESTs derived from the same clone are all collected together as the ESTs derived from the same gene. Sometimes a longer nucleotide sequence extended to the 5' or 3' direction as compared with the cDNA obtained in (4) may be found by assembling the nucleotide sequences of these ESTs that are presumed to be derived from B9L cDNA. In such cases, RT-PCR can be performed using cDNAs or a cDNA library that is prepared from a mouse tissue or cell which is expected to express the B9L protein as a template, and a sense primer comprising the nucleotide sequence of the 5'-end of the nucleotide sequence obtained by assembling those ESTs or an antisense primer comprising a nucleotide sequence complementary to the nucleotide sequence of the 3'-end to obtain a cDNA fragment that comprises a sequence extended to the 5'- or 3'-direction as compared with that of the cDNA obtained in (4). When the nucleotide sequence of the cDNA fragment is determined, and seem to correspond to the 5'- or 3'-end of the full-length B9L cDNA, it can be assembled with the nucleotide sequence of the cDNA obtained in (4) to reveal the nucleotide sequence of the full-length mouse B9L cDNA. When many EST clones considered to be derived from mouse B9L cDNA are found in known nucleotide sequence databases, the nucleotide sequence of the full-length mouse B9L cDNA may be determined, without RT-PCR, by assembling the nucleotide sequence of the EST clones.

(5-4) Preparation of Full-Length B9L cDNA

A full-length B9L cDNA clone can be prepared by amplifying the full-length B9L cDNA by PCR using cDNAs or a cDNA library prepared from mouse tissue or cell, which are expected to express the B9L protein, according to the same steps as in (3) as a template and primers that are designed based on the revealed nucleotide sequence of the 5'- and 3'-ends of the B9L full-length cDNA.

Alternatively, the B9L full-length cDNA can be prepared by transforming E. coli with a full-length B9L cDNA clone that is prepared by (1) ligating the full-length B9L cDNA clone obtained in (5-1) or the partial cDNA of 5'- or 3'-end obtained in (5-2) or (5-3) with the originally obtained B9L cDNA using the restriction enzyme sites within the cDNAs, or (2) cloning the full-length B9L cDNA clone prepared by the above PCR into an appropriate cloning vector; culturing the E. coli; and preparing plasmid DNAs from the cultured E. coli.

Escherichia coli MM294/pEGFP-C2B9L, a transformant comprising pEGFP-C2B9L, which is a plasmid DNA obtained as above comprising a DNA consisting of the nucleotide sequence represented by SEQ ID NO: 1, has been deposited under the accession number FERM BP-7291 in the International Patent Organism Depositary of the Independent Administrative Institution, National Institute of Advanced Industrial Science and Technology (Tsukuba Central 6, 1-1-1 Higashi, Tsukuba-shi, Ibaraki, Japan 305-8566) (the former National Institute of Bioscience and Human-Technology, National Institute of Advanced Industrial Science and Technology (1-1-3 Higashi, Tsukuba-shi, Ibaraki, Japan 305-8566)) on Sep. 6, 2000.

Alternatively, the B9L full-length cDNA can be chemically synthesized using DNA synthesizer based on its nucleotide sequence. Such DNA synthesizers include DNA synthesizer model 392 from Perkin Elmer that utilizes phosphoramidite method, and the like.

(6) Isolation of DNA Encoding Human B9L Protein

It is important to obtain B9L protein and a DNA encoding the protein of human than those of the mouse to analyze the mechanism underlying the onset of human colon cancer as well as to treat and diagnose the cancer. In general, proteins from different species having the same function often have amino acid sequences not identical but exhibiting homology to each other. Accordingly, the DNAs encoding the proteins are also predicted to exhibit homology to each other. In addition, mutations are accumulating in genes during the evolution of organisms, and therefore it can be assumed that the closer the phylogenetic lineage of the species, the higher the homology may be. Accordingly, it is possible to obtain B9L cDNA from other mammal, for example, human B9L cDNA, by utilizing the mouse B9L cDNA obtained in (3) or its nucleotide sequence information, according to a method as described below. When the cDNA obtained according to the method is not a full-length cDNA, the human DNA B9L can be obtained using similar methods as described in (5).

Alternatively, without obtaining mouse B9L DNA, human B9L cDNA can be directly obtained via same procedures as described in (1) to (5) of yeast two-hybrid system using human cDNA library and bait plasmid wherein the armadillo domain of human β-catenin (J. Cell Biol. 127: 2601 (1994)) serves as the bait.

(6-1) Screening of cDNA Library cDNA clones of human B9L protein can be obtained from a cDNA library that is prepared using the same method as (5-1) from human tissue corresponding to the mouse tissue which expresses mouse B9L protein or human cells derived therefrom, or from a commercially available human cDNA library of such human tissue or cells by colony hybridization or plaque hybridization under a relatively stringent condition using mouse B9L DNA labeled with radioisotope, digoxigenin, and the like as a probe.

Herein, the relatively stringent condition varies depending on the homology between human and mouse B9L cDNAs, and by performing southern blot hybridization using mouse B9L cDNA as a probe against human chromosome DNA digested with restriction enzyme under several conditions of different stringency, the most stringent condition where a hybridization band is clearly detected is selected. For instance, the relatively stringent condition for a hybridization solution without formamide can be determined by performing hybridization under several conditions where the salt concentration of hybridization solution is fixed at 1 mol/l and where the temperature gradationally varies between 68 and 42° C., and washing in 2×SSC containing 0.5%.sodium dodecyl sulfate (SDS) at the same temperature as the hybridization. Alternatively, the relatively stringent condition for a formamide-containing hybridization solution can be determined by performing hybridization at fixed temperature of 42° C., fixed salt concentration of 6×SSC, and a formamide concentration gradationally varying between 50 to 0%, and washing at 50° C. in 6×SSC containing 5% SDS.

(6-2) Isolation of DNA Encoding Human B9L Protein Utilizing EST and Human Genomic Nucleotide Sequence The nucleotide sequence of EST clones expected to be derived from human B9L cDNA or human genomic DNA sequence comprising the exon(s) of human B9L genomic DNA can be identified by searching for nucleotide sequences of human DNA that has a high homology (specifically 80% or more) with the nucleotide sequence of the mouse B9L cDNA obtained in (4), particularly at the protein coding region, in nucleotide sequence databases such as GenBank, using a homology search program such as BLAST. Such nucleotide sequences include human ESTs with GenBank accession number U46365 and R24762, and the working draft sequences of human genomic DNA with GenBank accession number AP000877, AP002357, and AP00909.

By comparing the human genomic sequences with the nucleotide sequence of mouse B9L cDNA and human ESTs, the exon sequence encoding human B9L protein, i.e., the sequence of human B9L cDNA, can be obtained. Such exon sequences of human B9L genomic DNA include the nucleotide sequence represented by SEQ ID NOs: 5 to 8. These EST clones can be obtained as EST clones of the Integrated Molecular Analysis of Genome Expression Consortium (I.M.A.G.E. Consortium) from ATCC. Alternatively, human B9L cDNA may be obtained by preparing primers that are designed based on the sequence of homologous human EST or exon of human genomic DNA, and amplifying DNA fragments by RT-PCR as described in (3) using mRNA prepared from human tissue or cell that are expected to express the B9L protein as a template.

(7) Isolation of B9L Genomic DNA

Genomic DNA of mouse or human B9L gene can be obtained by screening according to methods such as plaque hybridization, described in "Molecular Cloning, second edition" using the mouse or human B9L cDNA obtained in (3) or (6) as a probe against a genomic DNA library prepared from chromosomal DNA isolated from a cell or tissue of mouse or human. The exon-intron structure of the B9L gene can be identified through the comparison of the nucleotide sequences of the B9L genomic DNA and the B9L cDNA. Furthermore, using the 5'-end portion of the cDNA as a probe, the nucleotide sequence of regions of the genomic gene that regulate transcription, such as the promoter of the B9L gene, can be identified. Such sequence is useful for analyzing the mechanism of transcriptional regulation of the B9L gene. Furthermore, clones may be prepared wherein the B9L gene on the chromosome is inactivated or substituted with arbitrary sequence using the technique of homologous recombination (Kuehn M. R. et al., Nature 326: 295 (1987); Thomas K. R. and Capecchi M. R., Cell 51: 503 (1987)).

(8) Preparation of B9L Oligonucleotides

An oligonucleotide comprising a partial sequence of the B9L DNA of the present invention or sequence complementary thereto (hereinafter abbreviated as B9L oligonucleotide) can be prepared by the DNA synthesizer described above in (5).

Specifically, such B9L oligonucleotides include DNAs comprising a sequence identical to 10 to 60 continuous nucleotides of the nucleotide sequence represented by SEQ ID NO: 1 or DNAs comprising a sequence complementary thereto. For the use of such DNAs as sense or antisense primers, oligonucleotides whose melting temperature and number of nucleotides does not extremely change is preferable.

Furthermore, derivatives of the above oligonucleotides (hereinafter referred to as oligonucleotide derivative) may be also used as an oligonucleotide of the present invention. Example of the oligonucleotide derivatives include oligonucleotide derivatives wherein the phosphodiester bond of the oligonucleotide has been converted to a phosphorothioate bond; oligonucleotide derivatives wherein the phosphodiester bond in the oligonucleotide has been converted to a N3'-P5' phosphoramidite bond; oligonucleotide derivatives wherein the ribose and phosphodiester bond in the oligonucleotide has been converted to a peptide-nucleic acid bond; oligonucleotide derivatives wherein uracil of the oligonucleotide has been substituted with C-5 propynyluracil; oligonucleotide derivatives wherein uracil of the oligonucleotide has been substituted with C-5 thiazoleuracil; oligonucleotide derivatives wherein cytosine of the oligonucleotide has been substituted with C-5 propynylcytosine; oligonucleotide derivatives wherein cytosine of the oligonucleotide has been substituted with phenoxazine-modified cytosine; oligonucleotide derivatives wherein ribose of the oligonucleotide has been substituted with 2'-o-propylribose; oligonucleotide derivatives wherein ribose of the oligonucleotide has been substituted with 2'-methoxyethoxyribose, and the like (Yokoyama K., Saibo Kogaku (Cell Technology) 16-1463 (1997)).

2) Preparation of DNA Encoding bc19 Protein and Oligonucleotide Comprising Partial Nucleotide Sequence of the DNA bc19 protein has approximately 37% homology throughout the sequence at the amino acid sequence level to the mouse B9L protein obtained by the above-described methods. According to the present invention, the bc19 protein was revealed to bind to β-catenin, and thus was considered as a β-catenin nuclear localizing protein. The nucleotide sequence of the full-length cDNA encoding human bc19 protein and the amino acid sequence encoded by the cDNA are known in the art (Willis T. G. et al., Blood 91: 1871 (1998)). A DNA or oligonucleotide that encodes the bc19 protein can be obtained from human cDNA or genomic DNA by the methods described in above (5-4) (7), and (8). Furthermore, bc19 DNA from animals other than human, such as mouse, can be obtained using the same method as described in above (6).

2. Process for Producing β-Catenin Nuclear Localizing Protein or Partial Peptide Thereof, and Method for Measuring the Activity Thereof Aβ-catenin nuclear localizing protein of the present invention, such as B9L protein or bc19 protein, or a partial peptide thereof can be produced by expressing a DNA encoding the β-catenin nuclear localizing protein or partial peptide thereof prepared in above 1 in host cells according to methods described in "Molecular Cloning, Second Edition"; Glover D. M. and Hames B. D., "DNA Cloning 1: Core Techniques, A Practical Approach, Second Edition.", Oxford University Press (1995), etc. Although a method is described below taking the B9L protein as an example, the bc19. protein and partial peptides thereof can be also produced by the same method.

Specifically, the B9L protein of the present invention can be produced by preparing a recombinant vector wherein B9L DNA has been inserted into downstream of a promoter in an appropriate expression vector, introducing the vector to host cells to obtain a transformant expressing the B9L protein, and then culturing the transformant.

The expression vector to be used is a vector that is capable of autonomous replication or being integrated into chromosome in host cells and contains a promoter directing transcription from B9L DNA to mRNA in host cells.

Any host cells can be used including prokaryotic cells, yeast cells, animal cells, insect cells, plant cells, and the like, as far as the cells can express the gene of interest. Animal individuals and plant bodies are also usable.

When prokaryotes such as bacteria are used as host cells, then expression vectors to be used are capable of autonomous replication in the host prokaryote and B9L DNA should be placed downstream of a promoter containing ribosome-binding sequence. It is preferable that the distance between the ribosome-binding sequence and the initiation codon has been adjusted appropriately (for example, 6 to 18 nucleotides for a vector of *E. coli* host). It is preferable to place a transcription termination sequence immediately downstream of B9L DNA, although it is not essential in the invention. In addition, the vector should be designed to contain sequences for the expression of marker gene, such as drug-resistance genes, for the convenience of selection of transformants.

Any promoter can be used, as far as it has the ability to direct the expression in host cells. For example, when *E. coli* is used as a host, the promoters include promoters derived from *E. coli* and phage, such as trp promoter (Ptrp), lac promoter (Plac), PL promoter, T7 promoter, $P_R$ promoter, etc. It is also possible to use artificially designed or modified promoters, such as promoters wherein two Ptrp are tandemly connected to each other, or tac promoter, T7-lac promoter, let I promoter, etc. When *Bacillus subtilis* is used as a host, the promoters include promoters derived from SPO1 and SPO2 that are *Bacillus subtilis* phages, as well as PenP promoter.

The expression vector is exemplified, for example, by pSE280 (Invitrogen), pGEMEX-1 (Promega), pQE-8 (QIAGEN), pKYP200 (Agric. Biol. Chem. 48: 669 (1984)), pLSA1 (Agric. Biol. Chem. 53:277 (1989)), pGEL1 (Proc. Natl. Acad. Sci. USA 82: 4306 (1985)), pbluescript II SK(–) (Stratagene), pKK223-3 (Amersham Pharmacia Biotech), pGEX-5x-3 (Amersham Pharmacia Biotech), and pET14 (Novagen).

The host cells can be microorganisms belonging to the genus Escherichia, the genus Serratia, the genus Bacillus, the genus Brevibacterium, the genus Corynebacterium, the genus Microbacterium, the genus Pseudomonas, and the like, for example, *Escherichia coli* XL1-Blue, *Escherichia Coli* XL2-Blue, *Escherichia coli* DH1, *Escherichia coli* MC1000, *Escherichia coli* KY3276, *Escherichia coli* W1485, *Escherichia coli* JM109, *Escherichia coli* HB101, *Escherichia coli* No. 49, *Escherichia coli* W3110, *Escherichia Coli* NY49, *Serratia ficaria, Serratia fonticola, Serratia liquefaciens, Serratia marcescens, Bacillus subtilis, Bacillus amyloliquefaciens, Brevibacterium ammoniagenes, Brevibacterium immariophilum* ATCC14068, *Brevibacterium saccharolyticum* ATCC14066, *Corynebacterium glutamicum* ATCC13032, *Corynebacterium glutamicum* ATCC14067, *Corynebacterium glutamicum* ATCC13869, *Corynebacterium acetoacidophilum* ATCC13870, *Microbacterium ammoniaphilum* ATCC15354, Pseudomonas sp. D-0110.

Any method for introducing recombinant vectors can be used, as long as such methods have the ability to introduce DNAs to the above-mentioned host cells. Such methods include, for example, electroporation (Dower, W. J. et al., Nucleic Acids Res. 16: 6127 (1988)), methods using calcium ion (Cohen, S. N. et al., Proc. Natl. Acad. Sci. USA 69: 2110 (1972); Reid, J. D. et al.,Gene 17: 107 (1982)), and protoplast method (Unexamined Published Japanese Patent Application No. (JP-A) Sho 63-248394; Chan, S. and Cohen, S. N., Mol. Gen. Genet. 168: 111 (1979)).

When yeast is used as a host cell, expression vectors to be utilized include vectors containing a promoter directing transcription in host yeast, B9L DNA, transcription termination sequence, and a sequence capable of expressing a maker gene for transformation in yeast (e.g., drug resistance genes and genes for amino acid biosynthesis such as TRP1, HIS3, and LEU2). Further, it is preferable to use an expression vector capable of autonomous replication and capable of expressing a drug-resistance gene that can be utilized as a marker for transformation in *E. coli* for the convenience of preparation and maintenance of the vector.

Any promoter can be used as long as it is operable in yeast. Such promoters include, for example, promoters of the alcohol dehydrogenase gene ADH1 and genes involved in galactose metabolism, e.g., GAL1, GAL10; promoter of the acid phosphatase gene PHO5; promoter of the phosphoglycerate kinase gene PGK; promoter of the glycelaldehyde-3-phosphate dehydrogenase gene GAP; promoters of genes for heat shock proteins; promoter of α-mating factor gene MFα1; and promoter of the copper-metallothionein gene CUP1 derived from *Saccharomyces cerevisiae*; as well as promoter of alcohol oxidase gene. AOX1 derived from *Pichia pastoris*.

The host cells include yeast strains belonging to the genus Saccharomyces, the genus Schizosaccharomyces, the genus Pichia, and the like, specifically, include *Saccharomyces cerevisiae, Schizosaccharomyces pombe, Pichia pastoris*, etc.

Any method for introducing recombinant vectors can be used, as far as such methods have the ability to introduce DNAs to yeast. Such methods include, for example, electroporation (Becker, D. M. and Guarente, L., Methods. Enzymol. 194: 182 (1991)), spheroplast method (Shortel, D. et al., Proc. Natl. Acad. Sci. USA 81: 4889 (1984)), lithium acetate method (Ito, H. et al, Journal of Bacteriology 153: 163 (1983)), etc.

When animal cells are used as hosts, expression vectors to be utilized include vectors containing a promoter directing transcription in host animal cells, B9L DNA, and signal sequences for transcription termination and polyadenylation of the transcripts. Further, it is preferable to use an expression vector capable of autonomous replication and capable of expressing a drug-resistance gene that can be utilized as a marker for transformation in *E. coli* for the convenience of preparation and maintenance of the vector. Any promoter can be used, as far as it has the ability to direct the transcription in animal cells. Such promoters include virus-derived sequences, such as SV40 early promoter, promoter and enhancer elements of human cytomegalovirus IE (immediate early) gene, LTRs originating from retroviruses such as Rous sarcoma virus, human T cell leukemia virus I, Moloney murine leukemia virus, etc.; or promoters from genes, such as metallothionein gene, β-actin gene, elongation factor-1, and the like, derived from animal cells. Furthermore, it is possible to use artificial promoters wherein multiple promoter elements as listed above have been combined together, e.g., SRα promoter created by combining SV40 early promoter and LTR from human T cell leukemia virus I.

Cells wherein B9L DNA has been integrated in the host chromosomal DNA and which constitutively expresses B9L can be selected by introducing a B9L expression vector containing a sequence for the expression of a drug-resistance gene against a drug, such as G418 or hygromycin, into the host cells and culturing the cells in the presence of the drug. Furthermore, in order to increase the amount of B9L protein produced in host cells, a vector for constitutive expression of the B9L protein, which contains a sequence for the expression of the dihydrofolate reductase (dhfr) gene, is introduced into host cells, and the cells are cultured while the concentration of methotrexate, a dhfr inhibitor, is successively being increased; and thus it is possible to successfully achieve the amplification. of the copy number of B9L DNA together with that of the dhfr gene. Such host cells, in which the gene amplification utilizing the dhfr gene is achieved, can be cells that have no functional dhfr gene, for example, CHO/dhfr⁻ (ATCC: CRL-9096) and the like.

Vectors to be used for the preparation of the above-mentioned B9L expression vector specifically include, for example, pEGFP-C2 (Clontech), pAGE107 (Japanese Unexamined Patent Application No. 22979/91; Miyaji, H., Cytotechnology 3: 133, (1990)), pAS3-3 (Japanese Unexamined Patent Application No. 227075/90), pCDM8 (Seed, B., Nature 329: 840 (1987)), pcDNA3.1(+)(Invitrogen), pREP4 (Invitrogen), PBK-RSV (Stratagene), pSVK3 (Amersham Pharmacia Biotech), pcDNA1.1/Amp (Invitrogen), and pAMo (Sasaki, K., J. Biol. Chem. 268: 22782 (1993)).

Expression vectors for B9L proteins in animal cells include pEGFP-C2B9L wherein the mouse B9L full-length cDNA is inserted at the ECORI-SalI site of the pEGFP-C2-vector. *Escherichia coli* MM294/pEGFP-C2B9L, a transformant comprising pEGFP-C2B9L, has been deposited under the accession number FERMBP-7291 in the International Patent Organism Depositary of the Independent Administrative Institution National Institute of Advanced Industrial Science and Technology (Tsukuba Central 6, 1-1-1 Higashi, Tsukuba-shi, Ibaraki, Japan 305-8566) (the former National Institute of Bioscience and Human-Technology, National Institute of Advanced Industrial Science and Technology (1-1-3 Higashi, Tsukuba-shi, Ibaraki, Japan 305-8566)) on Sep. 6, 2000.

The host cells include the following cell lines: HeLa, Namalwa, and 293, which are derived from human; COS-1 and COS-7, which are kidney cells form African green monkey; CHO and BHK, which are derived from hamster; NHI3T3, which is derived from mouse embryo cell; mouse myeloma, SP2/0 and NSO; and rat myeloma YB2/0.

Any method for introducing recombinant vectors can be used, as far as such methods have the ability to introduce DNAs to animal cells. Such methods include, for example, electroporation (Miyaji, H. et al., Cytotechnology 3: 133 (1990)); calcium phosphate method (Japanese Unexamined Patent Application No. 227075/90), lipofection method (Felgner, P. L. et al., Proc. Natl. Acad. Sci. USA 84: 7413 (1987)), etc.

When insect cells are used as host cells, the baculovirus expression system (O' Reilly, D. R. et al., "Baculovirus Expression Vectors: A Laboratory Manual", W. H. Freeman and Company, New York (1992); Luckow, V. A. and Summers, M. D. et al., Bio/Technology 6: 47 (1988)) can be utilized. Specifically, after inserting B9L DNA in a vector called transfer vector, both vector and baculovirus are concurrently introduced into insect cells; the resulting homologous recombination provides a recombinant baculovirus in which B9L DNA has been inserted downstream of the polyhedrin gene promoter that is a highly efficient promoter; then, the recombinant baculovirus can be infected again to the insect cells, and thereby achieving the expression of B9L protein.

Such baculovirus to be utilized includes *Autographa californica* nuclear polyhedrosis virus, *Bombyx mori* nuclear polyhedrosis virus, etc. The insect cells to be used can be Sf9 and Sf21 that are cells derived from *Spodoptera frugiperda* (O' Reilly, D. R. et al., "Baculovirus Expression Vectors: A Laboratory Manual", W. H. Freeman and Company, New York (1992)), High5 (Invitrogen) which is a cell derived from *Trichoplusia ni* and the like. Alternatively, silkworm larvae per se are also usable. The transfer vector contains the polyhedrin promoter and a sequence derived from baculovirus for directing homologous recombination, also sequences for the maintenance and replication of vector as well as for the insertion of foreign genes (a sequence capable of autonomous replication in *E. coli* and a sequence of drug resistance gene), and the like for the convenience of gene manipulation in *E. Coli*. Specifically such vectors include pVL1392, pVL1393, pBluebac4 (both from Invitrogen) etc.

B9L protein can be produced using animal individuals. For example, B9L protein can be produced in an animal body in which B9L DNA has been introduced according to a known method (Colman, A., American Journal of Clinical Nutrition 63: 639S. (1996); Rosen, J. M. et al, American Journal of Clinical Nutrition 63: 627S (1996); Wright, G. et al., Bio/Technology 9: 830 (1991)).

Any promoter can be used, as far as it has the ability to direct the expression in animals. For example, α-casein promoter, β-casein promoter, β-lactoglobulin promoter, whey acidic protein promoter, and the like that are promoters specific to mammary gland cells are preferably used.

When plant cells or plant bodies are used as hosts, B9L can be produced according to known methods (Izawa, T., Sosiki Baiyou (Tissue Culture) 20: 6 (1994); Hashimoto, T., Sosiki Baiyou (Tissue Culture) 21: 14 (1995); Miele, L., Trends in Biotechnology 15: 45 (1997))

Any promoter can be used for the expression of B9L DNA, as far as it has the ability to direct gene expression in plant cells. Such promoters include, for example, 35S promoter of cauliflower mosaic virus, actin-1 promoter of rice, etc. Furthermore, intron 1 of the maize alcohol dehydrogenase gene and the like can be inserted between the promoter and B9L DNA to be expressed to increase the expression efficiency of the B9L DNA.

The host cells can be plant cells derived from potato, tobacco, maize, rice, rape, soybeans, tomato, wheat, barley, rye, alfalfa, flax, etc.

Any method can be used for introducing recombinant vectors, as far as the method has the ability to introduce DNAs to plant cells. Such methods include, for example, methods using Agrobacterium, electroporation (Miyaji, H., Cytotechnology 3: 133 (1990)), methods using particle gun (gene gun), etc.

Plant cells or organs in which B9L DNA has been introduced can be cultured on a large scale using jar fermenter. Also, plant cells containing introduced genes can be regenerated to create plant bodies (transgenic plant) in which B9L DNA has been introduced.

Microorganisms, animal cells, or transformants derived from a plant cell, which contain a recombinant vector containing the B9L DNA of the present invention as an insert, can be cultured according to a typical culture method, then B9L protein is allowed to produce and accumulate therein, and the B9L protein is recovered from the culture in order to produce the B9L protein.

Media to be used for the cultivation of transformants obtained using animal cells as hosts include commonly used RPMI1640 medium (The Journal of the American Medical Association 199: 519 (1967)), Eagle's MEM (Eagle, H., Science 122: 501 (1952)), Dulbecco's modified Eagle's medium (Dulbecco, R. and Freeman, G., Virology 8:396 (1959)), 199 medium (Proceeding of the Society for the Biological Medicine 73: 1 (1950)) and these media containing fetal calf serum or the like. If desired, an antibiotic such as penicillin or streptomycin may be added to the medium. Generally, the cultivation can be performed under a condition such as at a pH of 6 to 8, at 30 to 40° C., in the presence of 5% $CO_2$ for 1 to 7 days.

Media to be used for the cultivation of transformants obtained using insect cells as host cells include commonly used TNM-FH medium (Pharmingen); Sf-900 II SFM medium (Life-Technologies), ExCell400 and ExCell405 (both from JRH Biosciences); Grace's Insect Medium (Grace, T. D. C., Nature 195: 788 (1962)), and the like. The preferable culture condition is at pH of 6 to 7; culture temperature is at 25 to 30° C., and culturing is carried out for 1 to 5 days. Further, if desired, an antibiotic, such as gentamicin, may be added to the medium during the culture.

When the transformant is an animal individual or a plant body, it is possible to produce B9L protein by breeding or cultivating it according to the usual method, allowing the B9L protein to produce and accumulate and recovering the B9L protein from the animal individual or plant body.

Specifically, in the case of an animal individual, for example, it is possible to produce the B9L protein by breeding a non-human transgenic animal containing B9L DNA, allowing the B9L protein encoded by the recombinant DNA to be produced and accumulated in the animal body, and recovering the B9L protein from the animal. The sites for the production and accumulation of the protein in the animal include, for example, milk and egg of the animal.

In the case of plant body, for example, it is possible to produce the B9L protein by cultivating transgenic plant containing B9L DNA, allowing the B9L protein encoded by the recombinant DNA to be produced and accumulated in the plant, and recovering the B9L protein from the plant.

Any of natural media and synthetic media can be used for the culture of transformant obtained using, as a host, a prokaryote such as *E. coli* or eukaryote such as yeast, as far as it contains carbon source, nitrogen source, inorganic salts, and the like which the organism can assimilate; and the culture of the transformant is achieved efficiently in it.

Any carbon source that is assimilated by the organisms can be used, including glucose, fructose, sucrose, and molasses containing thereof; carbohydrates such as starch and starch hydrolysate; organic acids such as acetic acid and propionic acid; alcohols such as ethanol and propanol.

Nitrogen source that can be utilized includes ammonia; ammonium chloride; ammonium salts of inorganic and organic acids, such as ammonium sulfate, ammonium acetate, ammonium phosphate; other nitrogen-containing compounds; as well as, peptone, meat extract, yeast extract, corn steep liquor, casein hydrolysate, soybean cake and soybean cake hydrolysate, various fermentation microorganisms, and digests thereof.

Such inorganic salts include potassium dihydrogenphosphate, dipotassium hydrogenphosphate, magnesium phosphate, magnesium sulfate, sodium chloride, ferrous sulfate, manganese sulfate, copper sulfate, calcium carbonate, etc The culture is generally carried out under an aerobic condition such as by shaking culture or submerged spinner culture under aeration. It is preferable to perform the culture at 15 to 40° C. and generally for 16 to 96 hours. The pH should be maintained at 3.0 to 9.0 during the culture. The adjustment of pH can be conducted using an inorganic or organic acid, alkaline solution, urea, calcium carbonate, ammonia, etc. If desired, antibiotic such as ampicillin or tetracycline may be added to the medium during the culture.

In the case of culturing microorganisms transformed with an expression vector using an inducible promoter, if desired, an inducer can be added to the medium. For example, in the case of culturing microorganisms transformed with an expression, vector using lac promoter, IPTG or the like can be added to. the medium; and in the case of culturing microorganisms transformed with an expression vector using trp promoter, indoleacrylic acid or the like can be added to the medium.

The following general methods for the isolation and purification of proteins can be used to isolate and purify B9L protein accumulated in the culture of the above-mentioned transformant.

When B9L protein is secreted from the cells, the B9L protein accumulates in the medium. Accordingly, after the culture is completed, medium alone, from which the cells have been removed, can be recovered by techniques such as centrifugal separation. It is possible to obtain purified sample from the medium using general methods singly or in combination for the isolation and purification of proteins; specifically, solvent extraction; salting out using ammonium sulfate or the like; desalting; organic-solvent precipitation; anion exchange chromatography using resins, such as DEAE Sepharose, DIAION HPA-75 (Mitsubishi Chemical), and Mono-Q (Amersham Pharmacia Biotech); cation exchange chromatography using resins such as SP Sepharose (Amersham Pharmacia Biotech); hydrophobic chromatography using resins such as butyl-Sepharose and phenyl-Sepharose; gel filtration using molecular sieve; affinity-chromatography; chromato-focusing; electrophoretic techniques such as isoelectric focusing; etc.

When B9L protein is accumulated in cells of transformant, after the culture is completed, the cells of transformant are recovered from the culture by techniques, such as centrifugation, subsequently suspended in a buffer and then disrupted using a sonicator, French press, or the like to give cell-free extract.

When B9L protein is soluble in the cells, purified sample can be obtained from the supernatant after centrifuging the cell-free extract by the same method as used for the purification and isolation from the above-mentioned medium. Alternatively, when B9L protein is present as inclusion bodies in cells, the cell-free extract is treated by centrifugation, and then the inclusion bodies of the B9L protein can be recovered as precipitated. fraction. The inclusion bodies of the B9L protein is solubilized by a protein denaturant, and then the resulting solution is dialyzed as to contain no protein denaturant or so dialyzed or diluted that such a low level of protein denaturant does not denature the protein to restore the normal tertiary structure of the B9L protein. Subsequently, purified sample can be obtained by the same method for the isolation and purification as described above.

In addition, B9L protein can be produced by in vitro transcription-translation system according to known methods (Kigawa, T., J. Biomolecular NMR 6: 129; Spirin, A. S., Science 242: 1162; Kigawa, T. and Yokoyama, S., J. Biochem. 110: 166 (1991)). Specifically, B9L DNA is ligated downstream of a promoter, such as SP6, T7, or T3 and an RNA polymerase specific to each promoter is allowed to react thereto for the synthesis of large amount of B9L RNA in vitro. Thus, the B9L protein can be produced by a cell-free translation system, e.g., translation system utilizing rabbit reticulocyte lysate or wheat germ extract.

The structural analysis for the purified B9L protein can be carried out by commonly used methods in protein chemistry, for example, a method as described in "Protein Structural Analysis for Gene Cloning" (H. Hirano, Tokyo Kagaku Doujin, 1993).

Whether a B9L protein or bc19 protein, or derivatives or partial fragments thereof wherein amino acids are substituted, deleted, or added to the. amino acid sequence of the protein or proteins having homology to the protein at the amino acid sequence level (hereinafter referred to as B9L/bc19 analogues) binds to β-catenin or not can be determined by detecting the transcription of reporter gene in the yeast two-hybrid system described in section 1 using a fusion protein expression vector comprising DNAs encoding a transcriptional activation domain and the protein, and a β-catenin bait plasmid.

Alternatively, the binding can be examined by the following steps: directly mixing a B9L/bc19 analogue and β-catenin in vitro to allow binding reaction, or expressing a B9L/bc19 analogue in cells to allow their binding in cells; then performing immunoprecipitation against the reaction mixture or cell lysate using an antibody against β-catenin; and detecting, by immunoblotting or the like, whether the B9L/bc19 analogue is present in the precipitates. It can be also examined without the use of antibodies by the following steps: preparing a fusion protein of a B9L/bc19 analogue and a protein or peptide, such as GST, that facilitates purification; performing binding reaction using β-catenin labeled with $^{35}S$ or the like; purifying. the fusion protein of the B9L/bc19 analogue; and detecting, by autoradiography or the like, whether the labeled β-catenin is present in the purified fraction.

The ability of B9L/bc19 analogues to cause localization of β-catenin into the nucleus can be examined by fixing cells wherein both β-catenin and a B9L/bc19 analogue are forcedly expressed, and cells wherein β-catenin alone is forcedly expressed, and detecting β-catenin in the cells, respectively, by immunostaining with anti-β-catenin antibody. In this case, normal β-catenin is restrained by degradation with GSK-3β in the cell. Therefore, use of phosphorylation site mutants that escape degradation and thus accumulates, for example, a β-catenin mutant wherein serine 33 is replaced with tyrosine, will increase the intracellular level of β-catenin and enables a more readily detection of β-catenin in the cell. β-catenin does not have a particular intracellular localization and distributes ubiquitously within cells wherein β-catenin alone is forcedly expressed. However, when B9L/bc19 analogues have the activity to localize β-catenin into the nucleus, β-catenin is detected more in the nucleus than in the cytoplasm. Such B9L/bc19 analogues with β-catenin nuclear localizing activity include B9L protein, and partial fragment thereof encoded by cDNA clones obtained by the yeast two-hybrid system in the present invention (corresponding to the region comprising the amino acid residues from 245 to 564 of the amino acid sequence of mouse B9L protein; represented by SEQ ID NO: 4).

B9L protein and bc19 protein increase the level of β-catenin localizing to the nucleus. Thus, the proteins are expected to promote transcriptional activation mediated by the β-catenin/TCF complex.

The effect of B9L/bc19 analogues, including B9L and bc19 proteins themselves, on transcriptional activation through the β-catenin/TCF complex following Wnt signal transduction can be examined using a plasmid, for example, pTOPFLASH and pTOPCAT (both described in Korinek V. et al., Science 275: 1784 (1997)), wherein a reporter gene, such as luciferase, chloramphenicol acetyltransferase, or β-galactosidase, is placed downstream of a promoter that contains a TCF binding sequence so that the transcription is activated by the_β-catenin/TCF complex. The above reporter gene expression plasmid and an expression plasmid of a mutant β-catenin, for example, wherein serine 33 is substituted with tyrosine, that can constitutively bind to a protein belonging to the TCF/Lef family to activate transcription are introduced into animal cells. Then, by measuring and comparing the expression levels of the reporter gene with and without further introduction of an expression plasmid of B9L/bc19 analogue, it can be determined whether the B9L/bc19 analogue can further promote the transcriptional activation by the β-catenin/TCF complex.

3. Preparation of Antibody Recognizing β-Catenin Nuclear Localizing Protein (1) Preparation of Polyclonal Antibody A polyclonal antibody can be prepared by immunizing animals using the full-length or partial protein of a β-catenin nuclear localizing protein obtained by the method described in the above section 2 or a partial peptide of a β-catenin nuclear localizing protein prepared by chemical synthesis with peptide synthesizer, and the like as an antigen.

Rabbits, goats, rats, mice, hamsters, and the like can be used as such animals for immunization. The dose of the antigen is preferably 50 to 100 μg per animal.

To use a partial peptide as the antigen, the partial peptide is preferably covalently conjugated with a carrier protein, such as KLH or bovine thioglobulin.

After the first administration, the antigen is administered 3 to 10 times at 1 to 2-week intervals. 3 to 7 days after each time of administration, blood is collected from the venous plexus of eyegrounds. Then the serum is tested for there activity to the antigen used for the immunization by a method of enzyme immuno-assay (Ishikawa, E., "Kousomeneki Sokuteihou (Methods of Enzyme Immuno-Assay)", Igakushoin (1978); Harlow, E. and Lane, D., "Antibodies: A Laboratory Manual", Cold Spring Harbor Laboratory. Press (1988), etc.

The polyclonal antibody can be obtained by collecting the sera from non-human mammals that have exhibited sufficiently high antibody titers in their sera against the antigen used for the immunization, and separating and purifying the sera.

Such methods for the separation and purification include centrifugal separation, salting out with 40 to 50% saturated ammonium sulfate, precipitation by caprylic acid (Harlow, E. and Lane, D., "Antibodies: A Laboratory Manual", Cold Spring Harbor Laboratory, (1988)),and a procedure for processing using singly or in combination chromatographic methods, e.g., using DEAE-Sepharose column, anion exchange column, protein-A or -G column, gel filtration column, etc.

(2) Preparation of Monoclonal Antibody (2-1) Preparation of Antibody-Producing Cells Rats, of which sera have exhibited sufficiently high titers of antibody against the antigen used for the immunization as describe above in (1), are provided as the source of antibody-producing cells. 3 to 7 days after the final administration of the antigen substance to the rats which have exhibited such antibody titers, spleens are excised.

The spleens are sectioned into small pieces in MEM and crushed by forceps. After centrifugation at 1200 rpm for 5 minutes, the supernatant is discarded.

The resulting precipitated fraction of spleen cells is treated with Tris-ammonium chloride buffer (pH 7.65) for 1 to 2 minutes to remove red blood cells, then the spleen cells are washed 3 times with MEM. The spleen cells prepared are used as antibody-producing cells.

(2-2) Preparation of Myeloma Cells

Myeloma cell to be used is a cell line established from mouse or rat. For example, 8-azaguanine resistant mouse (BALB/c-derived) myeloma cell lines that are usable include P3-X63Ag8-Ul(P3-U1) (Yelton, D. E., Curr. Topics Microbiol. Immunol. 81: 1 (1978); Kohler, G. and Milstein, C., Eur. J. Immunol. 6: 511 (1976)), SP2/0-Ag14 (SP-2) (Shulman, M. et al., Nature 276: 269 (1978)), P3-X63-8653 (653) (Seeger, R. C. et al., J. Immunol. 123: 1548 (1979)), P3-X63-Ag(X63) (Kohler, G. and Milstein, C., Nature 256: 495 (1975)), and the like. Cells of these lines are passaged in 8-azaguanine medium [RPMI1640 medium containing 1.5 mmol/L glutamine, $5\times10^{-5}$ mol/L 2-mercaptomethanol, 10 μg/ml gentamicin, and 10% fetal calf serum (CSL) (hereinafter referred to as normal medium) further containing 15 μg/ml 8-azaguanine], but 3 to 4 days before the cell fusion the cells are cultured in the normal medium. $2\times10^7$ or more cells are used for the fusion.

(2-3) Preparation of Hybridoma

The antibody-producing cells prepared as described in (2-1) and myeloma cells in (2-2) are washed well with MEM or PBS (1.83 g of disodium phosphate, 0.21 g of potassium dihydrogenphosphate, 7.65 g of sodium chloride, 1 L of distilled water; pH 7.2), the cells are mixed with each other at a ratio of the numbers of antibody-producing cells: myeloma cells=5 to 10:1. After the mixture was subjected to centrifugation at 1200 rpm for 5 minutes, the supernatant is discarded.

The mixed cells prepared from the precipitated fraction are well dispersed. While the cells are being stirred at 37° C., 0.2 to 1 ml (per $10^8$ antibody-producing cells) of solution of 2 g PEG-1000, 2 ml MEM, and 0.7 ml DMSO is added to the cell mixture; then 1 to 2 ml of MEM is added thereto several times at 1 to 2-minute intervals.

After the addition, the cells are prepared by further adding MEM so that the total volume becomes 50 ml.

The suspension prepared is subjected to centrifugation at 900 rpm for 5 minutes, and then the supernatant is discarded.

The cells from the resulting precipitated fraction are gently dispersed and then suspended by gentle pipetting with a measuring pipette in 100 ml of HAT medium (a medium wherein $10^{-4}$ mol/L hypoxanthine, $1.5\times10^{-5}$ mol/L thymidine, and $4\times10^{-7}$ mol/L aminopterin have been added to the normal medium).

A 100 μl aliquot of the suspension was dispensed into each well of a 96-well culture plate. Then the cells are cultured in an incubator with 5% $CO_2$ at 37° C. for 7 to 14 days.

After the culture is completed, an aliquot of the culture supernatant is utilized for the selection of hybridomas specifically reacting to the antigen used for the immunization according to the enzyme immuno-assay method as described in "Antibodies-A Laboratory Manual" (Harlow, E. and Lane, D., Cold Spring Harbor Laboratory Press, Chapter 14 (1988)), etc. to obtain the above-mentioned antibody-producing cells.

A specific example of the enzyme immuno-assay method is as follows:

An appropriate plate is coated with a purified sample of the full-length protein of the present invention or a partial fragment thereof used as an antigen for the immunization. The hybridoma culture supernatant or purified antibody obtained in (2-4) as described below is reacted as a primary antibody, and an anti-rat immunoglobulin antibody labeled with biotin, enzyme, chemically-luminescent substance, radioisotope, or the like is further reacted as a secondary antibody in the plate. Subsequently, a reaction is carried out according to the label substance, and cells exhibiting the specific reactivity to the protein of the present invention are selected as hybridomas producing monoclonal antibody against the protein of the present invention.

The hybridomas are cloned twice by limiting dilution method [with HT medium (HAT medium without aminopterin) in the first cloning, and with the normal medium in the second]. Cells that stably exhibit high antibody titers are selected as hybridoma lines producing monoclonal antibody against the protein of the present invention.

(2-4) Preparation of Monoclonal Antibody

The hybridoma cells obtained in (2-3) producing monoclonal antibody against the protein of the present invention are intraperitoneally injected (5 to $20\times10^6$ cells per mouse) to 8 to 10-weeks old mice or nude mice which have been subjected to intraperitoneal administration of 0.5 ml pristane (2,6,10,14-tetramethylpentadecane), and have been bred for 2 weeks. The hybridomas form ascites carcinoma in 10 to 21 days.

The ascites is collected from each mouse having ascites tumor and then is subjected to centrifugation at 3000 rpm for 5 minutes to remove the solid material.

The monoclonal antibodies can be purified and prepared from the resulting supernatant by the same method as used for the preparation of polyclonal antibody.

Subtyping of antibody can be performed using a typing kit for mouse or rat monoclonal antibody. The quantity of protein can be calculated according to the Lowry method or by absorbance at 280 nm. 4. Method for detecting and quantifying mRNA encoding β-catenin nuclear localizing protein and method for diagnosing disease with altered protein expression due to mRNA level Messenger RNA of β-catenin nuclear localizing protein can be detected using DNAs encoding the β-catenin nuclear localizing protein, such as B9L DNA comprising the nucleotide sequence represented by SEQ ID NO: 1 or bc19 DNA; partial fragments of the DNA, for example, a fragment comprising 200 bp or more continuous nucleotides of the nucleotide sequence represented by SEQ ID NO: 1; or an oligonucleotide of the β-catenin nuclear localizing protein.

Methods for detecting mRNAs of β-catenin nuclear localizing proteins include northern blotting, in situ hybridization, quantitative PCR, differential hybridization, DNA chip, RNase protection assay, and the like. It is possible to examine the expression level of B9L protein in tissues or cells at the mRNA level according to these methods.

The above methods can be used to examine which tissue or cell types express β-catenin nuclear localizing proteins, and what kind of stimulus leads to changes in the expression level within cells.

Samples to be used in the method include biological samples such as organs, tissues or blood that are collected from human or animals, or primary culture cells or cell lines that are established from these biological samples.

Northern blotting is a method wherein. total RNA or mRNA is extracted from sample (hereinafter referred to as "sample-derived RNA"); separated by gel electrophoresis; transferred to a membrane, such as nylon filter; hybridization is conducted with a probe prepared from a DNA encoding β-catenin nuclear localizing protein, or a DNA or oligonucleotide comprising a partial sequence of the DNA by labeling with radioisotope, digoxigenin, biotin, or the like; then washed to detect mRNA encoding β-catenin nuclear localizing protein as a band to which the labeled probe has been specifically bound. The method can be performed based on the method and conditions described in "Molecular Cloning, Second Edition". The intensity of the band, i.e., the amount of bound labeled probe reflects the amount of mRNA of β-catenin nuclear localizing protein. Therefore, β-catenin nuclear localizing protein can be quantified at the mRNA expression level by detecting, on the same filter, mRNA band of constitutively expressed actin, G3PDH (glyceraldehydes 3-phosphate dehydrogenase), or the like, which expression level does not alter due to the kind of tissue or clinical condition, and using the intensity of the band for normalization. The size of mRNA of a β-catenin nuclear localizing protein can be determined by loading a set of labeled RNA molecular markers on the same gel in the electrophoresis, and comparing the migrated position of the band with the positions of the molecular markers.

In situ hybridization is a method wherein paraffin embedded slice or cryostat slice is prepared from a sample organ or tissue; hybridized with a labeled probe prepared from a DNA encoding β-catenin nuclear localizing protein, or a DNA or oligonucleotide comprising a partial sequence of the DNA; and then washed to detect cells or the site expressing the β-catenin nuclear localizing protein in detail. The method can be performed according to the method and conditions described in "Current Protocols in Molecular Biology".

Quantitative PCR (Delidow B. C. et al., Gene Anal. Tech. 6: 120 (1989)) is a method wherein PCR is performed using cDNA synthesized from sample-derived RNA using oligo-dT primer and reverse transcriptase (hereinafter referred to as sample-derived cDNA) as a template with oligonucleotide primers designed based on the nucleotide sequence of cDNA encoding β-catenin nuclear localizing protein to specifically amplify a DNA fragment derived from mRNA encoding the β-catenin nuclear localizing protein. The amount of the amplified DNA fragment reflects the amount of mRNA in the sample that encodes the β-catenin nuclear localizing protein. Thus, mRNA encoding β-catenin nuclear localizing protein can be quantified by using the result of PCR conducted for cDNA of actin, G3PDH (glyceraldehydes 3-phosphate dehydrogenase), or the like, which is constantly expressed among tissues regardless of the clinical conditions, as a control. The oligonucleotide primers are designed so as to specifically bind to a cDNA encoding the β-catenin nuclear localizing protein at an annealing temperature that does not permit hybridization between the primers or intraprimer hybridization, and to be released at a denaturation temperature. Quantification of the amplified DNA fragment must be done within numbers of PCR cycles wherein the amplified products are exponentially increasing. Such number of PCR cycles can be determined by performing PCR for a single sample with different numbers of cycles and analyzing the amount of the amplified DNA fragments with respect to the increase in the number by gel electrophoresis.

Differential hybridization (Lennon G. G. and Lehrach H., Trends Genet. 7: 314 (1991)) and DNA chip (Shalon D. et al., Genonie Res. 6: 639 (1996)) are methods wherein a DNA encoding β-catenin nuclear localizing protein, or a DNA or oligonucleotide comprising a partial sequence of the DNA is immobilized onto a matrix, such as filter, slide glass, and silicon; hybridization is performed with a labeled cDNA probe that is synthesized from sample-derived RNA using oligo-dT primers, labeled dNTP, and reverse transcriptase; and washing is performed to detect the changes in the expression level of the β-catenin nuclear localizing protein in a sample to be measured. In both methods, difference in the mRNA expression level of the β-catenin nuclear localizing protein between the sample to be measured and a control sample can be detected by immobilizing a DNA for actin or G3PDH onto a filter or matrix as an internal control. Furthermore, for accurate quantification, different labeled dNTP may be used for preparing the labeled cDNA probes from the sample to be measured and the control sample, and the two labeled cDNA probe may be simultaneously hybridized on a single filter or matrix.

In RNase protection assay (Pape M. E. et al., Genet. Anal. Tech. Appl. 8: 206 (1991)), first, a promoter sequence, such as T7 promoter and SP6 promoter, is ligated to the 3'-end of a DNA encoding β-catenin nuclear localizing protein; and then labeled antisense RNA of the β-catenin nuclear localizing protein is synthesized using in vitro transcription system with labeled NTP and promoter specific RNA polymerase. The labeled antisense RNA is hybridized with total RNA or mRNA prepared from the sample to allow formation of RNA-RNA hybrid with mRNA of the β-catenin nuclear localizing protein in the sample. Then, digested with ribonuclease, and bands protected from the digestion by the ribonuclease due to hybrid formation is detected by gel electrophoresis. The expression of the β-catenin nuclear localizing protein can be quantified at the mRNA level by quantifying the protected band.

The above methods can be used for diagnosing diseases wherein the mRNA expression level of β-catenin nuclear localizing protein is increased or decreased in patient compared to normal healthy subject by quantifying and comparing the expression of the β-catenin nuclear localizing protein at the mRNA level between biological samples, such as organ, tissue, and blood, that are collected by biopsy from subject and healthy normal subject (serving as control) or primary culture cells cultured from the samples.

Such diseases include cancers, for instance, colon cancer. In cancer such as colon cancer, the expression of β-catenin nuclear localizing protein increases, and enhances the localization of β-catenin into the nucleus and transcriptional activation by β-catenin/TCF complex which can be a cause of cell canceration. Therefore, the expression of β-catenin nuclear localizing protein is considered to be increased in some cancer cells, such as colon cancer cells, compared to normal cells. Thus, when the expression of β-catenin nuclear localizing protein is diagnosed to be increased by the above method, the subject may suffer cancer.

5. Method for Detecting Mutations in Gene Encoding β-Catenin Nuclear Localizing Protein, and Diagnostic Method for Diseases Having Mutations in the Gene The relationship between diseases, such as colon cancer, and the existence of a mutation in gene encoding β-catenin nuclear localizing protein can be evaluated using a DNA encoding the β-catenin nuclear localizing protein, or a DNA or oligonucleotide comprising a partial sequence of the DNA by comparing the nucleotide sequence of genomic DNA of the β-catenin nuclear localizing protein in a group of patients suffering the disease and a control group of normal healthy subjects, each group comprising 10 to 100 people.

Samples to be tested include genomic DNA extracted from biological samples such as organ, tissue, and blood, collected from human, or primary culture cells established from the samples; and cDNA prepared from total RNA or mRNA extracted from the samples (hereinafter referred to as sample DNA).

The existence of mutations can be detected by amplifying a DNA fragment using the sample DNA as a template with primers designed based on the nucleotide sequence of B9L DNA, determining the nucleotide sequence of the amplified DNA fragment, and comparing the determined sequence to that of normal B9L DNA.

Methods of screening for the presence of a disease-related mutation in the B9L gene include single strand conformation polymorphism (SSCP) analysis (Sheffield V. C. et al., Genomics 16: 325 (1993)), mismatch digestion and denaturing gradient gel electrophoresis.

SSCP analysis is a method wherein primers that enable amplification of B9L DNA fragments smaller than 200 bp are designed based on the nucleotide sequence of DNA encoding B9L protein; PCR is performed using sample-derived DNA as a template and the primers; denaturing the amplified DNA fragments; and conducting electrophoresis on a non-denaturing polyacrylamide gel. The amplified DNA fragments can be detected as a band by labeling a primer with radioisotope or fluorescent dye in PCR, or staining the amplified DNA fragments with silver. As the mobility in a non-denaturing gel shifts by the difference in the nucleotide sequence, a mutation can be detected by comparing the mobility of the amplified fragments of sample DNA to that of B9L DNA having a normal nucleotide sequence.

Mismatch digestion is a method wherein PCR is performed using sample DNA as a template with primers designed based on the nucleotide sequence of B9L DNA; hybridizing the amplified DNA fragments with a B9L DNA having a normal nucleotide sequence that is labeled with radioisotope or fluorescent dye; and treating the hybridized DNA with osmium tetraoxide or T4 phage endonuclease VII (Dean M., Nat. Genet. 9: 103 (1995)) to digest the DNA at mismatched sites. The method is one of the most sensitive methods for detecting mutations, and is applicable to sample DNAs consisting of kilobases.

Denaturing gradient gel electrophoresis (DGGF) (Fischer S. G. and Lerman L. S., Proc. Natl. Acad. Sci. USA 80: 1579 (1983); Cariello N. F. and Skopek T. R., Mutat. Res. 288: 103 (1993)) is a method wherein DNA fragments are amplified using sample DNA as a template with primers that are designed based on the nucleotide sequence of B9L DNA; and the amplified fragments are electrophoresed on a gel with a concentration gradient of a chemical denaturant or temperature gradient. The presence of a mutation can be detected through the mobility that shifts with the change in temperature or denaturant concentration when the denaturation of the DNA fragment occurs due to a mutation in the nucleotide sequence. Addition of poly (G:C) to the terminus of the primers increases the sensitivity of detection (Sheffield V. C. et al., Proc. Natl. Acad. Sci. USA 86: 232 (1989)).

Mutations detected by the above methods can be statistically analyzed according to the method described in "Handbook of Human Genetics Linkage", The John Hopkins University Press (1994) to identify single nucleotide polymorphisms (SNPs) linked to a disease.

Once a mutation is identified as being linked. to a disease such as cancer, such disease can be diagnosed by analyzing chromosomal DNA by southern hybridization with an oligonucleotide probe that can hybridize to the mutation site. Alternatively, diagnosis can be conducted by performing PCR with a oligonucleotide primer having a normal sequence corresponding to the mutation site in the disease at the 3' end, which utilizes the fact that the amplification by PCR does not occur unless the 3'-end is matched. Alternatively, diagnosis can be conducted through the nucleotide sequence analysis of the mutation site with B9L oligonucleotide sequence primers.

In addition, abnormality in B9L gene, such as deletion, change in the copy number, chromosome translocation, can be detected by performing southern hybridization on chromosomal DNA digested with appropriate restriction enzyme using a DNA encoding the B9L protein or a DNA comprising a partial nucleotide sequence of the DNA as a probe.

The protein truncation test (PTT) (van der Luijt R. et al., Genomics 20: 1 (1994)) is another method for screening a mutation in DNA. The method enables specific detection of frame shift mutations, which causes a stop codon in the middle of the translation frame resulting in truncation of a protein, mutation at splicing sites, nonsense mutation, and the like. In PTT, a particular primer wherein the T7 promoter sequence and eukaryotic translation initiation sequence are linked at the 5'-end of the nucleotide sequence of a DNA encoding B9L protein is designed to amplify cDNA fragments by RT-PCR from sample-derived RNA using the primer. mRNA is transcribed from the cDNA using in vitro transcription system that contains T7 RNA polymerase, and protein is produced from the mRNA using in vitro translation system. SDS-PAGE is conducted with the protein to compare its molecular size with that of the B9L protein translated from an mRNA of normal B9L protein. Thus, a mutation that causes deletion in the protein can be detected.

6. Determination of Chromosomal Location of Gene Encoding β-Catenin Nuclear Localizing Protein Chromosomal location of a gene encoding β-catenin nuclear localizing protein can be determined by methods such as radiation hybrid (Science 250: 245 (1990)) and in situ hybridization (Annals of Human Genetics 45: 135 (1981); Cell 52: 51 (1988)), using the DNA encoding the protein.

Radiation hybrid is a method wherein PCR is conducted against multiple DNA panels comprising human chromosome fragments (fragments assigned to a specific chromosomal location by analysis using chromosome markers), such as Gene-Bridge 4, to specifically amplify a gene encoding β-catenin nuclear localizing protein, and the amplification result is analyzed to determine detailed chromosomal location of the gene.

In in situ hybridization, human chromosome preparations are hybridized with a DNA encoding human B9L protein as a probe, and hybridized signal is detected to determine the location of the signal on the preparation. This method enables to determine not only the chromosome number that contains the gene of β-catenin nuclear localizing protein, but also the physical location on the chromosome. The probe may be labeled with radioisotope 3H or biotin so that the signal can be detected by autoradiography or avidin labeled with fluorescent dye fluorescein isothiocyanate (FITC), respectively.

Alternatively, instead of directly detecting the chromosomal location of the gene of β-catenin nuclear localizing protein as in the above methods, the STS (sequence-tagged site) database (containing information of primers that are derived from the nucleotide sequences of a variety of ESTs, chromosomal DNA fragments that are amplified by the primers, and chromosomal location of the fragments) can be searched for a sequence that is homologous to the nucleotide sequence of the DNA encoding the B9L protein. When an STS having an identical nucleotide sequence to a part of the DNA encoding β-catenin nuclear localizing protein is discovered, the STS is considered to be corresponding to the gene encoding the β-catenin nuclear localizing protein on the chromosome. Thus, the chromosomal location of the STS is presumed to be the location of the gene.

In addition, a nucleotide sequence of a human genomic DNA in databases is normally accompanied with information on its chromosomal location. For instance, human genomic DNA sequences with GenBank accession numbers AP000877 and AP000909, which comprise the exon of human B9L genomic DNA obtained in above section 1. (6-2), are described to be located on human chromosome 11q23 in the database. Therefore, human B9L gene is concluded to be located on human chromosome 11q23.

The bc19 gene has been reported to be located on human chromosome 1q21.

The information on the chromosomal location of genes encoding β-catenin nuclear localizing protein is useful for examining the. relationship between the genes and diseases. For example, identification of regions wherein LOH (loss of heterozygosity: a chromosome deletion found in one of the pair of a gene) is detected at high frequency in many cancers as a chromosomal region highly expected to contain a tumor suppressor gene is in progress (inactivation of a tumor suppressor gene is considered to occur through a mutation in the other pair of the tumor suppressor gene that is within the region with LOH, and leads to the onset of cancer) When the region coincides with the chromosomal location of the gene of β-catenin nuclear localizing protein, the protein may be involved in the onset of cancer which has LOH in this region. In such cases, when the association of the β-catenin nuclear localizing protein with the cancer is clarified by analyzing mutation in the gene or expression of the β-catenin nuclear localizing protein, then diagnosis and treatment of such cancer can be performed using a DNA encoding the β-catenin nuclear localizing protein, the β-catenin nuclear localizing protein, or an antibody recognizing the protein.

7. Treatment of Cancer by Inhibiting the Activity of β-Catenin Nuclear Localizing Protein In cancer cells that have mutation in APC gene or β-catenin gene such as colon cancer cells, β-catenin accumulates due to the defect in the regulation of β-catenin degradation, and the transcriptional activation by a β-catenin/TCF complex cannot be suppressed. This derepression may be associated with the onset of cancer. It is considered that the transcriptional activation by β-catenin/TCF complex can be suppressed through the suppression of transfer of accumulated β-catenin into the nucleus by inhibiting the β-catenin nuclear localizing function of β-catenin nuclear localizing protein or suppressing the expression of the β-catenin nuclear localizing protein. Substances having such functions may be used as therapeutic agents for cancer.

(1) Inhibitor of β-Catenin Nuclear Localizing Protein and Method of Screening for the Inhibitor An inhibitor of β-catenin nuclear localizing protein is defined as a substance that inhibits the nuclear localization of β-catenin through inhibiting the binding between the β-catenin nuclear localizing protein and β-catenin.

Such a substance that inhibits the binding between a β-catenin nuclear localizing protein and β-catenin can be screened by contacting the β-catenin nuclear localizing protein and β-catenin, and comparing the bound amount of β-catenin nuclear localizing protein and β-catenin in the presence and absence of a test compound.

For example, the amount of β-catenin bound to the β-catenin nuclear localizing protein can be estimated by mixing and binding the β-catenin nuclear localizing protein with β-catenin that is labeled with 35S or the like in the presence and absence of a test compound, isolating the β-catenin nuclear localizing protein using an antibody or the like, and measuring the amount of the labeled β-catenin in the isolated material. When the amount of bound β-catenin is decreased in the presence of a test compound compared to that in the absence, the compound is considered to be an inhibitor of the binding between β-catenin and the β-catenin nuclear localizing protein.

Whether such an inhibitor that inhibits the binding between β-catenin and a β-catenin nuclear localizing protein can block the nuclear localization of β-catenin can be examined by fixing cells that forcedly express both β-catenin and the β-catenin nuclear localizing protein to which cells a test compound has been added or without addition, and detecting β-catenin by immunostaining using an anti-β-catenin antibody. In this case, as normal β-catenin is degraded by GSK-3β in cells. By using a mutated β-catenin such as a mutant wherein the serine 33 is substituted with tyrosine, that has a mutation at a phosphorylation site, and the mutated, β-catenin accumulates without degradation. Therefore, the intracellular level of β-catenin increases and a detection of β-catenin becomes easy by using the mutated β-catenin. β-catenin itself does not have a particular intracellular localization tendency, and evenly distributes in cells upon forced expression of β-catenin alone. However, when a B9L/bc19 protein analogue has a β-catenin nuclear localizing function, larger amount of β-catenin is found in the nucleus compared to the cytoplasm.

β-catenin and β-catenin nuclear localizing protein used for the above screening may be purified from tissue or cells expressing the proteins. However, large quantity of these proteins can be obtained by culturing a transformant that is transformed with a DNA encoding the proteins, and purifying them according to standard methods. The screening of the present invention can also be performed using cultured cells expressing the proteins, or processed cultured cells. However, when intact cells are used, it is preferable to use cells that secrete the proteins. Herein, processed cultured cells include concentrates of the cells, dried materials of the cells, cells obtained by centrifugation of the culture supernatant, dried cells, freeze-dried cells, detergent treated cells, sonicated cells, mechanically crushed cells, solvent treated cells, enzyme treated cells, protein fractions of the cells, fixed cells, and enzyme preparations extracted from the cells.

(2) Method for Inhibiting the Expression of β-Catenin Nuclear Localizing Protein Methods for inhibiting the expression of a β-catenin nuclear localizing protein include: suppression of translation of the β-catenin nuclear localizing protein from mRNA by administering an antisense DNA or antisense oligonucleotide against the protein, or an antisense RNA expression vector; inhibition of transcription by administering an oligonucleotide that binds to the promoter of the gene of the β-catenin nuclear localizing protein to form a triple helix; degradation of mRNA of the β-catenin nuclear localizing protein by administering a ribozyme; and inhibition of transcription by administering a compound that specifically inhibits the transcription of the gene of β-catenin nuclear localizing protein.

8. Vector for Gene Therapy

For the treatment of diseases that are caused due to decreased expression levels of β-catenin nuclear localizing protein, the β-catenin nuclear localizing protein or a vector for gene therapy that produces the protein in human body can be administered.

Such vectors for gene therapy include recombinant virus vectors producing a β-catenin nuclear localizing protein. The recombinant virus vectors can be constructed by inserting the full-length cDNA of the human β-catenin nuclear localizing protein obtained according to the method described in section 1 downstream of a promoter in a virus vector. Alternatively, if necessary, a DNA fragment of a suitable size that comprises the region encoding the β-catenin nuclear localizing protein is prepared to insert the fragment downstream of a promoter in a virus vector. The recombinant virus vectors are defective in genes that encode proteins necessary for virus packaging. For example, retroviruses, such as mouse Moloney's leukemia virus, lack proteins, such as gag, pol, and env; lentiviruses, such as HIV, lack proteins, such as gag, pol, env, vpr, vpu, vif, tat, rev, and nef; adenoviruses lack proteins, such as E1A and E1B; and adeno-associated viruses lack proteins, such as Rep (p5, p19, p40) and Vp (Cap).

A recombinant virus vector is introduced into a suitable packaging cell. Any cells that can provide proteins required for virus packaging which are lost in the recombinant virus vector can be used for such a purpose, including, for example, HEK293 cells derived from human kidney, and mouse NIH 3T3 fibroblasts.

Any virus vector can be used so long as it can produce recombinant virus in the above packaging cells and contains a promoter at a position to enable transcription of a B9L gene in target cells. A plasmid vector such as MFG (Riviere I. et al., Proc. Natl. Acad. Sci. USA 92: 6733 (1995)), pBabepuro (Morgrnstern J. P. and Land H., Nucleic Acids Res. 18: 3587 (1990)), LL-CG, CL-CG, CS-CG, and CLG (Miyoshi H. et al., J. Virol. 72: 8150 (1998)), and pAdexl (Kanegae Y. et al., Nucleic Acids Res. 23: 3816 (1995)) can be used. Any promoter that can direct expression in human tissue can be used, including, for example, cytomegalovirus immediate early, (IE) gene promoter, SV40 early promoter, retrovirus LTR, metallothionein promoter, heat shock protein promoters, and the like. In addition, the enhancer of the cytomegalovirus IE gene may be used with the promoter.

The above recombinant virus vector can be introduced into the above packaging cells by the calcium phosphate method, lipofection (Feigner P. L. et al., Proc. Natl. Acad. Sci. USA 84: 7413 (1987)), and the like.

Alternatively, gene therapy without the use of a virus vector includes transfection method of therapeutic gene (US 5589466) wherein naked plasmid DNA is directly injected as a technique to directly transfer the DNA into desired tissue. Specifically, a β-catenin nuclear localizing protein can be expressed in tissue, such as colon cancer tissue, for which treatment is required by injecting an expression vector containing a DNA encoding the protein using a syringe or the like.

9. Method for Detecting and Determining β-Catenin Nuclear Localizing Protein Using Antibody Methods for detecting a β-catenin nuclear localizing protein by an antibody that immunologically recognizes the protein include immunohistochemistry such as tissue-immunostaining and immunocytochemistry; flow cytometry; western blotting; enzyme immunoassay (EIA) such as sandwich ELISA; and radioimmunoassay (RIA), which can be performed according to the literature ("Monoclonal Antibody Experiment Manual", edited by Sakuji Toyama and Tomie Yasu, Kodan-sha Scientific (1987); "Biochemical Experiment Seminar Series 5: Immunobiochemical Study", Tokyo-Kagaku Dojin (1986); Goding J. W., "Monoclonal Antibodies: Principles and Practice, Third edition", Academic Press (1996); Harlow E. and Lane D., Antibodies: A Laboratory Manual, Cold Spring Harbor Laboratory (1988)).

Immunohistochemistry is a method wherein tissue or cells are fixed; reacted with an antibody recognizing a β-catenin nuclear localizing protein followed by an anti-immunoglobulin antibody or fragment thereof that is labeled with fluorescent dye, enzyme, biotin, colloidal gold, radioisotope, or the like; then, if necessary, the labeled antibody is visualized; and the tissue or cells are examined under a microscope to detect the β-catenin nuclear localizing protein in the tissue or the cells. For fluorescent labeling, fluorescein isothiocyanate (FITC), tetramethylrhodamine isothiocyanate, or the like is used and are detected with a fluorescent microscope. For enzyme labeling, peroxidase, alkaline phosphatase, or the like is used, which can be detected by observing the specimen under a light microscope after the chromogenic reaction caused by the addition of a substrate allowing color to develop by the function of the enzyme. For biotin labeling, avidin that is conjugated with an enzyme such as peroxidase, is reacted, and then similar procedures used for enzyme-labeled antibody are performed. For colloidal gold labeling, the signal is detected by examining with an electron microscope. For radioisotope labeling, $^{125}I$ or the like may be used, and the detection can be conducted by coating with photosensitive emulsion and observing the silver grain developed by radiation with a light microscope.

Flow cytometry is a method wherein cells collected from a test subject are reacted with an antibody recognizing a β-catenin nuclear localizing protein followed by an anti-immunoglobulin antibody or fragment thereof that is labeled with a fluorescent dye such as FITC or phycoerythrin; and then the fluorochrome is measured on a flow cytometer to detect the expression of the β-catenin nuclear localizing protein in the cells.

Western blotting is a method wherein tissue sample or cells collected from a test subject, or homogenate thereof are separated by SDS-polyacrylamide gel electrophoresis; then blotted on a PVDF membrane or nitrocellulose membrane; reacting the membrane with an antibody recognizing a β-catenin nuclear localizing protein or a fragment thereof, followed by an anti-immunoglobulin antibody or fragment thereof that is labeled with an enzyme such as peroxidase or alkaline phosphatase, or radioisotope, such as 125I, to detect a band corresponding to the β-catenin nuclear localizing protein. When enzyme labeling is used, the detection is conducted by visualizing the band of the β-catenin nuclear localizing protein via the addition of a substrate that develops color through the reaction with the enzyme, or by autoradiography on an X-ray film via the addition of a substrate that emits light through the reaction with the enzyme. When radioisotope labeling is used, the band is detected by autoradiography on an X-ray film.

In sandwich ELISA, a variation of enzyme-linked immunoassays, two monoclonal antibodies with different antigen-recognition sites that recognize a β-catenin nuclear localizing protein are prepared, and then one of the monoclonal antibodies or fragment thereof is adsorbed on a plate and the other or fragment thereof is labeled with an enzyme, such as peroxidase or alkaline phosphatase. Cell homogenate is prepared from tissue or cells collected from a test subject and used as the test sample. The test sample is reacted with the antibody-adsorbed plate, the enzyme labeled anti-β-catenin nuclear localizing protein antibody or fragment thereof is reacted, a substrate that develops color by the enzyme is added to develop color, and the intensity of the color is measured on a spectrophotometer to detect or determine the β-catenin nuclear localizing protein in the sample.

Radioimmunoassay is a method wherein similar procedures as in enzyme immunoassay are carried out using an antibody labeled with radioisotope, such as $^{125}$I, instead of enzyme are used to detect or determine a β-catenin nuclear. localizing protein in the sample by measuring the radioactivity with a scintillation counter.

In addition to the above sandwich assay, competitive assay is known for enzyme immunoassays and radioimmunoassay, wherein a preparation of a β-catenin nuclear localizing protein, instead of antibody, is labeled; a proper amount of the labeled β-catenin nuclear localizing protein preparation and a test sample are reacted with an antibody recognizing the β-catenin nuclear localizing protein that is immobilized on a plate; and the enzyme activity or radioactivity on the plate is measured to detect or determine the β-catenin nuclear localizing protein in the sample.

10. Pharmaceutical Composition

The above β-catenin nuclear localizing protein, compounds, and antibodies can be administered alone as therapeutic agents. However, generally, it is preferably provided as a pharmaceutical compositions by mixing them with one or more pharmaceutically acceptable carriers, and formulating by any conventional method of pharmaceutics. The agent is preferably administered via the most efficient method for the treatment, including oral, administration and parenteral administration such as intraoral injection, intrarespiratory injection, intrarectal injection, subcutaneous injection, intramuscular injection and intravenous injection. Formulation for administration includes spray, capsule, tablet, granule, syrup, emulsion, suppository, injection, ointment and taping.

Appropriate formulations for oral. administration include emulsion, syrup, capsule, tablet, powder and granule. For example, liquid preparations, such as emulsion and syrup, may be prepared using water; sugars, such as sucrose, sorbitol and fructose; glycols such as polyethylene glycol and propylene glycol; oil such as sesame oil, olive oil and soybean oil; antiseptics such as β-hydroxybenzoate esters; flavors such as strawberry flavor and peppermint; and the like as additives. Capsules, tablets, powder, granules and the like may be prepared using excipients such as lactose, glucose, sucrose and mannitol; disintegrants such as starch and sodium arginate; lubricants such as magnesium stearate and talc; binding agents such as polyvinyl alcohol, hydroxypropyl cellulose and gelatin; detergents such as fatty acid esters; plasticizers such as glycerin; and the like as additives.

An appropriate formulation for parenteral administration includes injection, suppository and spray. For example, injection may be prepared using a carrier consisting of a salt solution, glucose solution, or mixture of both; and the like. Suppository may be prepared using a carrier, such as cacao butter, hydrogenated fat or carbonate. Spray may be prepared from the protein as such or by using a carrier that disperses the protein as fine particles to facilitate absorption, but which does not stimulate oral cavity or respiratory mucosa of the recipient. Specifically, example of such carrier includes lactose and glycerin. It is possible to prepare aerosol or dry powder depending on the characteristic of the protein and the used carrier. The components described above as additives for oral administration can be also added for parenteral agents.

Dosage and frequency of administration may vary depending on the desired therapeutic effect, method of administration, duration of treatment, age, body weight, and the like, but normally it is 10 μg/kg to 100 mg/kg per day for an adult.

BRIEF DESCRIPTION OF THE DRAWINGS

FIG. 1 shows the comparison of the amino acid sequences of mouse B9L (SEQ ID NO: 17) and human bcl9 (SEQ ID NO: 18). Amino acid sequences of mouse B9L (upper) and human bcl9 (lower) are represented in single letter notation. * denotes identical residues between human bcl9 and mouse B9L, and —indicates the absence of a corresponding residue. The β-catenin binding site is underlined, and sequence similar to the nuclear localization signal is double underlined.

BEST MODE FOR CARRYING OUT THE INVENTION

Figure 2:
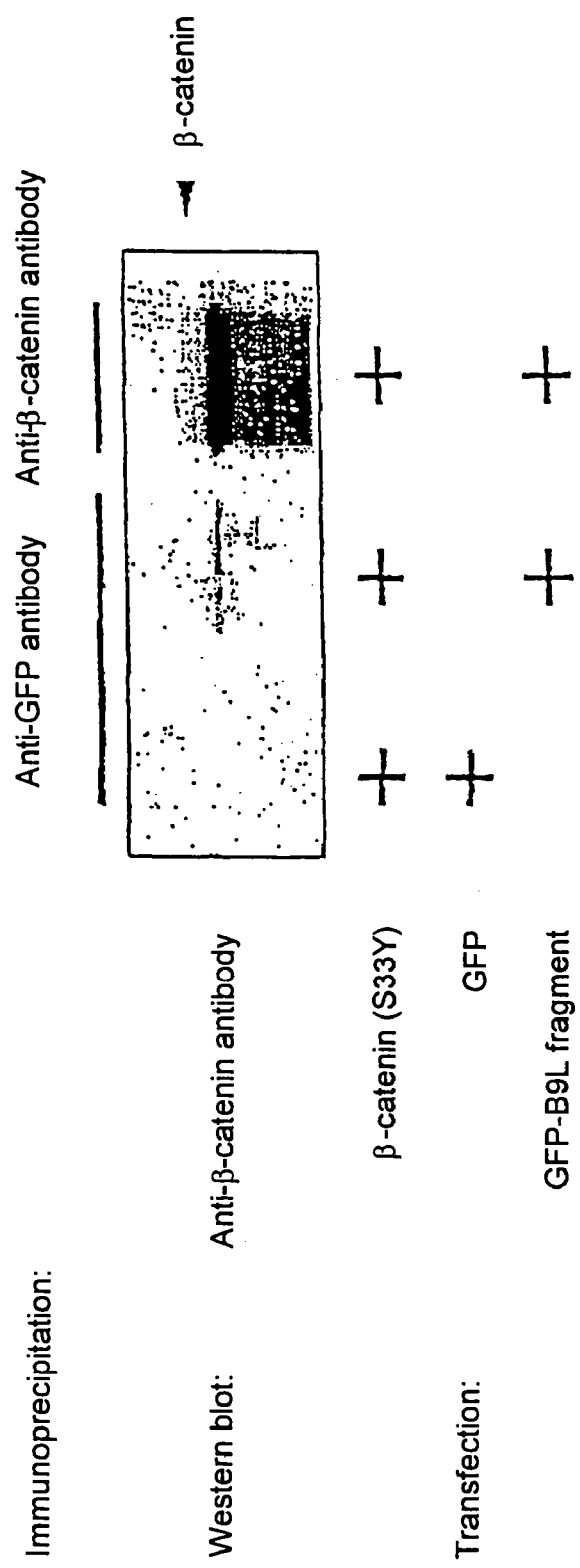
FIG. 2 shows the binding of β-catenin and B9L in cells. +under each lane indicates the expressed gene. Results of Western blotting using anti-β-catenin antibody as the primary antibody on immunoprecipitated cell lysates from COS-7 cells co-expressing β-catenin S33Y and GFP-B9L (center and right lanes), and β-catenin S33Y and GFP as a control (left lane) are shown. Antibodies used for immunoprecipitation are indicated on the top of each lane. Left and center: anti-GFP antibody; and right: anti-β-catenin antibody.

The present invention will be described below in detail with reference to Examples.

EXAMPLE 1

Cloning of B9L cDNA

A gene encoding a protein binding to mouse mβ-catenin arm was cloned by the yeast two-hybrid system.

(1) Preparation of Bait Plasmid for mβ-Catenin Arm

The nucleotide sequence of mouse β-catenin cDNA and the amino acid sequence of mouse β-catenin encoded by the cDNA are publicly known (GenBank accession No: M90364; Science 257: 1142 (1992)). Mouse β-catenin contains a repetitive sequence, which is called armadillo domain (mβ-catenin arm) in the region of residues 128 to 683 in its amino acid sequence. A DNA fragment of mouse β-catenin encoding this portion of mβ-catenin arm was amplified and isolated by PCR using cDNA from mouse cells as a template. The PCR primers were designed based on the nucleotide sequence of the portion of the cDNA encoding the above-mentioned mβ-catenin arm. The amplified DNA fragment was sequenced to confirm that it encodes mβ-catenin arm, and then the fragment was inserted into a vector pGBT9 (Clontech) between BamHI/SalI sites to prepare a plasmid for the expression of GAL4-β-catenin fusion protein in which β-catenin is fused with GAL4 BD.

(2) Screening Using the Two-Hybrid System

Screening was carried out with MATCHMAKER mouse fetal (Swiss Webster/NIH mouse; 17-day embryo) cDNA library, which is a library to be used for the two-hybrid system and provided by Clontech. This cDNA library contains vector pGAD10 (Clontech) with cDNA insert and, as a selection marker, LEU2 gene involved in leucine biosynthesis in yeast, and can express fusion proteins of GAL4 AD and cDNA-encoding proteins through ADH1 promoter. Specific method for the screening was conducted according to the manual attached to the library from Clontech as follows.

Specifically, both mouse fetal cDNA library for the two-hybrid system and plasmid GAL4-β-catenin prepared in (1) were introduced in yeast *Saccharomyces cerevisiae* HF7C strain (Clontech). HF7C strain is a yeast strain that is tryptophan-, leucine-, and histidine-auxotrophic. The strain has HIS3 gene on the chromosome wherein the gene is involved in histidine biosynthesis and has been ligated downstream of GAL1 promoter to which GAL4 BD can bind, as well as *E. coli*-derived β-galactosidase gene lacZ ligated downstream of a nucleotide sequence to which GAL4 BD can bind as reporter genes (Gene 212: 197 (1998)). A transformant containing both plasmid GAL4-β-catenin and cDNA clone of a protein that binds to mβ-catenin arm and expresses the respective fusion proteins, is non-auxotrophic for histidine and is positive in β-galactosidase activity. It is due to the fact that GaL4 BD and GAL4 AD come close to each other by the binding of mβ-catenin arm and to activate the transcription of HIS3 gene and lacZ gene in downstream of the nucleotide sequence to which GAL4 BD binds. Finally, a colony, indicating positive for β-galactosidase activity, was selected by growing $1.2 \times 10^6$ transformants on a medium without leucine, histidine, and tryptophan.

Plasmid DNA was recovered from the clone (selected colony), and the nucleotide sequence of the inserted cDNA fragment was determined as represented by SEQ ID NO: 3. Homology search for the nucleotide sequence was performed in the nucleotide sequence databases, and several mouse ESTs were found to be identical to the sequence. However, known gene with identical nucleotide sequence could not be found. Therefore, the above cDNA fragment isolated by the two-hybrid system was revealed to have a novel nucleotide sequence that encodes a protein binding to mouse □-catenin. The amino acid sequence of the protein encoded by the cDNA fragment is represented by SEQ ID NO: 4. The cDNA fragment comprising the nucleotide sequence represented by SEQ ID NO: 3 lacks a stop codon and the entire sequence encodes a protein; thus it was considered to be a part of full-length cDNA. The full-length cDNA was expected to contain extended sequences on both 5' and 3' ends of the nucleotide sequence represented by SEQ ID NO: 3. Thus, 5'-RACE and 3'-RACE were performed to amplify cDNA fragments containing nucleotide sequences further extending to the 5' and 3' directions, respectively, and their sequences were determined. By assembling the nucleotides sequence of the cDNA clone obtained by the two-hybrid system and those by 5'- and 3'-PACE, the nucleotide sequence represented by SEQ ID NO: 1 was obtained. The nucleotide sequence encodes a protein consisting of 1494 amino acids represented by SEQ SEQ ID NO: 2. The nucleotide sequence of the cDNA fragment isolated by the two-hybrid system corresponds to the nucleotides 733 to 1692 in the nucleotide sequence represented by SEQ ID NO: 1, and the amino acid sequence encoded by the cDNA fragment corresponds to the residues 245 to 564 in the amino acid sequence represented by SEQ ID NO: 2. This amino acid sequence was used for homology search against the amino acid sequence database in NCBI (National Center for Biotechnology Information) with the BLAST2 homology analysis program. As shown in FIG. 1, the sequence showed an overall homology of 37% to the bcl9 protein (Accession number CAA73942; Willis T. G. et al., Blood 91: 1871 (1998)). Thus, the □-catenin binding protein comprising the amino acid sequence represented by SEQ ID NO: 2 was dubbed B9L protein (bcl9 like protein). The above bcl9 protein is derived from human and the amino acid sequence of mouse bcl9 protein is not identified yet. However, there are a couple of EST clones (Accession numbers AI550007, and AI426858) in the GenBank nucleotide sequence database that are considered as the nucleotide sequence of a cDNA encoding mouse bcl9 protein, which nucleotide sequence of the clones exhibit a homology of 90% or more to the human bcl9 protein (the homology of the nucleotide sequence corresponding to that of B9L protein is 40% or lower). Thus, the obtained mouse B9L protein seems not to be the mouse bcl9 protein. The B9L protein is a proline-rich protein like the bcl9 protein, and contains a sequence similar to the nuclear localization signal.

By northern blot hybridization using the above cDNA as a probe against mRNA prepared from mouse embryo (day-13.5), an mRNA band of 7.5 kb was detected.

(3) Human B9L Gene and its Chromosomal Location

Nucleotide sequences of human DNAs having homology to the nucleotide sequence of mouse B9L cDNA obtained in (2) was searched in nucleotide sequence databases including GenBank using homology search programs such as BLAST. As a result, human EST clones (GenBank accession numbers U46365 and R24762) that were predicted to be derived from human B9L cDNA, and working draft sequences of human genomic DNA (GenBank accession numbers AP000877, AP002357, and AP000909) comprising an exon sequence of human B9L genomic DNA were identified. These working draft sequences were compared with the nucleotide sequences of mouse B9L cDNA and human ESTs to obtain sequences of exons encoding human B9L as represented by SEQ ID NOs: 5 to 8. SEQ ID NOs: 5 to 8 are exons corresponding to the nucleotides 27 to 412, 413 to 532, 1183 to 3115, and 3116 to 3397, respectively, in the sequence of mouse B9L cDNA (SEQ ID NO: 1). SEQ ID NO: 9 represents a partial nucleotide sequence of human B9L cDNA derived from SEQ ID NOs: 5 and 6 (corresponding to the nucleotides 27 to 532 in the nucleotide sequence of mouse B9L cDNA represented by SEQ ID NO: 1). SEQ ID NO: 10 represents a partial amino acid sequence of human B9L protein encoded by the nucleotide sequence represented by SEQ ID NO: 9 (corresponding to the residues 10 to 177 in the amino acid sequence of mouse B9L protein represented by SEQ ID NO: 2). SEQ ID NO: 11 represents a partial nucleotide sequence of human B9L cDNA derived from SEQ ID NOs: 7 and 8 (corresponding to the nucleotides 1183 to 3397 in the sequence of mouse B9L cDNA represented by SEQ ID NO: 1). SEQ ID NO: 12 represents a partial amino acid sequence of human B9L protein encoded by the nucleotide sequence represented by SEQ ID NO: 11 (corresponding to the residues 395 to 1132 in the amino acid sequence of mouse B9L protein represented by SEQ ID NO: 2).

AP000877 and AP000909 were described to be located on human chromosome 11q23 in the database. Thus, human B9L gene was considered to be located on human chromosome 11q23.

EXAMPLE 2

Binding of B9L Protein and β-Catenin In Vitro

Direct binding of B9L protein and β-catenin was confirmed as follows. Protein consisting of the amino acid sequence of SEQ ID NO: 4, encoded by the B9L cDNA fragment obtained by the two-hybrid screening described in Example 1 was used in Examples 2 to 5 as B9L protein.

$^{35}$S-labeled B9L protein was synthesized from the B9L cDNA fragment obtained by the two-hybrid method of Example 1 by in vitro transcription and translation using $^{35}$S-labeled methionine and TNT®-coupled reticulocyte lysate system (Promega). E. coli transformed with GST-β-catenin fusion protein (hereinafter abbreviated as GST-β-catenin).expression plasmid (Nakamura et al., Genes to Cells 3: 395 (1998)) wherein mouse β-catenin DNA was inserted into the cloning site of E. coli glutathione-S-transferase (GST) expression plasmid vector pGEX5X-1 (Amersham Pharmacia Biotech), and pGEX5X-1, as a control, were cultured to prepare bacterial lysates, respectively. Glutathione-Sepharose 4B (Amersham Pharmacia Biotech) was added to the lysates to isolate GST-β-catenin or GST by adsorption. The glutathione-Sepharose 4B to which GST-β-catenin or GST had been adsorbed was reacted with the above $^{35}$S-labeled B9L protein in buffer A (10 mM Tris-HCl (pH 8.0), 140 mM NaCl, 1 mM EGTA, 10 μg/ml leupeptin, 10 μg/ml aprotinin) containing 0.1% Triton X-100 at 4° C. for 2 hr. The glutathione-Sepharose 4B was washed well with buffer A, and then SDS-PAGE sample buffer was added to elute bound proteins into the sample buffer. The eluate and $^{35}$S-labeled B9L protein were used as a sample for SDS-PAGE, and then subjected to autoradiography. The result showed that a band corresponding to the $^{35}$S-labeled B9L protein was detected in E. coli expressing GST-β-catenin, whereas no band was detected in E. coli expressing GST. Therefore, it was confirmed that the B9L protein directly binds to GST-β-catenin in vitro and that the site responsible for the binding with the B9L protein is located within the β-catenin moiety of the GST-β-catenin.

EXAMPLE 3

Binding of B9L Protein and β-Catenin in Animal Cells

The B9L cDNA fragment obtained in Example 1 was inserted into pEGFP-C2, green fluorescent protein (GFP) expression vector (Clontech), to construct an expression plasmid for GFP-B9L fusion protein (hereinafter abbreviated as GFP-B9L). Mutated mouse β-catenin S33Y cDNA wherein serine 33, the target site of GSK-3β-mediated phosphorylation, is substituted with tyrosine was subcloned into animal cell expression plasmid vector pMKITneo (Nakamura et al., Genes to cells 3: 395 (1998)) to construct an expression plasmid for S33Y β-catenin. These plasmids were transfected using LipofectAMINE (Life Technologies) into monkey kidney cell line COS-7 cells (ATCC: CRL-1651) for forced expression. After 24 hr, the cells were harvested to prepare cell lysates by adding buffer A containing 1% Triton X-100. The cell lysates were reacted with anti-GFP antibody or anti-β-catenin antibody at 4° C. for 1 hr to form an immune complex between GFP-B9L or S33Y β-catenin and the respective antibody, and then Protein G-Sepharose 4B (Amersham Pharmacia Biotech), which is capable of binding to IgG, was added to the reaction solution to adsorb the immune complex. The Protein G-Sepharose 4B was washed well with lysis buffer A, and SDS-PAGE sample buffer was added to elute the immune complex. SDS-PAGE was conducted using the eluate as a sample, transferred onto polyvinylidene fluoride (PVDF) membrane, Immobilon-P (Millipore), and S33Y β-catenin was detect by Western blotting using anti-β-catenin antibody (Transduction Laboratory, raised in mice) and alkaline phosphatase-labeled anti-mouse IgG antibody as primary and secondary antibodies, respectively. As shown in FIG. 2, a band was detected with anti-β-catenin antibody in the immunoprecipitate obtained using anti-GFP antibody, which was used to precipitate GFP-B9L. Thus, the result confirmed that GFP-B9L is bounds to β-catenin in cells as well.

EXAMPLE 4

Effect of B9L Protein on Subcellular Localization of β-Catenin

The plasmids for the expression of GFP-B9L and S33Y β-catenin constructed in Example 3 were transfected alone or together into mouse NIH 3T3 cells using Effectene (QIAGEN), and were forcedly expressed. GFP expression vector pEGFP-C2, as a control, was also transfected into mouse NIH 3T3 cells and was forcedly expressed. After 24 hours, the cells were fixed with formaldehyde, stained with anti-β-catenin antibody, reacted with rhodamine isothiocyanate (RITC)-labeled anti-rabbit IgG antibody, and observed by fluorescence microscopy to detect S33Y β-catenin in the cell. GFP-B9L was directly detected by observation of GFP under fluorescence microscopy (with the use of-FITC filter).

The result revealed that S33Y β-catenin was evenly distributed in the cytoplasm and the nucleus within cells expressing only S33Y β-catenin, whereas both S33Y β-catenin and GFP-B9L were localized in the nucleus in cells expressing both proteins. Thus, it was indicated that the B9L protein has a characteristic to bind to β-catenin to localize β-catenin into the nucleus. GFP-B9L was also localized to the nucleus by the expression of GFP-B9L alone. Due to the fact that, when GFP was expressed alone, GFP evenly distributed in the cytoplasm and nucleus, the nuclear localization of GFP-B9L was confirmed to be independent to the attached GFP and depends on the presence of the B9L protein.

The full-length B9L cDNA obtained in Example 1 was inserted into the ECORI-SalI site of pEGFP-C2 to prepare plasmid pEGFP-C2B9L for the expression in animal cells, cotransfected with S33Y β-catenin expression plasmid into mouse 3T3 cells and the plasmids were forcedly expressed as described above, and S33Y β-catenin was. detected in the cells. Similar to theB9L protein fragment obtained by the two hybrid system, both S33Y β-catenin and GFP-B9L (full-length) were localized in the nucleus. Thus, the full-length B9L protein was also confirmed to bind to β-catenin and localizes β-catenin into the nucleus.

EXAMPLE 5

Binding Form of B9L Protein and β-Catenin (1) Binding Region in β-Catenin

As described in Example 1, the B9L protein was obtained as a protein binding to the armadillo domain of β-catenin (β-catenin arm) To determine which region of the β-catenin arm binds to the B9L protein, partial fragments of the β-catenin arm were expressed as described below, and the binding of the respective β-catenin fragments to the B9L protein was examined. The bait plasmid encoding the β-catenin arm prepared in Example 1 was used as a template for PCR to amplify DNA encoding (a) almost the entire β-catenin arm (corresponding to residues 141 to 664 in the amino acid sequence of mouse β-catenin); (b) N-terminal half of the β-catenin arm (corresponding to residues 141 to 390 in the amino acid sequence of mouse β-catenin, i.e., armadillo repeats 1-6); and (c) C-terminal half of the β-catenin arm (corresponding to residues 391 to 664 in the amino acid sequence of mouse β-catenin, i.e., armadillo repeats 7-12) using a pair of sense and antisense primers represented by SEQ ID NOs: 13 and 16; 13 and 14; and 15 and 16, respectively. The amplified products were inserted into pGBT9 vector to prepared respective bait plasmids.

The respective bait plasmids were cotransfected with the B9L cDNA fragment-expressing clone obtained by the two-hybrid system in Example 1 into yeast HF7C strain, and the binding between the B9L protein and the respective β-catenin partial fragments were examined by the existence of β-galactosidase activity in the transformants. The result showed that the almost entire region and the N-terminal half (armadillo repeats 1-6) of the β-catenin arm were able to bind to the B9L protein but no binding could be detected for the C-terminal half of the β-catenin arm (armadillo repeats 7-12). Thus, it was considered that the B9L protein binds to the N-terminal region of β-catenin arm (armadillo repeats 1-6).

(2) Binding Region in B9L Protein

As described in Example 1, the B9L protein was suggested to bind to the β-catenin arm through the region of residues 245 to 564 in its amino acid sequence, due to the fact that a protein having the residues 245 to 564 in the amino acid sequence of the B9L protein represented by SEQ ID NO: 2 was isolated as a protein that binds to the β-catenin arm. In order to further examine which region of the B9L protein binds to the β-catenin arm, two-hybrid system was performed as follows. DNA fragments encoding residues 245-291, 292-439, 440-564, 245-439, and 292-564, respectively, in the amino acid sequence of the B9L protein represented by SEQ ID NO: 2 were amplified by PCR, and inserted into the pGAD424 vector (Clontech) to prepared expression plasmids for the two-hybrid system which express the respective B9L partial fragments as a fusion protein with GAL4 AD. Each plasmid was cotransfected with the β-catenin arm bait plasmid prepared in Example 1 into yeast HF7C strain, and the binding of each B9L protein partial fragment and β-catenin arm was examined based on the presence or absence of β-galactosidase activity in the transformants. The result showed that the B9L protein fragments comprising residues 292-439, 245-439, or 292-564 in the amino acid sequence represented by SEQ ID NO: 2 was capable of binding to the β-catenin arm, whereas no binding could be detected for the fragment of residues 245-291 or 440-564, which lacks residues 292-439. Thus, the B9L protein was indicated to bind to the β-catenin arm at the region of residues 292-439 in the amino acid sequence represented by SEQ ID NO: 2.

EXAMPLE 6

Binding Actvity of bc19 Protein and β-catenin

The region determined to be the binding region with β-catenin in Example 5, residues 292-439 in the amino acid sequence of the B9L protein represented by SEQ ID NO: 2, corresponds to the residues 244-410 of protein bc19 which is homologous to B9L protein. Whether this region of the bc19 protein has the activity to bind to β-catenin was tested using similar method as described in Example 5.

Specifically, DNA fragment encoding the residues 244-410 in the amino acid sequence of human bc19 protein was amplified by PCR, and inserted into pGAD424 vector (Clontech) to prepaerd an expression plasmid for two-hybrid system which expresses the partial fragment (244-410) of the bc19 protein as a fusion protein with GAL4 Ad. The plasmid was cotransfected with the β-catenin arm bait plasmid prepared in Example 1 into yeast HF7C strain. β-galactosidase activity was confirmed in the resulting transformant. Thus, the bc19 protein was revealed to bind to β-catenin at the region of residues 244-410 in the amino acid sequence. The bc19 protein has a sequence resembling the nuclear localization signal, and thus the protein was also predicted to bind to β-catenin and has the activity to localize β-catenin into the nucleus. Therefore, the bc19 protein, DNAs encoding the bc19 protein, antibodies recognizing the bc19 protein, and oligonucleotides comprising a partial nucleotide sequence of a DNA encoding the bc19 protein can be used for similar purposes as the B9L protein, DNAs encoding the B9L protein, antibodies recognizing the B9L protein, and oligonucleotides comprising a partial nucleotide sequence of a DNA encoding the B9L protein. The bc19 protein is reported to be expressed abnormally high in CEMO-1 cell line, which was established from a patient with precursor-B-cell acute lymphoblastic leukemia (Willis T. G. et al., Blood 91: 1871 (1998)). This supports the hypothesis that the bc19 protein is involved in tumor development by enhancing the transcriptional activation by β-catenin/TCF complex through localizing β-catenin into the nucleus like the B9L protein.

INDUSTRIAL APPLICABILITY

The present invention provides novel β-catenin nuclear localizing protein and DNA encoding the protein. The use of the β-catenin nuclear localizing protein and DNA encoding the protein enables development of diagnostic and therapeutic agents for diseases, such as cancer, relating to nuclear localization of β-catenin.

"Sequence List free text"

SEQ ID NO: 13, Description of artificial sequence: sense primer for armadillo repeat 1 (downstream of Asn141) of mouse β-catenin comprising the MunI recognition site at the 5'-terminus.

SEQ ID NO: 14, Description of artificial sequence: antisense primer for armadillo repeat 6 (upstream of Asp390) of mouse β-catenin comprising the SalI recognition site at the 5'-terminus.

SEQ ID NO: 15, Description of artificial sequence: sense primer for armadillo repeat 7 (downstream of Ala391) of mouse, β-catenin comprising the MunI recognition site at the 5'-terminus.

SEQ ID NO: 16, Description of artificial sequence: antisense primer for armadillo repeat 12 (upstream of Glu664) of mouse β-catenin comprising the SalI recognition site at the 5'-terminus.

The invention claimed is:

1. An isolated DNA selected from the group consisting of:
   a) an isolated DNA encoding a polypeptide comprising the amino acid sequence of SEQ ID NO: 10;
   b) an isolated DNA encoding a polypeptide comprising the amino acid sequences of SEQ ID NOs: 10 and 12;
   c) an isolated DNA encoding a polypeptide comprising the amino acid sequence of SEQ ID NO: 10, wherein one to five amino acids are added, deleted, or substituted in the amino acid sequence; and
   d) an isolated DNA encoding a polypeptide comprising the amino acid sequences of SEQ ID NOs: 10 and 12, wherein one to five amino acids are added, deleted, or substituted in each of the amino acid sequences,
   wherein said polypeptide binds to a β-catenin and has an activity to localize the β-catenin into the nucleus.

2. The isolated DNA according to claim 1, which is selected from the group consisting of:
   a) the DNA comprising the nucleotide sequence of SEQ ID NO: 9;
   b) the DNA comprising the nucleotide sequences of SEQ ID NOs: 9 and 11,
   c) the DNA comprising the nucleotide sequence having 98% or more identity to the nucleotide sequence of SEQ ID NO: 9; and
   d) the DNA comprising the nucleotide sequences having 98% or more identity to the nucleotide sequences of SEQ ID NOs: 9 and 11, respectively,
   wherein said DNA encodes a polypeptide which binds to a β-catenin and has an activity to localize the β-catenin into the nucleus.

3. A recombinant DNA obtainable by inserting the DNA according to claim 1 or 2 into a vector.

4. A transformant obtainable by introducing the recombinant DNA according to claim 3 into a host cell.

5. A process of producing a polypeptide selected from the group consisting of:
   a) a polypeptide comprising the amino acid sequence of SEQ ID NO: 10;
   b) a polypeptide comprising the amino acid sequences of SEQ ID NOs: 10 and 12;
   c) a polypeptide comprising the amino acid sequence of SEQ ID NO: 10, wherein one to five amino acids are added, deleted, or substituted in the amino acid sequence;
   d) a polypeptide comprising the amino acid sequences of SEQ ID NOs: 10 and 12, wherein one to five amino acids are added, deleted, or substituted in the amino acid sequences, respectively,
   wherein said polypeptide binds to a 13-catenin and has an activity to localize the β-catenin into the nucleus,
   which comprises the steps of:
   i) culturing the transformant of claim 4 in a culture medium;
   ii) producing and accumulating the polypeptide in the culture; and
   iii) recovering the polypeptide from the culture.

6. The DNA according to claim 1 or 2 further comprising a pharmaceutical excipient.

* * * * *

UNITED STATES PATENT AND TRADEMARK OFFICE
CERTIFICATE OF CORRECTION

| | | |
|---|---|---|
| PATENT NO. | : 7,358,348 B2 | Page 1 of 1 |
| APPLICATION NO. | : 10/381247 | |
| DATED | : April 15, 2008 | |
| INVENTOR(S) | : Tetsu Akiyama and Shungo Adachi | |

It is certified that error appears in the above-identified patent and that said Letters Patent is hereby corrected as shown below:

On the Title Page, Item 54 should read
-- (54) β-CATENIN NUCLEAR LOCALIZING PROTEIN --.

Signed and Sealed this

Fifth Day of August, 2008

JON W. DUDAS
*Director of the United States Patent and Trademark Office*

UNITED STATES PATENT AND TRADEMARK OFFICE
CERTIFICATE OF CORRECTION

PATENT NO.         : 7,358,348 B2
APPLICATION NO. : 10/381247
DATED                  : April 15, 2008
INVENTOR(S)       : Tetsu Akiyama and Shungo Adachi It is certified that error appears in the above-identified patent and that said Letters Patent is hereby corrected as shown below:

On the Title Page, Item 54 and Column 1, lines 1 and 2, should read
-- (54) $\beta$-CATENIN NUCLEAR LOCALIZING PROTEIN --.

This certificate supersedes the Certificate of Correction issued August 5, 2008.

Signed and Sealed this

Twenty-sixth Day of August, 2008

JON W. DUDAS
*Director of the United States Patent and Trademark Office*

SEQUENCE LISTING

<160> NUMBER OF SEQ ID NOS: 18

<210> SEQ ID NO 1

<211> LENGTH: 4482
<212> TYPE: DNA
<213> ORGANISM: Mus musculus
<220> FEATURE:
<221> NAME/KEY: CDS
<222> LOCATION: (1)..(4482)

<400> SEQUENCE: 1

```
atg agg atc ctg gct aac aag aca agg tta ccc cac ccc agg agg aga      48
Met Arg Ile Leu Ala Asn Lys Thr Arg Leu Pro His Pro Arg Arg Arg
 1               5                  10                  15 gag gct cca ggg agt cca ccg ctg tcc cct cgg ggc cac tgc ccc cct      96
Glu Ala Pro Gly Ser Pro Pro Leu Ser Pro Arg Gly His Cys Pro Pro
            20                  25                  30 gcc cca gcc aag cca atg cac cca gaa aat aaa ctg acc aat cat ggc     144
Ala Pro Ala Lys Pro Met His Pro Glu Asn Lys Leu Thr Asn His Gly
        35                  40                  45 aag aca ggg aat gga ggg gcc caa tcc cag cac cag aat gtg aac caa     192
Lys Thr Gly Asn Gly Gly Ala Gln Ser Gln His Gln Asn Val Asn Gln
 50                  55                  60 gga ccc acc tgc aac ctg ggc tcc aag ggc gtg ggg gcg ggg agc cat     240
Gly Pro Thr Cys Asn Leu Gly Ser Lys Gly Val Gly Ala Gly Ser His
 65                  70                  75                  80 ggg gcc aag gcc aac cag atc tca cct agc aac tca agt ctg aag aac     288
Gly Ala Lys Ala Asn Gln Ile Ser Pro Ser Asn Ser Ser Leu Lys Asn
                85                  90                  95 ccc cag gca gga gtg tct cct ttc agc tca ctc aag ggc aag gtg aag     336
Pro Gln Ala Gly Val Ser Pro Phe Ser Ser Leu Lys Gly Lys Val Lys
            100                 105                 110 cgc gag agg agt gtg tct gtg gac tct gga gag cag cgg gaa gct ggg     384
Arg Glu Arg Ser Val Ser Val Asp Ser Gly Glu Gln Arg Glu Ala Gly
        115                 120                 125 act cca tcc ctc gat tca gag gcc aaa gag gtg gca ccc cgg agt aaa     432
Thr Pro Ser Leu Asp Ser Glu Ala Lys Glu Val Ala Pro Arg Ser Lys
    130                 135                 140 cgg agg tgt gtg ctg gag cgg aag cag ccg tac agt ggg gac gaa tgg     480
Arg Arg Cys Val Leu Glu Arg Lys Gln Pro Tyr Ser Gly Asp Glu Trp
145                 150                 155                 160 tgc tct ggg cca gac agc gag gag gac gac aag ccc att gcg gcc gcc     528
Cys Ser Gly Pro Asp Ser Glu Glu Asp Asp Lys Pro Ile Ala Ala Ala
                165                 170                 175 cac aat tgt aat gta gca gac cca gcc atg gtg acc cca cag ttg ggt     576
His Asn Cys Asn Val Ala Asp Pro Ala Met Val Thr Pro Gln Leu Gly
            180                 185                 190 cct ggc caa act gcc caa ctg ccc ctc agt gag agc agt gca cca ggc     624
Pro Gly Gln Thr Ala Gln Leu Pro Leu Ser Glu Ser Ser Ala Pro Gly
        195                 200                 205 ccc caa cat ggc ccc cag cca ggc ctt cgg cca gac gtt cct ggg ggt     672
Pro Gln His Gly Pro Gln Pro Gly Leu Arg Pro Asp Val Pro Gly Gly
    210                 215                 220 ggg ggt ggg ggc gtc cca gga aag cct ccg tca cag ttc gtc tat gtc     720
Gly Gly Gly Gly Val Pro Gly Lys Pro Pro Ser Gln Phe Val Tyr Val
225                 230                 235                 240 ttc acc acc cat ctg gcc aac aca gcg gca gag gca gtg ctg cag ggc     768
Phe Thr Thr His Leu Ala Asn Thr Ala Ala Glu Ala Val Leu Gln Gly
                245                 250                 255 cgg gca gag tcc atc ctt gcc tac cac cag cag aat gtg cct cgg gcc     816
Arg Ala Glu Ser Ile Leu Ala Tyr His Gln Gln Asn Val Pro Arg Ala
            260                 265                 270 aag ctg gat cag gcc cct aaa gtg cca ccc acc cca gaa cca cta ccc     864
Lys Leu Asp Gln Ala Pro Lys Val Pro Pro Thr Pro Glu Pro Leu Pro
```

```
                 275                 280                 285
ctg aat acg cca tca gca ggt aca cca cag tcc cag cca cct cct ttg    912
Leu Asn Thr Pro Ser Ala Gly Thr Pro Gln Ser Gln Pro Pro Pro Leu
    290                 295                 300 cca ccg cca ccc cca gcc cct ggc agt gcc cct cct gct ctg ccc ccg    960
Pro Pro Pro Pro Pro Ala Pro Gly Ser Ala Pro Pro Ala Leu Pro Pro
305                 310                 315                 320 gag ggg cct cct gaa gac acc agt cag gac ctg gcc ccc aac tca gtg   1008
Glu Gly Pro Pro Glu Asp Thr Ser Gln Asp Leu Ala Pro Asn Ser Val
                325                 330                 335 gga gct gcc agt aca ggt ggt ggg act ggg ggt acc cac cct aac acc   1056
Gly Ala Ala Ser Thr Gly Gly Gly Thr Gly Gly Thr His Pro Asn Thr
            340                 345                 350 cca acg gct gcc acc gct aac aac cct ctg cct cct gga gga gac cct   1104
Pro Thr Ala Ala Thr Ala Asn Asn Pro Leu Pro Pro Gly Gly Asp Pro
        355                 360                 365 ggc agt gcc cct ggc tcc gcc cta ttg ggg gag gcc acg ccc acc gga   1152
Gly Ser Ala Pro Gly Ser Ala Leu Leu Gly Glu Ala Thr Pro Thr Gly
    370                 375                 380 aat ggg cag agg aac ctg gtg ggc tct gag ggc ctg tcc aaa gag cag   1200
Asn Gly Gln Arg Asn Leu Val Gly Ser Glu Gly Leu Ser Lys Glu Gln
385                 390                 395                 400 ctg gag cac cgg gag cgc tcc ctc cag aca ctg cgg gac atc gag agg   1248
Leu Glu His Arg Glu Arg Ser Leu Gln Thr Leu Arg Asp Ile Glu Arg
                405                 410                 415 ctg ctg ctc cgc agt ggg gag act gag ccc ttc ctc aag ggg ccc ccg   1296
Leu Leu Leu Arg Ser Gly Glu Thr Glu Pro Phe Leu Lys Gly Pro Pro
            420                 425                 430 gga gga gct ggt gag gga ggc cca ccg gca caa gcg ccc tct gct gct   1344
Gly Gly Ala Gly Glu Gly Gly Pro Pro Ala Gln Ala Pro Ser Ala Ala
        435                 440                 445 caa ccg cct ccc tcc gcc cct cct ggg ggg ctg aag aag tat gag gag   1392
Gln Pro Pro Pro Ser Ala Pro Pro Gly Gly Leu Lys Lys Tyr Glu Glu
    450                 455                 460 cct ctg cag tca atg atc tca cag aca cag agc cta gga ggt ccc cct   1440
Pro Leu Gln Ser Met Ile Ser Gln Thr Gln Ser Leu Gly Gly Pro Pro
465                 470                 475                 480 ctg gag cat gaa gtg ccg ggg cac cct cag ggt gga gac atg gga cag   1488
Leu Glu His Glu Val Pro Gly His Pro Gln Gly Gly Asp Met Gly Gln
                485                 490                 495 caa atg aac atg atg atg cag agg ctg ggc cag gac agt ctg acg ccc   1536
Gln Met Asn Met Met Met Gln Arg Leu Gly Gln Asp Ser Leu Thr Pro
            500                 505                 510 gag cag gtg gcc tgg cgc aaa ctg cag gaa gag tac tac gag gag aag   1584
Glu Gln Val Ala Trp Arg Lys Leu Gln Glu Glu Tyr Tyr Glu Glu Lys
        515                 520                 525 cgg cgg aaa gag gag cag att gga ttg cac gga ggc cgc cct ctg cag   1632
Arg Arg Lys Glu Glu Gln Ile Gly Leu His Gly Gly Arg Pro Leu Gln
    530                 535                 540 gac atg gtg gga atg ggg ggt atg atg ggg agg ggg ccc cca cct cct   1680
Asp Met Val Gly Met Gly Gly Met Met Gly Arg Gly Pro Pro Pro Pro
545                 550                 555                 560 tac cac agc aaa cct ggg gat cag tgt gca cct gga atg ggt gca caa   1728
Tyr His Ser Lys Pro Gly Asp Gln Cys Ala Pro Gly Met Gly Ala Gln
                565                 570                 575 ctc cga ggg cct atg gat gtc caa gat ccc atg cag ctc cga cct gga   1776
Leu Arg Gly Pro Met Asp Val Gln Asp Pro Met Gln Leu Arg Pro Gly
            580                 585                 590 cct ccc ttc cct ggc ccc cgt ttc cca ggc aac cag atg caa agg gtg   1824
```

```
                Pro Pro Phe Pro Gly Pro Arg Phe Pro Gly Asn Gln Met Gln Arg Val
                        595                 600                 605 ccc gga ttt gga ggt atg cag agt atg ccc atg gaa gta ccc atg aat          1872
Pro Gly Phe Gly Gly Met Gln Ser Met Pro Met Glu Val Pro Met Asn
610                 615                 620 gcc atg cag aga cct gta agg cca ggc atg gcc tgg aat gaa gac ttg          1920
Ala Met Gln Arg Pro Val Arg Pro Gly Met Ala Trp Asn Glu Asp Leu
625                 630                 635                 640 ccc cct att ggg gga ccc agc aac ttt gcc cag aat gcc gtg ccc tac          1968
Pro Pro Ile Gly Gly Pro Ser Asn Phe Ala Gln Asn Ala Val Pro Tyr
                645                 650                 655 cca ggt ggg cag ggg gag gca gag cga ttc atg acc cct cgt gtc cgg          2016
Pro Gly Gly Gln Gly Glu Ala Glu Arg Phe Met Thr Pro Arg Val Arg
                660                 665                 670 gag gag ctg ctg agg cac cag ttg ctg gag aag cgg tcc atg ggc atg          2064
Glu Glu Leu Leu Arg His Gln Leu Leu Glu Lys Arg Ser Met Gly Met
            675                 680                 685 cag cgt ccc ctg ggc atg gca ggt agc ggc atg gga cag agc atg gaa          2112
Gln Arg Pro Leu Gly Met Ala Gly Ser Gly Met Gly Gln Ser Met Glu
        690                 695                 700 atg gaa cgg atg ata cag gct cat cga cag atg gac cct gcc atg ttc          2160
Met Glu Arg Met Ile Gln Ala His Arg Gln Met Asp Pro Ala Met Phe
705                 710                 715                 720 ccg gga cag atg act gga gga gat ggt ctc gcc ggc aca ccc atg ggc          2208
Pro Gly Gln Met Thr Gly Gly Asp Gly Leu Ala Gly Thr Pro Met Gly
                725                 730                 735 ata gag ttt ggt gga ggt cgg ggc ctc ctg agc cct cca atg gga cag          2256
Ile Glu Phe Gly Gly Gly Arg Gly Leu Leu Ser Pro Pro Met Gly Gln
                740                 745                 750 tct ggg ctg cgg gag gta gac ccg cct atg ggg cca ggc aac ctc aac          2304
Ser Gly Leu Arg Glu Val Asp Pro Pro Met Gly Pro Gly Asn Leu Asn
            755                 760                 765 atg aac atg aat gtg aac atg aac atg aac atg aac ctg aat gtg cag          2352
Met Asn Met Asn Val Asn Met Asn Met Asn Met Asn Leu Asn Val Gln
        770                 775                 780 atg acg ccc cag cag cag atg ctg atg tca cag aag atg cgg ggc cct          2400
Met Thr Pro Gln Gln Gln Met Leu Met Ser Gln Lys Met Arg Gly Pro
785                 790                 795                 800 gga gac atg atg ggt cct cag ggc ctc agt ccc gaa gag atg gct cgg          2448
Gly Asp Met Met Gly Pro Gln Gly Leu Ser Pro Glu Glu Met Ala Arg
                805                 810                 815 gtt cgg gcc cag aac agt agt ggc atg atg ggg ggt ccg cag aag atg          2496
Val Arg Ala Gln Asn Ser Ser Gly Met Met Gly Gly Pro Gln Lys Met
            820                 825                 830 ctc atg cct tca cag ttt ccc aac cag ggc cag cag gga ttc tct ggg          2544
Leu Met Pro Ser Gln Phe Pro Asn Gln Gly Gln Gln Gly Phe Ser Gly
        835                 840                 845 ggc cag gga cct tac caa gcc atg ccc cag gac atg ggc aac act cca          2592
Gly Gln Gly Pro Tyr Gln Ala Met Pro Gln Asp Met Gly Asn Thr Pro
850                 855                 860 gac atg ttc agc cct gat cag agt tca gtg ccc atg ggc act gtg ggc          2640
Asp Met Phe Ser Pro Asp Gln Ser Ser Val Pro Met Gly Thr Val Gly
865                 870                 875                 880 act gcc cgg ctc agc cat atg cct ctg ccc cct gcc tcc aat cct cct          2688
Thr Ala Arg Leu Ser His Met Pro Leu Pro Pro Ala Ser Asn Pro Pro
                885                 890                 895 ggg tct gtg cac ttg gcc tcc aac agg ggg cta ggc agg cgg cct tca          2736
Gly Ser Val His Leu Ala Ser Asn Arg Gly Leu Gly Arg Arg Pro Ser
                900                 905                 910
```

```
gat ctc acc atc agt att aat cag atg ggc tca ccg ggc atg gga cat      2784
Asp Leu Thr Ile Ser Ile Asn Gln Met Gly Ser Pro Gly Met Gly His
        915                 920                 925 ctg aag tca ccc acc ctt agc cag gtg cac tcc ccc ctg gtc acc tca      2832
Leu Lys Ser Pro Thr Leu Ser Gln Val His Ser Pro Leu Val Thr Ser
    930                 935                 940 ccc tct gcc aac ctc aag tca ccc cag act ccc tcc cag atg gta ccc      2880
Pro Ser Ala Asn Leu Lys Ser Pro Gln Thr Pro Ser Gln Met Val Pro
945                 950                 955                 960 ttg cct tct gcc aac cca ccg gga cct ctc aag tca ccc cag gtc ctc      2928
Leu Pro Ser Ala Asn Pro Pro Gly Pro Leu Lys Ser Pro Gln Val Leu
                965                 970                 975 agc tct tcc ctc ggt gtg cgt tca ccc act ggc tca ccc agc agg ctc      2976
Ser Ser Ser Leu Gly Val Arg Ser Pro Thr Gly Ser Pro Ser Arg Leu
            980                 985                 990 aag tct ccc tcc atg gcg gtg cct tct cca ggc tgg gtc gcc tct ccc      3024
Lys Ser Pro Ser Met Ala Val Pro Ser Pro Gly Trp Val Ala Ser Pro
        995                 1000                1005 aag aca gcc atg cct agt cct ggg gtc tcc cag aac aag cag cca cct      3072
Lys Thr Ala Met Pro Ser Pro Gly Val Ser Gln Asn Lys Gln Pro Pro
    1010                1015                1020 ctc agc ata aac tct tcc tcc acc ctg ggc aac gtg gaa cag ggt gct      3120
Leu Ser Ile Asn Ser Ser Ser Thr Leu Gly Asn Val Glu Gln Gly Ala
1025                1030                1035                1040 ctt cca cct agc gca ccc cgg aac agc tcc tcc gct cct ccc gcc aac      3168
Leu Pro Pro Ser Ala Pro Arg Asn Ser Ser Ser Ala Pro Pro Ala Asn
                1045                1050                1055 cct tcc agt ggc ctc atg aac ccc agc cta ccg ttc aca tcc tcc cca      3216
Pro Ser Ser Gly Leu Met Asn Pro Ser Leu Pro Phe Thr Ser Ser Pro
            1060                1065                1070 gac ccc acc cct tcc cag aac cct ctg tca ctg atg atg tct cag atg      3264
Asp Pro Thr Pro Ser Gln Asn Pro Leu Ser Leu Met Met Ser Gln Met
        1075                1080                1085 tcc aag tac gcc atg ccc agc tcg acc ccg cta tac cac aac gcc atc      3312
Ser Lys Tyr Ala Met Pro Ser Ser Thr Pro Leu Tyr His Asn Ala Ile
    1090                1095                1100 aag acc atc gcc acc tca gat gac gag ctg ctg cct gac cgg ccc ctg      3360
Lys Thr Ile Ala Thr Ser Asp Asp Glu Leu Leu Pro Asp Arg Pro Leu
1105                1110                1115                1120 cta ccc cca ccc cca cca ccg cag ggc tct ggg cca ggt atc agc aat      3408
Leu Pro Pro Pro Pro Pro Pro Gln Gly Ser Gly Pro Gly Ile Ser Asn
                1125                1130                1135 aac cag ccc aac cag atg cac atg aac cct gct gct gcc cag agc ccc      3456
Asn Gln Pro Asn Gln Met His Met Asn Pro Ala Ala Ala Gln Ser Pro
            1140                1145                1150 atg ggc atg aac ttg cca ggc cag cag ccc ctg tcc cat gag cct ccc      3504
Met Gly Met Asn Leu Pro Gly Gln Gln Pro Leu Ser His Glu Pro Pro
        1155                1160                1165 cct act atg ttg ccc tcc ccc acc cct ctg ggg tcc aac att cca ctg      3552
Pro Thr Met Leu Pro Ser Pro Thr Pro Leu Gly Ser Asn Ile Pro Leu
    1170                1175                1180 cat ccc aat gca cag ggg act ggg ggc tct tct caa aac tca atg atg      3600
His Pro Asn Ala Gln Gly Thr Gly Gly Ser Ser Gln Asn Ser Met Met
1185                1190                1195                1200 atg gcc cca gga ggc cca gac tcc cta aat gcc cct tgt ggc cct gtg      3648
Met Ala Pro Gly Gly Pro Asp Ser Leu Asn Ala Pro Cys Gly Pro Val
                1205                1210                1215 ccc agc tcc tcc cag atg atg tcc ttc cct cct cgg ctg cag caa cct      3696
Pro Ser Ser Ser Gln Met Met Ser Phe Pro Pro Arg Leu Gln Gln Pro
            1220                1225                1230
```

```
cac ggt gcc atg gcc ccc acc ggg gcc ggg ggc cca ggc ctg cag cag      3744
His Gly Ala Met Ala Pro Thr Gly Ala Gly Gly Pro Gly Leu Gln Gln
        1235                1240                1245 cac tac cct tca ggc atg gcc ctg ccc ccc gag gac ctg ccc acc cag      3792
His Tyr Pro Ser Gly Met Ala Leu Pro Pro Glu Asp Leu Pro Thr Gln
    1250                1255                1260 cca ccg ggt ccc ata ccc ccc cag cag cac cta atg ggc aaa ggc atg      3840
Pro Pro Gly Pro Ile Pro Pro Gln Gln His Leu Met Gly Lys Gly Met
1265                1270                1275                1280 act ggc cgc atg ggc gac gca tac cca ccc ggg gtg ctc cct ggg gtg      3888
Thr Gly Arg Met Gly Asp Ala Tyr Pro Pro Gly Val Leu Pro Gly Val
                1285                1290                1295 gca tcg gta ctg aat gac cca gag ctg agt gag gtg atc cgg ccc acc      3936
Ala Ser Val Leu Asn Asp Pro Glu Leu Ser Glu Val Ile Arg Pro Thr
            1300                1305                1310 cct acc ggc att cct gag ttc gac tta tcc agg atc atc ccc tct gag      3984
Pro Thr Gly Ile Pro Glu Phe Asp Leu Ser Arg Ile Ile Pro Ser Glu
        1315                1320                1325 aaa cca agc agc acc ctc cag tac ttc ccc aag agc gag aac cag ccc      4032
Lys Pro Ser Ser Thr Leu Gln Tyr Phe Pro Lys Ser Glu Asn Gln Pro
    1330                1335                1340 ccc aag gcc cag ccc ccc aat ctg cat ctc atg aac ctg cag aac atg      4080
Pro Lys Ala Gln Pro Pro Asn Leu His Leu Met Asn Leu Gln Asn Met
1345                1350                1355                1360 atg gca gag cag acc ccg tct cga ccc ccc aac ctc ccg ggc caa cag      4128
Met Ala Glu Gln Thr Pro Ser Arg Pro Pro Asn Leu Pro Gly Gln Gln
                1365                1370                1375 ggg gtc cag cgg ggg ctc agc atg tcc atg tgc cac cct gga cag atg      4176
Gly Val Gln Arg Gly Leu Ser Met Ser Met Cys His Pro Gly Gln Met
            1380                1385                1390 tcc ttg ctg ggc agg aca ggt gtg ccc cca caa cag ggc atg gtg ccc      4224
Ser Leu Leu Gly Arg Thr Gly Val Pro Pro Gln Gln Gly Met Val Pro
        1395                1400                1405 cat ggc ctg cac cag ggg gtc atg tcc cct cca caa ggc ctc atg acc      4272
His Gly Leu His Gln Gly Val Met Ser Pro Pro Gln Gly Leu Met Thr
    1410                1415                1420 cag cag aat ttt atg ctg atg aag cag agg ggt gtg ggg ggc gag gtc      4320
Gln Gln Asn Phe Met Leu Met Lys Gln Arg Gly Val Gly Gly Glu Val
1425                1430                1435                1440 tac acc cag cct ccc cac atg ctc tcc cca cag ggc tcc ctc atg ggc      4368
Tyr Thr Gln Pro Pro His Met Leu Ser Pro Gln Gly Ser Leu Met Gly
                1445                1450                1455 ccc cca ccc cag cag aac ctc atg gtg tcc cac cct ctg cgt cag cgc      4416
Pro Pro Pro Gln Gln Asn Leu Met Val Ser His Pro Leu Arg Gln Arg
            1460                1465                1470 agt gtg tct ctg gac agc cag atg ggc tac ctg cca acg ccg ggc agc      4464
Ser Val Ser Leu Asp Ser Gln Met Gly Tyr Leu Pro Thr Pro Gly Ser
        1475                1480                1485 atg gcc aat cta ccc ttc                                              4482
Met Ala Asn Leu Pro Phe
    1490

<210> SEQ ID NO 2
<211> LENGTH: 1494
<212> TYPE: PRT
<213> ORGANISM: Mus musculus

<400> SEQUENCE: 2

Met Arg Ile Leu Ala Asn Lys Thr Arg Leu Pro His Pro Arg Arg Arg
1               5                   10                  15
```

```
Glu Ala Pro Gly Ser Pro Pro Leu Ser Pro Arg Gly His Cys Pro Pro
            20                  25                  30

Ala Pro Ala Lys Pro Met His Pro Glu Asn Lys Leu Thr Asn His Gly
            35                  40                  45

Lys Thr Gly Asn Gly Gly Ala Gln Ser Gln His Gln Asn Val Asn Gln
 50                  55                  60

Gly Pro Thr Cys Asn Leu Gly Ser Lys Gly Val Gly Ala Gly Ser His
 65                  70                  75                  80

Gly Ala Lys Ala Asn Gln Ile Ser Pro Ser Asn Ser Ser Leu Lys Asn
                85                  90                  95

Pro Gln Ala Gly Val Ser Pro Phe Ser Ser Leu Lys Gly Lys Val Lys
            100                 105                 110

Arg Glu Arg Ser Val Ser Val Asp Ser Gly Glu Gln Arg Glu Ala Gly
            115                 120                 125

Thr Pro Ser Leu Asp Ser Glu Ala Lys Glu Val Ala Pro Arg Ser Lys
130                 135                 140

Arg Arg Cys Val Leu Glu Arg Lys Gln Pro Tyr Ser Gly Asp Glu Trp
145                 150                 155                 160

Cys Ser Gly Pro Asp Ser Glu Asp Asp Lys Pro Ile Ala Ala Ala
                165                 170                 175

His Asn Cys Asn Val Ala Asp Pro Ala Met Val Thr Pro Gln Leu Gly
            180                 185                 190

Pro Gly Gln Thr Ala Gln Leu Pro Leu Ser Glu Ser Ser Ala Pro Gly
            195                 200                 205

Pro Gln His Gly Pro Gln Pro Gly Leu Arg Pro Asp Val Pro Gly Gly
            210                 215                 220

Gly Gly Gly Gly Val Pro Gly Lys Pro Pro Ser Gln Phe Val Tyr Val
225                 230                 235                 240

Phe Thr Thr His Leu Ala Asn Thr Ala Ala Glu Ala Val Leu Gln Gly
            245                 250                 255

Arg Ala Glu Ser Ile Leu Ala Tyr His Gln Gln Asn Val Pro Arg Ala
            260                 265                 270

Lys Leu Asp Gln Ala Pro Lys Val Pro Pro Thr Pro Glu Pro Leu Pro
            275                 280                 285

Leu Asn Thr Pro Ser Ala Gly Thr Pro Gln Ser Gln Pro Pro Leu
            290                 295                 300

Pro Pro Pro Pro Ala Pro Gly Ser Ala Pro Pro Ala Leu Pro Pro
305                 310                 315                 320

Glu Gly Pro Pro Glu Asp Thr Ser Gln Asp Leu Ala Pro Asn Ser Val
            325                 330                 335

Gly Ala Ala Ser Thr Gly Gly Thr Gly Thr His Pro Asn Thr
            340                 345                 350

Pro Thr Ala Ala Thr Ala Asn Asn Pro Leu Pro Pro Gly Gly Asp Pro
            355                 360                 365

Gly Ser Ala Pro Gly Ser Ala Leu Leu Gly Glu Ala Thr Pro Thr Gly
            370                 375                 380

Asn Gly Gln Arg Asn Leu Val Gly Ser Glu Gly Leu Ser Lys Glu Gln
385                 390                 395                 400

Leu Glu His Arg Glu Arg Ser Leu Gln Thr Leu Arg Asp Ile Glu Arg
            405                 410                 415

Leu Leu Leu Arg Ser Gly Glu Thr Glu Pro Phe Leu Lys Gly Pro Pro
            420                 425                 430
```

```
Gly Gly Ala Gly Glu Gly Gly Pro Pro Ala Gln Ala Pro Ser Ala Ala
            435                 440                 445

Gln Pro Pro Ser Ala Pro Pro Gly Gly Leu Lys Lys Tyr Glu
    450                 455                 460

Pro Leu Gln Ser Met Ile Ser Gln Thr Gln Ser Leu Gly Gly Pro Pro
465                 470                 475                 480

Leu Glu His Glu Val Pro Gly His Pro Gln Gly Gly Asp Met Gly Gln
                    485                 490                 495

Gln Met Asn Met Met Met Gln Arg Leu Gly Gln Asp Ser Leu Thr Pro
                500                 505                 510

Glu Gln Val Ala Trp Arg Lys Leu Gln Glu Glu Tyr Tyr Glu Glu Lys
            515                 520                 525

Arg Arg Lys Glu Glu Gln Ile Gly Leu His Gly Arg Pro Leu Gln
530                 535                 540

Asp Met Val Gly Met Gly Gly Met Gly Arg Gly Pro Pro Pro
545                 550                 555                 560

Tyr His Ser Lys Pro Gly Asp Gln Cys Ala Pro Gly Met Gly Ala Gln
                565                 570                 575

Leu Arg Gly Pro Met Asp Val Gln Asp Pro Met Gln Leu Arg Pro Gly
            580                 585                 590

Pro Pro Phe Pro Gly Pro Arg Phe Pro Gly Asn Gln Met Gln Arg Val
        595                 600                 605

Pro Gly Phe Gly Gly Met Gln Ser Met Pro Met Glu Val Pro Met Asn
    610                 615                 620

Ala Met Gln Arg Pro Val Arg Pro Gly Met Ala Trp Asn Glu Asp Leu
625                 630                 635                 640

Pro Pro Ile Gly Gly Pro Ser Asn Phe Ala Gln Asn Ala Val Pro Tyr
                645                 650                 655

Pro Gly Gly Gln Gly Glu Ala Glu Arg Phe Met Thr Pro Arg Val Arg
            660                 665                 670

Glu Glu Leu Leu Arg His Gln Leu Leu Glu Lys Arg Ser Met Gly Met
        675                 680                 685

Gln Arg Pro Leu Gly Met Ala Gly Ser Gly Met Gly Gln Ser Met Glu
    690                 695                 700

Met Glu Arg Met Ile Gln Ala His Arg Gln Met Asp Pro Ala Met Phe
705                 710                 715                 720

Pro Gly Gln Met Thr Gly Gly Asp Gly Leu Ala Gly Thr Pro Met Gly
                725                 730                 735

Ile Glu Phe Gly Gly Gly Arg Gly Leu Leu Ser Pro Pro Met Gly Gln
            740                 745                 750

Ser Gly Leu Arg Glu Val Asp Pro Pro Met Gly Pro Gly Asn Leu Asn
        755                 760                 765

Met Asn Met Asn Val Asn Met Asn Met Asn Met Asn Leu Asn Val Gln
    770                 775                 780

Met Thr Pro Gln Gln Gln Met Leu Met Ser Gln Lys Met Arg Gly Pro
785                 790                 795                 800

Gly Asp Met Met Gly Pro Gln Gly Leu Ser Pro Glu Glu Met Ala Arg
                805                 810                 815

Val Arg Ala Gln Asn Ser Ser Gly Met Met Gly Gly Pro Gln Lys Met
            820                 825                 830

Leu Met Pro Ser Gln Phe Pro Asn Gln Gly Gln Gln Gly Phe Ser Gly
        835                 840                 845

Gly Gln Gly Pro Tyr Gln Ala Met Pro Gln Asp Met Gly Asn Thr Pro
```

-continued

```
            850                 855                 860
Asp Met Phe Ser Pro Asp Gln Ser Val Pro Met Gly Thr Val Gly
865                 870                 875                 880

Thr Ala Arg Leu Ser His Met Pro Leu Pro Ala Ser Asn Pro Pro
                885                 890                 895

Gly Ser Val His Leu Ala Ser Asn Arg Gly Leu Gly Arg Arg Pro Ser
            900                 905                 910

Asp Leu Thr Ile Ser Ile Asn Gln Met Gly Ser Pro Gly Met Gly His
            915                 920                 925

Leu Lys Ser Pro Thr Leu Ser Gln Val His Ser Pro Leu Val Thr Ser
            930                 935                 940

Pro Ser Ala Asn Leu Lys Ser Pro Gln Thr Pro Ser Gln Met Val Pro
945                 950                 955                 960

Leu Pro Ser Ala Asn Pro Gly Pro Leu Lys Ser Pro Gln Val Leu
                965                 970                 975

Ser Ser Ser Leu Gly Val Arg Ser Pro Thr Gly Ser Pro Ser Arg Leu
            980                 985                 990

Lys Ser Pro Ser Met Ala Val Pro Ser Pro Gly Trp Val Ala Ser Pro
            995                 1000                1005

Lys Thr Ala Met Pro Ser Pro Gly Val Ser Gln Asn Lys Gln Pro Pro
    1010                1015                1020

Leu Ser Ile Asn Ser Ser Ser Thr Leu Gly Asn Val Glu Gln Gly Ala
1025                1030                1035                1040

Leu Pro Pro Ser Ala Pro Arg Asn Ser Ser Ala Pro Pro Ala Asn
                1045                1050                1055

Pro Ser Ser Gly Leu Met Asn Pro Ser Leu Pro Phe Thr Ser Ser Pro
                1060                1065                1070

Asp Pro Thr Pro Ser Gln Asn Pro Leu Ser Leu Met Met Ser Gln Met
            1075                1080                1085

Ser Lys Tyr Ala Met Pro Ser Ser Thr Pro Leu Tyr His Asn Ala Ile
            1090                1095                1100

Lys Thr Ile Ala Thr Ser Asp Asp Glu Leu Leu Pro Asp Arg Pro Leu
1105                1110                1115                1120

Leu Pro Pro Pro Pro Pro Gln Gly Ser Gly Pro Gly Ile Ser Asn
                1125                1130                1135

Asn Gln Pro Asn Gln Met His Met Asn Pro Ala Ala Ala Gln Ser Pro
                1140                1145                1150

Met Gly Met Asn Leu Pro Gly Gln Gln Pro Leu Ser His Glu Pro Pro
            1155                1160                1165

Pro Thr Met Leu Pro Ser Pro Thr Pro Leu Gly Ser Asn Ile Pro Leu
    1170                1175                1180

His Pro Asn Ala Gln Gly Thr Gly Gly Ser Ser Gln Asn Ser Met Met
1185                1190                1195                1200

Met Ala Pro Gly Gly Pro Asp Ser Leu Asn Ala Pro Cys Gly Pro Val
                1205                1210                1215

Pro Ser Ser Ser Gln Met Met Ser Phe Pro Pro Arg Leu Gln Gln Pro
                1220                1225                1230

His Gly Ala Met Ala Pro Thr Gly Ala Gly Gly Pro Gly Leu Gln Gln
            1235                1240                1245

His Tyr Pro Ser Gly Met Ala Leu Pro Pro Glu Asp Leu Pro Thr Gln
            1250                1255                1260

Pro Pro Gly Pro Ile Pro Pro Gln Gln His Leu Met Gly Lys Gly Met
1265                1270                1275                1280
```

Thr Gly Arg Met Gly Asp Ala Tyr Pro Pro Gly Val Leu Pro Gly Val
            1285                1290                1295

Ala Ser Val Leu Asn Asp Pro Glu Leu Ser Glu Val Ile Arg Pro Thr
        1300                1305                1310

Pro Thr Gly Ile Pro Glu Phe Asp Leu Ser Arg Ile Ile Pro Ser Glu
            1315                1320                1325

Lys Pro Ser Ser Thr Leu Gln Tyr Phe Pro Lys Ser Glu Asn Gln Pro
        1330                1335                1340

Pro Lys Ala Gln Pro Pro Asn Leu His Leu Met Asn Leu Gln Asn Met
1345                1350                1355                1360

Met Ala Glu Gln Thr Pro Ser Arg Pro Pro Asn Leu Pro Gly Gln Gln
            1365                1370                1375

Gly Val Gln Arg Gly Leu Ser Met Ser Met Cys His Pro Gly Gln Met
        1380                1385                1390

Ser Leu Leu Gly Arg Thr Gly Val Pro Pro Gln Gln Gly Met Val Pro
            1395                1400                1405

His Gly Leu His Gln Gly Val Met Ser Pro Gln Gly Leu Met Thr
        1410                1415                1420

Gln Gln Asn Phe Met Leu Met Lys Gln Arg Gly Val Gly Gly Glu Val
1425                1430                1435                1440

Tyr Thr Gln Pro Pro His Met Leu Ser Pro Gln Gly Ser Leu Met Gly
            1445                1450                1455

Pro Pro Pro Gln Gln Asn Leu Met Val Ser His Pro Leu Arg Gln Arg
        1460                1465                1470

Ser Val Ser Leu Asp Ser Gln Met Gly Tyr Leu Pro Thr Pro Gly Ser
            1475                1480                1485

Met Ala Asn Leu Pro Phe
    1490

<210> SEQ ID NO 3
<211> LENGTH: 960
<212> TYPE: DNA
<213> ORGANISM: Mus musculus
<220> FEATURE:
<221> NAME/KEY: CDS
<222> LOCATION: (1)..(960)

<400> SEQUENCE: 3

```
ctg gcc aac aca gcg gca gag gca gtg ctg cag ggc cgg gca gag tcc      48
Leu Ala Asn Thr Ala Ala Glu Ala Val Leu Gln Gly Arg Ala Glu Ser
 1               5                  10                  15 atc ctt gcc tac cac cag cag aat gtg cct cgg gcc aag ctg gat cag      96
Ile Leu Ala Tyr His Gln Gln Asn Val Pro Arg Ala Lys Leu Asp Gln
             20                  25                  30 gcc cct aaa gtg cca ccc acc cca gaa cca cta ccc ctg aat acg cca     144
Ala Pro Lys Val Pro Pro Thr Pro Glu Pro Leu Pro Leu Asn Thr Pro
         35                  40                  45 tca gca ggt aca cca cag tcc cag cca cct cct ttg cca ccg cca ccc     192
Ser Ala Gly Thr Pro Gln Ser Gln Pro Pro Leu Pro Pro Pro Pro
     50                  55                  60 cca gcc cct ggc agt gcc cct cct gct ctg ccc ccg gag ggg cct cct     240
Pro Ala Pro Gly Ser Ala Pro Pro Ala Leu Pro Pro Glu Gly Pro Pro
 65                  70                  75                  80 gaa gac acc agt cag gac ctg gcc ccc aac tca gtg gga gct gcc agt     288
Glu Asp Thr Ser Gln Asp Leu Ala Pro Asn Ser Val Gly Ala Ala Ser
                 85                  90                  95 aca ggt ggt ggg act ggg ggt acc cac cct aac acc cca acg gct gcc     336
Thr Gly Gly Gly Thr Gly Gly Thr His Pro Asn Thr Pro Thr Ala Ala
```

```
                Thr Gly Gly Gly Thr Gly Gly Thr His Pro Asn Thr Pro Thr Ala Ala
                                100                 105                 110 acc gct aac aac cct ctg cct cct gga gga gac cct ggc agt gcc cct           384
Thr Ala Asn Asn Pro Leu Pro Pro Gly Gly Asp Pro Gly Ser Ala Pro
        115                 120                 125 ggc tcc gcc cta ttg ggg gag gcc acg ccc acc gga aat ggg cag agg           432
Gly Ser Ala Leu Leu Gly Glu Ala Thr Pro Thr Gly Asn Gly Gln Arg
130                 135                 140 aac ctg gtg ggc tct gag ggc ctg tcc aaa gag cag ctg gag cac cgg           480
Asn Leu Val Gly Ser Glu Gly Leu Ser Lys Glu Gln Leu Glu His Arg
145                 150                 155                 160 gag cgc tcc ctc cag aca ctg cgg gac atc gag agg ctg ctg ctc cgc           528
Glu Arg Ser Leu Gln Thr Leu Arg Asp Ile Glu Arg Leu Leu Leu Arg
                165                 170                 175 agt ggg gag act gag ccc ttc ctc aag ggg ccc ccg gga gga gct ggt           576
Ser Gly Glu Thr Glu Pro Phe Leu Lys Gly Pro Pro Gly Gly Ala Gly
            180                 185                 190 gag gga ggc cca ccg gca caa gcg ccc tct gct gct caa ccg cct ccc           624
Glu Gly Gly Pro Pro Ala Gln Ala Pro Ser Ala Ala Gln Pro Pro Pro
        195                 200                 205 tcc gcc cct cct ggg ggg ctg aag aag tat gag gag cct ctg cag tca           672
Ser Ala Pro Pro Gly Gly Leu Lys Lys Tyr Glu Glu Pro Leu Gln Ser
210                 215                 220 atg atc tca cag aca cag agc cta gga ggt ccc cct ctg gag cat gaa           720
Met Ile Ser Gln Thr Gln Ser Leu Gly Gly Pro Pro Leu Glu His Glu
225                 230                 235                 240 gtg ccg ggg cac cct cag ggt gga gac atg gga cag caa atg aac atg           768
Val Pro Gly His Pro Gln Gly Gly Asp Met Gly Gln Gln Met Asn Met
                245                 250                 255 atg atg cag agg ctg ggc cag gac agt ctg acg ccc gag cag gtg gcc           816
Met Met Gln Arg Leu Gly Gln Asp Ser Leu Thr Pro Glu Gln Val Ala
            260                 265                 270 tgg cgc aaa ctg cag gaa gag tac tac gag gag aag cgg cgg aaa gag           864
Trp Arg Lys Leu Gln Glu Glu Tyr Tyr Glu Glu Lys Arg Arg Lys Glu
        275                 280                 285 gag cag att gga ttg cac gga ggc cgc cct ctg cag gac atg gtg gga           912
Glu Gln Ile Gly Leu His Gly Gly Arg Pro Leu Gln Asp Met Val Gly
290                 295                 300 atg ggg ggt atg atg ggg agg ggg ccc cca cct cct tac cac agc aaa           960
Met Gly Gly Met Met Gly Arg Gly Pro Pro Pro Pro Tyr His Ser Lys
305                 310                 315                 320

<210> SEQ ID NO 4
<211> LENGTH: 320
<212> TYPE: PRT
<213> ORGANISM: Mus musculus

<400> SEQUENCE: 4

Leu Ala Asn Thr Ala Ala Glu Ala Val Leu Gln Gly Arg Ala Glu Ser
 1               5                  10                  15

Ile Leu Ala Tyr His Gln Gln Asn Val Pro Arg Ala Lys Leu Asp Gln
            20                  25                  30

Ala Pro Lys Val Pro Pro Thr Pro Glu Pro Leu Pro Leu Asn Thr Pro
        35                  40                  45

Ser Ala Gly Thr Pro Gln Ser Gln Pro Pro Leu Pro Pro Pro
    50                  55                  60

Pro Ala Pro Gly Ser Ala Pro Pro Ala Leu Pro Pro Glu Gly Pro Pro
65                  70                  75                  80

Glu Asp Thr Ser Gln Asp Leu Ala Pro Asn Ser Val Gly Ala Ala Ser
```

```
                    85                  90                  95
Thr Gly Gly Gly Thr Gly Gly Thr His Pro Asn Thr Pro Thr Ala Ala
            100                 105                 110
Thr Ala Asn Asn Pro Leu Pro Pro Gly Gly Asp Pro Gly Ser Ala Pro
            115                 120                 125
Gly Ser Ala Leu Leu Gly Glu Ala Thr Pro Thr Gly Asn Gly Gln Arg
            130                 135                 140
Asn Leu Val Gly Ser Glu Gly Leu Ser Lys Glu Gln Leu Glu His Arg
145                 150                 155                 160
Glu Arg Ser Leu Gln Thr Leu Arg Asp Ile Glu Arg Leu Leu Leu Arg
                165                 170                 175
Ser Gly Glu Thr Glu Pro Phe Leu Lys Gly Pro Pro Gly Ala Gly
            180                 185                 190
Glu Gly Gly Pro Pro Ala Gln Ala Pro Ser Ala Ala Gln Pro Pro Pro
            195                 200                 205
Ser Ala Pro Pro Gly Gly Leu Lys Lys Tyr Glu Pro Leu Gln Ser
    210                 215                 220
Met Ile Ser Gln Thr Gln Ser Leu Gly Gly Pro Pro Leu Glu His Glu
225                 230                 235                 240
Val Pro Gly His Pro Gln Gly Gly Asp Met Gly Gln Gln Met Asn Met
                245                 250                 255
Met Met Gln Arg Leu Gly Gln Asp Ser Leu Thr Pro Glu Gln Val Ala
            260                 265                 270
Trp Arg Lys Leu Gln Glu Glu Tyr Tyr Glu Glu Lys Arg Arg Lys Glu
            275                 280                 285
Glu Gln Ile Gly Leu His Gly Gly Arg Pro Leu Gln Asp Met Val Gly
            290                 295                 300
Met Gly Gly Met Met Gly Arg Gly Pro Pro Pro Tyr His Ser Lys
305                 310                 315                 320

<210> SEQ ID NO 5
<211> LENGTH: 386
<212> TYPE: DNA
<213> ORGANISM: Homo sapiens

<400> SEQUENCE: 5
gttaccccac cccaggagga gagaagctcc agggagcccg ccgctgtccc cccgcggtca    60
ttgccccct gccccagcca agccaatgca cccagaaaat aaattgacca atcatggcaa   120
gacagggaat ggcggggccc aatctcagca ccagaatgtg aaccaaggac ccacctgcaa   180
cgtgggctcg aagggcgtgg gggcggggaa ccatgggggc aaggccaacc agatctcgcc   240
tagcaactca agtctgaaga accccaggc agggtgccc cctttcagct cgctcaaggg   300
caaggtgaag agggaccgga gtgtgtctgt ggactctgga gagcagcgag aggctgggac   360
cccatccctg gattcagagg ccaaag                                        386

<210> SEQ ID NO 6
<211> LENGTH: 120
<212> TYPE: DNA
<213> ORGANISM: Homo sapiens

<400> SEQUENCE: 6
aggtggcgcc gcggagtaag cggcgctgtg tgctggagcg gaagcagccg tacagtgggg    60
acgaatggtg ctctggaccg gacagtgagg aggacgacaa gcccattggg gccacccaca   120
```

<210> SEQ ID NO 7
<211> LENGTH: 1933
<212> TYPE: DNA
<213> ORGANISM: Homo sapiens

<400> SEQUENCE: 7

| | | | | | |
|---|---|---|---|---|---|
| ggcttgtcca | aagagcagct | ggagcatcgg | gaacggtccc | tccagacgct | gcgagacatt | 60 |
| gagcgactgc | tgctccgcag | cggagagact | gagctcttcc | tcaaggggcc | cccaggagga | 120 |
| gcgggtgagg | gagggccacc | agcacaagcc | ccccctccac | cccagcagca | acccatggcc | 180 |
| cctcccagtg | ggctgaaaaa | atatgaggac | cctttgcagt | ccatgatttc | acagacacag | 240 |
| agcctagggg | gccccccgct | ggagcatgaa | gtgcctgggc | acccccgggt | ggggacatg | 300 |
| gggcagcaga | tgaacatgat | gatacagagg | ctgggccagg | acagcctcac | gcctgagcag | 360 |
| gtggcctggc | gcaagctgca | ggaggagtac | tacgaagaga | aacggcggaa | agaggaacag | 420 |
| attgggctgc | atgggagccg | tcctctgcag | gacatgatgg | gcatgggggg | catgatggtg | 480 |
| aggggggcccc | cgcctcctta | ccacagcaag | cctggggatc | agtggccacc | tggaatgggt | 540 |
| gcgcagctgc | gggggcccat | ggatgttcaa | gatcccatgc | agctccgggg | cggacctccc | 600 |
| tttcctgggc | cccgtttccc | aggcaaccag | atacaacggg | tacctgggtt | tgggggcatg | 660 |
| cagagtatgc | ccatggaggt | gcccatgaat | gccatgcaga | ggcccgtgag | accaggcatg | 720 |
| ggctggaccg | aagacttgcc | cccatatggg | ggacccagca | attttgccca | gaacaccatg | 780 |
| ccctacccag | gtgggcaggg | tgaggcggag | cgattcatga | ctccccgggt | ccgtgaggag | 840 |
| ctgctgcggc | accagctgct | ggagaagcgg | tcgatgggca | tgcagcgccc | cctgggcatg | 900 |
| gcaggcagtg | catgggaca | gagcatggag | atggagcgga | tgatgcaggc | gcaccgacag | 960 |
| atggatcctg | ccatgtttcc | cggcagatg | gctggtggtg | agggcctggc | gggcactccc | 1020 |
| atgggcatgg | agtttggtgg | aggccggggc | ctcctgagcc | ctcccatggg | gcagtctggg | 1080 |
| ctgagggagg | tggacccacc | catggggcca | ggcaacctca | acatgaacat | gaatgtcaac | 1140 |
| atgaacatga | acatgaacct | gaacgtgcag | atgaccccgc | agcagcagat | gctgatgtcg | 1200 |
| cagaagatgc | ggggccctgg | ggacttgatg | gggcccagg | gcctcagtcc | tgaggagatg | 1260 |
| gcccgggttc | gggcccagaa | cagcagtggc | gtgatgggcg | gcccgcagaa | gatgctgatg | 1320 |
| ccttcacagt | ttcccaacca | gggccagcag | ggattctctg | gaggcagggg | acctaccaa | 1380 |
| gccatgtccc | aggacatggg | caatacccaa | gacatgttca | gccctgatca | gagctcaatg | 1440 |
| cccatgagca | acgtgggcac | cacccggctc | agccacatgc | ctctgccccc | tgcgtccaat | 1500 |
| cctcctggga | ccgtgcattc | agccccaaac | cgggggctag | gcaggcggcc | ttcggacctc | 1560 |
| accatcagta | ttaatcagat | gggctcaccg | ggcatggggc | acttgaagtc | gcccacccctt | 1620 |
| agccaggtgc | actcacccct | ggtcacctcg | ccctctgcca | acctcaagtc | accccagact | 1680 |
| ccctcacaga | tggtgccctt | gccttctgcc | aacccgccag | gacctctcaa | gtcgcccag | 1740 |
| gtcctcggct | cctccctcag | tgtccgttca | cccactggct | cgcccagcag | gctcaagtct | 1800 |
| ccttccatgg | cggtgccttc | tccaggctgg | gttgcctcac | ctaagacggc | catgcccagc | 1860 |
| ccgggggtct | cccagaacaa | gcagccgcct | ctcaacatga | actcttccac | caccctgagc | 1920 |
| aacatggaac | agg | | | | | 1933 |

<210> SEQ ID NO 8
<211> LENGTH: 282
<212> TYPE: DNA
<213> ORGANISM: Homo sapiens -continued

```
<400> SEQUENCE: 8
gtaccctccc gcctagcggc ccccggagca gctcctcagc acctcccgcc aaccctccca      60
gcggcctcat gaaccccagc ctaccattca cttcctcccc agaccccaca ccttcccaga     120 acccctgtc actgatgatg acccagatgt ccaagtacgc catgcccagc tccacccccgc     180 tctaccacaa tgccatcaag accatcgcca cctcagacga cgagctgctg cccgaccggc     240
ccctgctgcc cccccaccca ccaccgcagg gctccgggcc ag                        282

<210> SEQ ID NO 9
<211> LENGTH: 506
<212> TYPE: DNA
<213> ORGANISM: Homo sapiens
<220> FEATURE:
<221> NAME/KEY: CDS
<222> LOCATION: (2)..(505)

<400> SEQUENCE: 9 g tta ccc cac ccc agg agg aga gaa gct cca ggg agc ccg ccg ctg tcc      49
  Leu Pro His Pro Arg Arg Arg Glu Ala Pro Gly Ser Pro Pro Leu Ser
   1               5                  10                  15 ccc cgc ggt cat tgc ccc cct gcc cca gcc aag cca atg cac cca gaa       97
Pro Arg Gly His Cys Pro Pro Ala Pro Ala Lys Pro Met His Pro Glu
             20                  25                  30 aat aaa ttg acc aat cat ggc aag aca ggg aat ggc ggg gcc caa tct      145
Asn Lys Leu Thr Asn His Gly Lys Thr Gly Asn Gly Gly Ala Gln Ser
         35                  40                  45 cag cac cag aat gtg aac caa gga ccc acc tgc aac gtg ggc tcg aag      193
Gln His Gln Asn Val Asn Gln Gly Pro Thr Cys Asn Val Gly Ser Lys
     50                  55                  60 ggc gtg ggg gcg ggg aac cat ggg ggc aag gcc aac cag atc tcg cct      241
Gly Val Gly Ala Gly Asn His Gly Gly Lys Ala Asn Gln Ile Ser Pro
 65                  70                  75                  80 agc aac tca agt ctg aag aac ccc cag gca ggg gtg ccc cct ttc agc      289
Ser Asn Ser Ser Leu Lys Asn Pro Gln Ala Gly Val Pro Pro Phe Ser
                 85                  90                  95 tcg ctc aag ggc aag gtg aag agg gac cgg agt gtg tct gtg gac tct      337
Ser Leu Lys Gly Lys Val Lys Arg Asp Arg Ser Val Ser Val Asp Ser
            100                 105                 110 gga gag cag cga gag gct ggg acc cca tcc ctg gat tca gag gcc aaa      385
Gly Glu Gln Arg Glu Ala Gly Thr Pro Ser Leu Asp Ser Glu Ala Lys
        115                 120                 125 gag gtg gcg ccg cgg agt aag cgg cgc tgt gtg ctg gag cgg aag cag      433
Glu Val Ala Pro Arg Ser Lys Arg Arg Cys Val Leu Glu Arg Lys Gln
    130                 135                 140 ccg tac agt ggg gac gaa tgg tgc tct gga ccg gac agt gag gag gac      481
Pro Tyr Ser Gly Asp Glu Trp Cys Ser Gly Pro Asp Ser Glu Glu Asp
145                 150                 155                 160 gac aag ccc att ggg gcc acc cac a                                     506
Asp Lys Pro Ile Gly Ala Thr His
                165

<210> SEQ ID NO 10
<211> LENGTH: 168
<212> TYPE: PRT
<213> ORGANISM: Homo sapiens

<400> SEQUENCE: 10

Leu Pro His Pro Arg Arg Arg Glu Ala Pro Gly Ser Pro Pro Leu Ser
 1               5                  10                  15

Pro Arg Gly His Cys Pro Pro Ala Pro Ala Lys Pro Met His Pro Glu
```

```
                20                  25                  30
Asn Lys Leu Thr Asn His Gly Lys Thr Gly Asn Gly Gly Ala Gln Ser
         35                  40                  45

Gln His Gln Asn Val Asn Gln Gly Pro Thr Cys Asn Val Gly Ser Lys
     50                  55                  60

Gly Val Gly Ala Gly Asn His Gly Gly Lys Ala Asn Gln Ile Ser Pro
 65                  70                  75                  80

Ser Asn Ser Ser Leu Lys Asn Pro Gln Ala Gly Val Pro Pro Phe Ser
                 85                  90                  95

Ser Leu Lys Gly Lys Val Lys Arg Asp Arg Ser Val Ser Val Asp Ser
             100                 105                 110

Gly Glu Gln Arg Glu Ala Gly Thr Pro Ser Leu Asp Ser Glu Ala Lys
         115                 120                 125

Glu Val Ala Pro Arg Ser Lys Arg Arg Cys Val Leu Glu Arg Lys Gln
130                 135                 140

Pro Tyr Ser Gly Asp Glu Trp Cys Ser Gly Pro Asp Ser Glu Glu Asp
145                 150                 155                 160

Asp Lys Pro Ile Gly Ala Thr His
                165

<210> SEQ ID NO 11
<211> LENGTH: 2215
<212> TYPE: DNA
<213> ORGANISM: Homo sapiens
<220> FEATURE:
<221> NAME/KEY: CDS
<222> LOCATION: (1)..(2214)

<400> SEQUENCE: 11 ggc ttg tcc aaa gag cag ctg gag cat cgg gaa cgg tcc ctc cag acg      48
Gly Leu Ser Lys Glu Gln Leu Glu His Arg Glu Arg Ser Leu Gln Thr
 1               5                  10                  15 ctg cga gac att gag cga ctg ctc cgc agc gga gag act gag ctc          96
Leu Arg Asp Ile Glu Arg Leu Leu Arg Ser Gly Glu Thr Glu Leu
             20                  25                  30 ttc ctc aag ggg ccc cca gga gga gcg ggt gag gga ggg cca cca gca     144
Phe Leu Lys Gly Pro Pro Gly Gly Ala Gly Glu Gly Gly Pro Pro Ala
         35                  40                  45 caa gcc ccc cct cca ccc cag cag caa ccc atg gcc cct ccc agt ggg     192
Gln Ala Pro Pro Pro Pro Gln Gln Gln Pro Met Ala Pro Pro Ser Gly
 50                  55                  60 ctg aaa aaa tat gag gac cct ttg cag tcc atg att tca cag aca cag     240
Leu Lys Lys Tyr Glu Asp Pro Leu Gln Ser Met Ile Ser Gln Thr Gln
 65                  70                  75                  80 agc cta ggg ggc ccc ccg ctg gag cat gaa gtg cct ggg cac ccc ccg     288
Ser Leu Gly Gly Pro Pro Leu Glu His Glu Val Pro Gly His Pro Pro
                 85                  90                  95 ggt ggg gac atg ggg cag cag atg aac atg atg ata cag agg ctg ggc     336
Gly Gly Asp Met Gly Gln Gln Met Asn Met Met Ile Gln Arg Leu Gly
             100                 105                 110 cag gac agc ctc acg cct gag cag gtg gcc tgg cgc aag ctg cag gag     384
Gln Asp Ser Leu Thr Pro Glu Gln Val Ala Trp Arg Lys Leu Gln Glu
         115                 120                 125 gag tac tac gaa gag aaa cgg cgg aaa gag gaa cag att ggg ctg cat     432
Glu Tyr Tyr Glu Glu Lys Arg Arg Lys Glu Glu Gln Ile Gly Leu His
130                 135                 140 ggg agc cgt cct ctg cag gac atg atg ggc atg ggg ggc atg atg gtg     480
Gly Ser Arg Pro Leu Gln Asp Met Met Gly Met Gly Gly Met Met Val
145                 150                 155                 160
```

```
agg ggg ccc ccg cct cct tac cac agc aag cct ggg gat cag tgg cca      528
Arg Gly Pro Pro Pro Pro Tyr His Ser Lys Pro Gly Asp Gln Trp Pro
            165                 170                 175 cct gga atg ggt gcg cag ctg cgg ggg ccc atg gat gtt caa gat ccc      576
Pro Gly Met Gly Ala Gln Leu Arg Gly Pro Met Asp Val Gln Asp Pro
        180                 185                 190 atg cag ctc cgg ggc gga cct ccc ttt cct ggg ccc cgt ttc cca ggc      624
Met Gln Leu Arg Gly Gly Pro Pro Phe Pro Gly Pro Arg Phe Pro Gly
    195                 200                 205 aac cag ata caa cgg gta cct ggg ttt ggg ggc atg cag agt atg ccc      672
Asn Gln Ile Gln Arg Val Pro Gly Phe Gly Gly Met Gln Ser Met Pro
210                 215                 220 atg gag gtg ccc atg aat gcc atg cag agg ccc gtg aga cca ggc atg      720
Met Glu Val Pro Met Asn Ala Met Gln Arg Pro Val Arg Pro Gly Met
225                 230                 235                 240 ggc tgg acc gaa gac ttg ccc cct atg ggg gga ccc agc aat ttt gcc      768
Gly Trp Thr Glu Asp Leu Pro Pro Met Gly Gly Pro Ser Asn Phe Ala
            245                 250                 255 cag aac acc atg ccc tac cca ggt ggg cag ggt gag gcg gag cga ttc      816
Gln Asn Thr Met Pro Tyr Pro Gly Gly Gln Gly Glu Ala Glu Arg Phe
        260                 265                 270 atg act ccc cgg gtc cgt gag gag ctg ctg cgg cac cag ctg ctg gag      864
Met Thr Pro Arg Val Arg Glu Glu Leu Leu Arg His Gln Leu Leu Glu
    275                 280                 285 aag cgg tcg atg ggc atg cag cgc ccc ctg ggc atg gca ggc agt ggc      912
Lys Arg Ser Met Gly Met Gln Arg Pro Leu Gly Met Ala Gly Ser Gly
290                 295                 300 atg gga cag agc atg gag atg gag cgg atg atg cag gcg cac cga cag      960
Met Gly Gln Ser Met Glu Met Glu Arg Met Met Gln Ala His Arg Gln
305                 310                 315                 320 atg gat cct gcc atg ttt ccc ggg cag atg gct ggt ggt gag ggc ctg     1008
Met Asp Pro Ala Met Phe Pro Gly Gln Met Ala Gly Gly Glu Gly Leu
            325                 330                 335 gcg ggc act ccc atg ggc atg gag ttt ggt gga ggc cgg ggc ctc ctg     1056
Ala Gly Thr Pro Met Gly Met Glu Phe Gly Gly Gly Arg Gly Leu Leu
        340                 345                 350 agc cct ccc atg ggg cag tct ggg ctg agg gag gtg gac cca ccc atg     1104
Ser Pro Pro Met Gly Gln Ser Gly Leu Arg Glu Val Asp Pro Pro Met
    355                 360                 365 ggg cca ggc aac ctc aac atg aac atg aat gtc aac atg aac atg aac     1152
Gly Pro Gly Asn Leu Asn Met Asn Met Asn Val Asn Met Asn Met Asn
370                 375                 380 atg aac ctg aac gtg cag atg acc ccg cag cag cag atg ctg atg tcg     1200
Met Asn Leu Asn Val Gln Met Thr Pro Gln Gln Gln Met Leu Met Ser
385                 390                 395                 400 cag aag atg cgg ggc cct ggg gac ttg atg ggg ccc cag ggc ctc agt     1248
Gln Lys Met Arg Gly Pro Gly Asp Leu Met Gly Pro Gln Gly Leu Ser
            405                 410                 415 cct gag gag atg gcc cgg gtt cgg gcc cag aac agc agt ggc gtg atg     1296
Pro Glu Glu Met Ala Arg Val Arg Ala Gln Asn Ser Ser Gly Val Met
        420                 425                 430 ggc ggc ccg cag aag atg ctg atg cct tca cag ttt ccc aac cag ggc     1344
Gly Gly Pro Gln Lys Met Leu Met Pro Ser Gln Phe Pro Asn Gln Gly
    435                 440                 445 cag cag gga ttc tct gga ggc cag gga ccc tac caa gcc atg tcc cag     1392
Gln Gln Gly Phe Ser Gly Gly Gln Gly Pro Tyr Gln Ala Met Ser Gln
450                 455                 460 gac atg ggc aat acc caa gac atg ttc agc cct gat cag agc tca atg     1440
Asp Met Gly Asn Thr Gln Asp Met Phe Ser Pro Asp Gln Ser Ser Met
```

|  |  |  |  |  |  |  |  |  |  |  |  |  |  |  |
|---|---|---|---|---|---|---|---|---|---|---|---|---|---|---|
| 465 |  |  |  |  | 470 |  |  |  |  | 475 |  |  |  | 480 |

```
ccc atg agc aac gtg ggc acc acc cgg ctc agc cac atg cct ctg ccc       1488
Pro Met Ser Asn Val Gly Thr Thr Arg Leu Ser His Met Pro Leu Pro
                485                 490                 495 cct gcg tcc aat cct cct ggg acc gtg cat tca gcc cca aac cgg ggg       1536
Pro Ala Ser Asn Pro Pro Gly Thr Val His Ser Ala Pro Asn Arg Gly
            500                 505                 510 cta ggc agg cgg cct tcg gac ctc acc atc agt att aat cag atg ggc       1584
Leu Gly Arg Arg Pro Ser Asp Leu Thr Ile Ser Ile Asn Gln Met Gly
        515                 520                 525 tca ccg ggc atg ggg cac ttg aag tcg ccc acc ctt agc cag gtg cac       1632
Ser Pro Gly Met Gly His Leu Lys Ser Pro Thr Leu Ser Gln Val His
    530                 535                 540 tca ccc ctg gtc acc tcg ccc tct gcc aac ctc aag tca ccc cag act       1680
Ser Pro Leu Val Thr Ser Pro Ser Ala Asn Leu Lys Ser Pro Gln Thr
545                 550                 555                 560 ccc tca cag atg gtg ccc ttg cct tct gcc aac ccg cca gga cct ctc       1728
Pro Ser Gln Met Val Pro Leu Pro Ser Ala Asn Pro Pro Gly Pro Leu
                565                 570                 575 aag tcg ccc cag gtc ctc ggc tcc tcc ctc agt gtc cgt tca ccc act       1776
Lys Ser Pro Gln Val Leu Gly Ser Ser Leu Ser Val Arg Ser Pro Thr
            580                 585                 590 ggc tcg ccc agc agg ctc aag tct cct tcc atg gcg gtg cct tct cca       1824
Gly Ser Pro Ser Arg Leu Lys Ser Pro Ser Met Ala Val Pro Ser Pro
        595                 600                 605 ggc tgg gtt gcc tca cct aag acg gcc atg ccc agc ccg ggg gtc tcc       1872
Gly Trp Val Ala Ser Pro Lys Thr Ala Met Pro Ser Pro Gly Val Ser
    610                 615                 620 cag aac aag cag ccg cct ctc aac atg aac tct tcc acc acc ctg agc       1920
Gln Asn Lys Gln Pro Pro Leu Asn Met Asn Ser Ser Thr Thr Leu Ser
625                 630                 635                 640 aac atg gaa cag ggt acc ctc ccg cct agc ggc ccc cgg agc agc tcc       1968
Asn Met Glu Gln Gly Thr Leu Pro Pro Ser Gly Pro Arg Ser Ser Ser
                645                 650                 655 tca gca cct ccc gcc aac cct ccc agc ggc ctc atg aac ccc agc cta       2016
Ser Ala Pro Pro Ala Asn Pro Pro Ser Gly Leu Met Asn Pro Ser Leu
            660                 665                 670 cca ttc act tcc tcc cca gac ccc aca cct tcc cag aac ccc ctg tca       2064
Pro Phe Thr Ser Ser Pro Asp Pro Thr Pro Ser Gln Asn Pro Leu Ser
        675                 680                 685 ctg atg atg acc cag atg tcc aag tac gcc atg ccc agc tcc acc ccg       2112
Leu Met Met Thr Gln Met Ser Lys Tyr Ala Met Pro Ser Ser Thr Pro
    690                 695                 700 ctc tac cac aat gcc atc aag acc atc gcc acc tca gac gac gag ctg       2160
Leu Tyr His Asn Ala Ile Lys Thr Ile Ala Thr Ser Asp Asp Glu Leu
705                 710                 715                 720 ctg ccc gac cgg ccc ctg ctg ccc ccc cca cca ccg cag ggc tcc          2208
Leu Pro Asp Arg Pro Leu Leu Pro Pro Pro Pro Pro Gln Gly Ser
                725                 730                 735 ggg cca g                                                            2215
Gly Pro <210> SEQ ID NO 12
<211> LENGTH: 738
<212> TYPE: PRT
<213> ORGANISM: Homo sapiens

<400> SEQUENCE: 12

Gly Leu Ser Lys Glu Gln Leu Glu His Arg Glu Arg Ser Leu Gln Thr
1               5                   10                  15
```

-continued

```
Leu Arg Asp Ile Glu Arg Leu Leu Arg Ser Gly Glu Thr Glu Leu
             20                  25                  30
Phe Leu Lys Gly Pro Pro Gly Ala Gly Glu Gly Pro Pro Ala
         35                  40                  45
Gln Ala Pro Pro Pro Gln Gln Pro Met Ala Pro Pro Ser Gly
     50                  55                  60
Leu Lys Lys Tyr Glu Asp Pro Leu Gln Ser Met Ile Ser Gln Thr Gln
 65                  70                  75                  80
Ser Leu Gly Gly Pro Leu Glu His Glu Val Pro Gly His Pro Pro
             85                  90                  95
Gly Gly Asp Met Gly Gln Gln Met Asn Met Met Ile Gln Arg Leu Gly
                100                 105                 110
Gln Asp Ser Leu Thr Pro Glu Gln Val Ala Trp Arg Lys Leu Gln Glu
        115                 120                 125
Glu Tyr Tyr Glu Glu Lys Arg Arg Lys Glu Gln Ile Gly Leu His
    130                 135                 140
Gly Ser Arg Pro Leu Gln Asp Met Met Gly Met Gly Gly Met Met Val
145                 150                 155                 160
Arg Gly Pro Pro Pro Tyr His Ser Lys Pro Gly Asp Gln Trp Pro
                165                 170                 175
Pro Gly Met Gly Ala Gln Leu Arg Gly Pro Met Asp Val Gln Asp Pro
            180                 185                 190
Met Gln Leu Arg Gly Gly Pro Pro Phe Pro Gly Pro Arg Phe Pro Gly
        195                 200                 205
Asn Gln Ile Gln Arg Val Pro Gly Phe Gly Gly Met Gln Ser Met Pro
    210                 215                 220
Met Glu Val Pro Met Asn Ala Met Gln Arg Pro Val Arg Pro Gly Met
225                 230                 235                 240
Gly Trp Thr Glu Asp Leu Pro Pro Met Gly Gly Pro Ser Asn Phe Ala
                245                 250                 255
Gln Asn Thr Met Pro Tyr Pro Gly Gly Gln Gly Glu Ala Glu Arg Phe
            260                 265                 270
Met Thr Pro Arg Val Arg Glu Glu Leu Leu Arg His Gln Leu Leu Glu
        275                 280                 285
Lys Arg Ser Met Gly Met Gln Arg Pro Leu Gly Met Ala Gly Ser Gly
    290                 295                 300
Met Gly Gln Ser Met Glu Met Glu Arg Met Met Gln Ala His Arg Gln
305                 310                 315                 320
Met Asp Pro Ala Met Phe Pro Gly Gln Met Ala Gly Gly Glu Gly Leu
                325                 330                 335
Ala Gly Thr Pro Met Gly Met Glu Phe Gly Gly Arg Gly Leu Leu
            340                 345                 350
Ser Pro Pro Met Gly Gln Ser Gly Leu Arg Glu Val Asp Pro Pro Met
        355                 360                 365
Gly Pro Gly Asn Leu Asn Met Asn Met Asn Val Asn Met Asn Met Asn
    370                 375                 380
Met Asn Leu Asn Val Gln Met Thr Pro Gln Gln Met Leu Met Ser
385                 390                 395                 400
Gln Lys Met Arg Gly Pro Gly Asp Leu Met Gly Pro Gln Gly Leu Ser
                405                 410                 415
Pro Glu Glu Met Ala Arg Val Arg Ala Gln Asn Ser Ser Gly Val Met
            420                 425                 430
```

```
Gly Gly Pro Gln Lys Met Leu Met Pro Ser Gln Phe Pro Asn Gln Gly
        435                 440                 445

Gln Gln Gly Phe Ser Gly Gly Gln Gly Pro Tyr Gln Ala Met Ser Gln
    450                 455                 460

Asp Met Gly Asn Thr Gln Asp Met Phe Ser Pro Asp Gln Ser Ser Met
465                 470                 475                 480

Pro Met Ser Asn Val Gly Thr Thr Arg Leu Ser His Met Pro Leu Pro
                485                 490                 495

Pro Ala Ser Asn Pro Pro Gly Thr Val His Ser Ala Pro Asn Arg Gly
                500                 505                 510

Leu Gly Arg Arg Pro Ser Asp Leu Thr Ile Ser Ile Asn Gln Met Gly
            515                 520                 525

Ser Pro Gly Met Gly His Leu Lys Ser Pro Thr Leu Ser Gln Val His
530                 535                 540

Ser Pro Leu Val Thr Ser Pro Ser Ala Asn Leu Lys Ser Pro Gln Thr
545                 550                 555                 560

Pro Ser Gln Met Val Pro Leu Pro Ser Ala Asn Pro Pro Gly Pro Leu
                565                 570                 575

Lys Ser Pro Gln Val Leu Gly Ser Ser Leu Ser Val Arg Ser Pro Thr
            580                 585                 590

Gly Ser Pro Ser Arg Leu Lys Ser Pro Ser Met Ala Val Pro Ser Pro
        595                 600                 605

Gly Trp Val Ala Ser Pro Lys Thr Ala Met Pro Ser Pro Gly Val Ser
    610                 615                 620

Gln Asn Lys Gln Pro Pro Leu Asn Met Asn Ser Ser Thr Thr Leu Ser
625                 630                 635                 640

Asn Met Glu Gln Gly Thr Leu Pro Pro Ser Gly Pro Arg Ser Ser Ser
                645                 650                 655

Ser Ala Pro Pro Ala Asn Pro Pro Ser Gly Leu Met Asn Pro Ser Leu
                660                 665                 670

Pro Phe Thr Ser Ser Pro Asp Pro Thr Pro Ser Gln Asn Pro Leu Ser
            675                 680                 685

Leu Met Met Thr Gln Met Ser Lys Tyr Ala Met Pro Ser Ser Thr Pro
        690                 695                 700

Leu Tyr His Asn Ala Ile Lys Thr Ile Ala Thr Ser Asp Asp Glu Leu
705                 710                 715                 720

Leu Pro Asp Arg Pro Leu Leu Pro Pro Pro Pro Pro Gln Gly Ser
                725                 730                 735

Gly Pro
```

<210> SEQ ID NO 13
<211> LENGTH: 28
<212> TYPE: DNA
<213> ORGANISM: Artificial Sequence
<220> FEATURE:
<223> OTHER INFORMATION: sense primer for armadillo repeat 1 (downstream
      of Asn141)
      of mouse beta-catenin comprising the MunI recognition site
      at the 5'-terminus

<400> SEQUENCE: 13
ggccaattga actatcagga tgacgcgg                                          28

<210> SEQ ID NO 14
<211> LENGTH: 29
<212> TYPE: DNA
<213> ORGANISM: Artificial Sequence

```
<220> FEATURE:
<223> OTHER INFORMATION: antisense primer for armadillo repeat 6
      (upstream of Asp390)
      of mouse beta-catenin comprising the SalI recognition site
      at the 5'-terminus

<400> SEQUENCE: 14
ggcgtcgaca tctgaaaggt ttctgagag                                         29

<210> SEQ ID NO 15
<211> LENGTH: 28
<212> TYPE: DNA
<213> ORGANISM: Artificial Sequence
<220> FEATURE:
<223> OTHER INFORMATION: sense primer for armadillo repeat 7 (downstream
      of Ala391)
      of mouse beta-catenin comprising the MunI recognition site
      at the 5'-terminus

<400> SEQUENCE: 15
ggccaattga actatcagga tgacgcgg                                          28

<210> SEQ ID NO 16
<211> LENGTH: 30
<212> TYPE: DNA
<213> ORGANISM: Artificial Sequence
<220> FEATURE:
<223> OTHER INFORMATION: antisense primer for armadillo repeat 12
      (upstream of Glu664)
      of mouse beta-catenin comprising the SalI recognition site
      at the 5'-terminus

<400> SEQUENCE: 16
ggcgtcgacc tcagacattc ggaataggac                                        30

<210> SEQ ID NO 17
<211> LENGTH: 1450
<212> TYPE: PRT
<213> ORGANISM: Mus musculus

<400> SEQUENCE: 17

Met Arg Ile Leu Ala Asn Lys Thr Arg Leu Pro His Pro Arg Arg Arg
 1               5                  10                  15

Glu Ala Pro Gly Ser Pro Pro Leu Ser Pro Arg Gly His Cys Pro Pro
            20                  25                  30

Ala Pro Ala Lys Pro Met His Pro Glu Asn Lys Leu Thr Asn His Gly
        35                  40                  45

Lys Thr Gly Asn Gly Gly Ala Gln Ser Gln His Gln Asn Val Asn Gln
    50                  55                  60

Gly Pro Thr Cys Asn Leu Gly Ser Lys Gly Val Gly Ala Gly Ser His
65                  70                  75                  80

Gly Ala Lys Ala Asn Gln Ile Ser Pro Ser Asn Ser Ser Leu Lys Asn
                85                  90                  95

Pro Gln Ala Gly Val Ser Pro Phe Ser Ser Leu Lys Gly Lys Val Lys
            100                 105                 110

Arg Glu Arg Ser Val Ser Val Asp Ser Gly Glu Gln Arg Glu Ala Gly
        115                 120                 125

Thr Pro Ser Leu Asp Ser Glu Ala Lys Glu Val Ala Pro Arg Ser Lys
    130                 135                 140

Arg Arg Cys Val Leu Glu Arg Lys Gln Pro Tyr Ser Gly Asp Glu Trp
145                 150                 155                 160

Cys Ser Gly Pro Asp Ser Glu Glu Asp Asp Lys Pro Ile Ala Ala Ala
```

-continued

```
                165                 170                 175
His Asn Cys Asn Val Ala Asp Pro Ala Met Val Thr Pro Gln Leu Gly
            180                 185                 190
Pro Gly Gln Thr Ala Gln Leu Pro Leu Ser Glu Ser Ser Ala Pro Gly
            195                 200                 205
Pro Gln His Gly Pro Gln Pro Gly Leu Arg Pro Asp Val Pro Gly Gly
            210                 215                 220
Gly Gly Gly Gly Val Pro Gly Lys Pro Ser Gln Phe Val Tyr Val
225                 230                 235                 240
Phe Thr Thr His Leu Ala Asn Thr Ala Ala Glu Ala Val Leu Gln Gly
                245                 250                 255
Arg Ala Glu Ser Ile Leu Ala Tyr His Gln Gln Asn Val Pro Arg Ala
                260                 265                 270
Lys Leu Asp Gln Ala Pro Lys Val Pro Pro Thr Pro Glu Pro Leu Pro
            275                 280                 285
Leu Asn Thr Pro Ser Ala Gly Thr Pro Gln Ser Gln Pro Pro Pro Leu
            290                 295                 300
Pro Pro Pro Pro Ala Pro Gly Ser Ala Pro Pro Ala Leu Pro Pro
305                 310                 315                 320
Glu Gly Pro Pro Glu Asp Thr Ser Gln Asp Leu Ala Pro Asn Ser Val
                325                 330                 335
Gly Ala Ala Ser Thr Gly Gly Thr Gly Gly Thr His Pro Asn Thr
            340                 345                 350
Pro Thr Ala Ala Thr Ala Asn Asn Pro Leu Pro Pro Gly Gly Asp Pro
            355                 360                 365
Gly Ser Ala Pro Gly Ser Ala Leu Leu Gly Glu Ala Thr Pro Thr Gly
370                 375                 380
Asn Gly Gln Arg Asn Leu Val Gly Ser Glu Gly Leu Ser Lys Glu Gln
385                 390                 395                 400
Leu Glu His Arg Glu Arg Ser Leu Gln Thr Leu Arg Asp Ile Glu Arg
                405                 410                 415
Leu Leu Leu Arg Ser Gly Glu Thr Glu Pro Phe Leu Lys Gly Pro Pro
                420                 425                 430
Gly Gly Ala Gly Glu Gly Gly Pro Ala Gln Ala Pro Ser Ala Ala
            435                 440                 445
Gln Pro Pro Pro Ser Ala Pro Pro Gly Gly Leu Lys Lys Tyr Glu Glu
            450                 455                 460
Pro Leu Gln Ser Met Ile Ser Gln Thr Gln Ser Leu Gly Gly Pro Pro
465                 470                 475                 480
Leu Glu His Glu Val Pro Gly His Pro Gln Gly Gly Asp Met Gly Gln
                485                 490                 495
Gln Met Asn Met Met Gln Arg Leu Gly Gln Asp Ser Leu Thr Pro
            500                 505                 510
Glu Gln Val Ala Trp Arg Lys Leu Gln Glu Glu Tyr Tyr Glu Glu Lys
            515                 520                 525
Arg Arg Lys Glu Glu Gln Ile Gly Leu His Gly Arg Pro Leu Gln
            530                 535                 540
Asp Met Val Gly Met Gly Gly Met Gly Arg Gly Pro Pro Pro
545                 550                 555                 560
Tyr His Ser Lys Pro Gly Asp Gln Cys Ala Pro Gly Met Gly Ala Gln
                565                 570                 575
Leu Arg Gly Pro Met Asp Val Gln Asp Pro Met Gln Leu Arg Pro Gly
                580                 585                 590
```

-continued

```
Pro Pro Phe Pro Gly Pro Arg Phe Pro Gly Asn Gln Met Gln Arg Val
            595                 600                 605
Pro Gly Phe Gly Gly Met Gln Ser Met Pro Met Glu Val Pro Met Asn
        610                 615                 620
Ala Met Gln Arg Pro Val Arg Pro Gly Met Ala Trp Asn Glu Asp Leu
625                 630                 635                 640
Pro Pro Ile Gly Gly Pro Ser Asn Phe Ala Gln Asn Ala Val Pro Tyr
                645                 650                 655
Pro Gly Gly Gln Gly Glu Ala Glu Arg Phe Met Thr Pro Arg Val Arg
            660                 665                 670
Glu Glu Leu Leu Arg His Gln Leu Leu Glu Lys Arg Ser Met Gly Met
        675                 680                 685
Gln Arg Pro Leu Gly Met Ala Gly Ser Gly Met Gly Gln Ser Met Glu
690                 695                 700
Met Glu Arg Met Ile Gln Ala His Arg Gln Met Asp Pro Ala Met Phe
705                 710                 715                 720
Pro Gly Gln Met Thr Gly Gly Asp Gly Leu Ala Gly Thr Pro Met Gly
                725                 730                 735
Ile Glu Phe Gly Gly Gly Arg Gly Leu Leu Ser Pro Pro Met Gly Gln
            740                 745                 750
Ser Gly Leu Arg Glu Val Asp Pro Pro Met Gly Pro Gly Asn Leu Asn
        755                 760                 765
Met Asn Met Asn Val Asn Met Asn Met Asn Met Asn Leu Asn Val Gln
770                 775                 780
Met Thr Pro Gln Gln Met Leu Met Ser Gln Lys Met Arg Gly Pro
785                 790                 795                 800
Gly Asp Met Met Gly Pro Gln Gly Leu Ser Pro Glu Glu Met Ala Arg
                805                 810                 815
Val Arg Ala Gln Asn Ser Ser Gly Met Met Gly Gly Pro Gln Lys Met
            820                 825                 830
Leu Met Pro Ser Gln Phe Pro Asn Gln Gly Gln Gln Gly Phe Ser Gly
        835                 840                 845
Gly Gln Gly Pro Tyr Gln Ala Met Pro Gln Asp Met Gly Asn Thr Pro
850                 855                 860
Asp Met Phe Ser Pro Asp Gln Ser Ser Val Pro Met Gly Thr Val Gly
865                 870                 875                 880
Thr Ala Arg Leu Ser His Met Pro Leu Pro Pro Ala Ser Asn Pro Pro
                885                 890                 895
Gly Ser Val His Leu Ala Ser Asn Arg Gly Leu Gly Arg Arg Pro Ser
            900                 905                 910
Asp Leu Thr Ile Ser Ile Asn Gln Met Gly Ser Pro Gly Met Gly His
        915                 920                 925
Leu Lys Ser Pro Thr Leu Ser Gln Val His Ser Pro Leu Val Thr Ser
        930                 935                 940
Pro Ser Ala Asn Leu Lys Ser Pro Gln Thr Pro Ser Gln Met Val Pro
945                 950                 955                 960
Leu Pro Ser Thr Asn Pro Pro Gly Pro Leu Lys Ser Pro Gln Val Leu
                965                 970                 975
Ser Ser Ser Leu Gly Val Arg Ser Pro Thr Gly Ser Pro Ser Arg Leu
            980                 985                 990
Lys Ser Pro Ser Met Ala Val Pro Ser Pro Gly Trp Val Ala Ser Pro
        995                 1000                1005
```

```
Lys Thr Ala Met Pro Ser Pro Gly Val Ser Gln Asn Lys Gln Pro Pro
    1010                1015                1020

Leu Ser Ile Asn Ser Ser Ser Thr Leu Gly Asn Val Glu Gln Gly Ala
1025                1030                1035                1040

Leu Pro Pro Ser Ala Pro Arg Asn Ser Ser Ala Pro Pro Ala Asn
                1045                1050                1055

Pro Ser Ser Gly Leu Met Asn Pro Ser Leu Pro Phe Thr Ser Ser Pro
                1060                1065                1070

Asp Pro Thr Pro Ser Gln Asn Pro Leu Ser Leu Met Met Ser Gln Met
            1075                1080                1085

Ser Lys Tyr Ala Met Pro Ser Ser Thr Pro Leu Tyr His Asn Ala Ile
    1090                1095                1100

Lys Thr Ile Ala Thr Ser Asp Asp Glu Leu Leu Pro Asp Arg Pro Leu
1105                1110                1115                1120

Leu Pro Pro Pro Pro Pro Gln Gly Ser Gly Pro Gly Ile Ser Asn
                1125                1130                1135

Asn Gln Pro Asn Gln Met His Met Asn Pro Ala Ala Ala Gln Ser Pro
                1140                1145                1150

Met Gly Met Asn Leu Pro Gly Gln Gln Pro Leu Ser His Glu Pro Pro
            1155                1160                1165

Pro Thr Met Leu Pro Ser Pro Thr Pro Leu Gly Ser Asn Ile Pro Leu
            1170                1175                1180

His Pro Asn Ala Gln Gly Thr Gly Gly Ser Ser Gln Asn Ser Met Met
1185                1190                1195                1200

Met Ala Pro Gly Gly Pro Asp Ser Leu Asn Ala Pro Cys Gly Pro Val
                1205                1210                1215

Pro Ser Ser Ser Gln Met Met Ser Phe Pro Pro Arg Leu Gln Gln Pro
                1220                1225                1230

His Gly Ala Met Ala Pro Thr Gly Ala Gly Gly Pro Gly Leu Gln Gln
            1235                1240                1245

His Tyr Pro Ser Gly Met Ala Leu Pro Pro Glu Asp Leu Pro Thr Gln
    1250                1255                1260

Pro Pro Gly Pro Ile Pro Pro Gln Gln His Leu Met Gly Lys Gly Met
1265                1270                1275                1280

Thr Gly Arg Met Gly Asp Ala Tyr Pro Pro Gly Val Leu Pro Gly Val
                1285                1290                1295

Ala Ser Val Leu Asn Asp Pro Glu Leu Ser Glu Val Ile Arg Pro Thr
            1300                1305                1310

Pro Thr Gly Ile Pro Glu Phe Asp Leu Ser Arg Ile Ile Pro Ser Glu
            1315                1320                1325

Lys Pro Ser Ser Thr Leu Gln Tyr Phe Pro Lys Ser Glu Asn Gln Pro
    1330                1335                1340

Pro Lys Ala Gln Pro Pro Asn Leu His Leu Met Asn Leu Gln Asn Met
1345                1350                1355                1360

Met Ala Glu Gln Thr Pro Ser Arg Pro Pro Asn Leu Pro Gly Gln Gln
                1365                1370                1375

Gly Val Gln Arg Gly Leu Ser Met Ser Met Cys His Pro Gly Gln Met
            1380                1385                1390

Ser Leu Leu Gly Arg Thr Gly Val Pro Pro Gln Gln Gly Met Val Pro
            1395                1400                1405

His Gly Leu His Gln Gly Val Met Ser Pro Pro Gln Gly Leu Met Thr
    1410                1415                1420

Gln Gln Asn Phe Met Leu Met Lys Gln Arg Gly Val Gly Gly Glu Val
```

```
                       1425              1430              1435              1440

Tyr Thr Gln Pro Pro His Met Leu Ser Pro
                    1445              1450

<210> SEQ ID NO 18
<211> LENGTH: 1394
<212> TYPE: PRT
<213> ORGANISM: Homo sapiens

<400> SEQUENCE: 18

Met His Ser Ser Asn Pro Lys Val Arg Ser Pro Ser Gly Asn Thr
 1               5                  10                  15

Gln Ser Ser Pro Lys Ser Lys Gln Glu Val Met Val Arg Pro Pro Thr
                20                  25                  30

Val Met Ser Pro Ser Gly Asn Pro Gln Leu Asp Ser Lys Phe Ser Asn
            35                  40                  45

Gln Gly Lys Gln Gly Gly Ser Ala Ser Gln Ser Gln Pro Ser Pro Cys
         50                  55                  60

Asp Ser Lys Ser Gly Gly His Thr Pro Lys Ala Leu Pro Gly Pro Gly
 65                  70                  75                  80

Gly Ser Met Gly Leu Lys Asn Gly Ala Gly Asn Gly Ala Lys Gly Lys
                 85                  90                  95

Gly Lys Arg Glu Arg Ser Ile Ser Ala Asp Ser Phe Asp Gln Arg Asp
                100                 105                 110

Pro Gly Thr Pro Asn Asp Asp Ser Asp Ile Lys Glu Cys Asn Ser Ala
            115                 120                 125

Asp His Ile Lys Ser Gln Asp Ser Gln His Thr Pro His Ser Met Thr
130                 135                 140

Pro Ser Asn Ala Thr Ala Pro Arg Ser Ser Thr Pro Ser His Gly Gln
145                 150                 155                 160

Thr Thr Ala Thr Glu Pro Thr Pro Ala Gln Lys Thr Pro Ala Lys Val
                165                 170                 175

Val Tyr Val Phe Ser Thr Glu Met Ala Asn Lys Ala Ala Glu Ala Val
            180                 185                 190

Leu Lys Gly Gln Val Glu Thr Ile Val Ser Phe His Ile Gln Asn Ile
        195                 200                 205

Ser Asn Asn Lys Thr Glu Arg Ser Thr Ala Pro Leu Asn Thr Gln Ile
    210                 215                 220

Ser Ala Leu Arg Asn Asp Pro Lys Pro Leu Pro Gln Gln Pro Pro Val
225                 230                 235                 240

Pro Ala Asn Gln Asp Gln Asn Ser Ser Gln Asn Thr Arg Leu Gln Pro
                245                 250                 255

Thr Pro Pro Ile Pro Ala Pro Ala Pro Lys Pro Ala Ala Pro Pro Arg
            260                 265                 270

Pro Leu Asp Arg Glu Ser Pro Gly Val Glu Asn Lys Leu Ile Pro Ser
        275                 280                 285

Val Gly Ser Pro Ala Ser Ser Thr Pro Leu Pro Asp Gly Thr Gly
    290                 295                 300

Pro Asn Ser Thr Pro Asn Asn Arg Ala Val Thr Pro Val Ser Gln Gly
305                 310                 315                 320

Ser Asn Ser Ser Ser Ala Asp Pro Lys Ala Pro Pro Pro Pro Val
                325                 330                 335

Ser Ser Gly Glu Pro Pro Thr Leu Gly Glu Asn Pro Asp Gly Leu Ser
            340                 345                 350
```

```
Gln Glu Gln Leu Glu His Arg Glu Arg Ser Leu Gln Thr Leu Arg Asp
            355                 360                 365

Ile Gln Arg Met Leu Phe Pro Asp Glu Lys Glu Phe Thr Gly Ala Gln
    370                 375                 380

Ser Gly Gly Pro Gln Gln Asn Pro Gly Val Leu Asp Gly Pro Gln Lys
385                 390                 395                 400

Lys Pro Glu Gly Pro Ile Gln Ala Met Met Ala Gln Ser Gln Ser Leu
                405                 410                 415

Gly Lys Gly Pro Gly Pro Arg Thr Asp Val Gly Ala Pro Phe Gly Pro
            420                 425                 430

Gln Gly His Arg Asp Val Pro Phe Ser Pro Asp Glu Met Val Pro Pro
            435                 440                 445

Ser Met Asn Ser Gln Ser Gly Thr Ile Gly Pro Asp His Leu Asp His
    450                 455                 460

Met Thr Pro Glu Gln Ile Ala Trp Leu Lys Leu Gln Gln Glu Phe Tyr
465                 470                 475                 480

Glu Glu Lys Arg Arg Lys Pro Glu Gln Val Val Gln Gln Cys Ser
                485                 490                 495

Leu Gln Asp Met Met Val His Gln His Gly Pro Arg Gly Val Val Arg
            500                 505                 510

Gly Pro Pro Pro Pro Tyr Gln Met Thr Pro Ser Glu Gly Trp Ala Pro
            515                 520                 525

Gly Gly Thr Glu Pro Phe Ser Asp Gly Ile Asn Met Pro His Ser Leu
            530                 535                 540

Pro Pro Arg Gly Met Ala Pro His Pro Asn Met Pro Gly Ser Gln Met
545                 550                 555                 560

Arg Leu Pro Gly Phe Ala Gly Met Ile Asn Ser Glu Met Glu Gly Pro
                565                 570                 575

Asn Val Pro Asn Pro Ala Ser Arg Pro Gly Leu Ser Gly Val Ser Trp
            580                 585                 590

Pro Asp Asp Val Pro Lys Ile Pro Asp Gly Arg Asn Phe Pro Pro Gly
            595                 600                 605

Arg Gly Ile Phe Ser Gly Pro Gly Arg Gly Glu Arg Phe Pro Asn Pro
            610                 615                 620

Gln Gly Leu Ser Glu Glu Met Phe Gln Gln Leu Ala Glu Lys Gln
625                 630                 635                 640

Leu Gly Leu Pro Pro Gly Met Ala Met Glu Gly Ile Arg Pro Ser Met
                645                 650                 655

Glu Met Asn Arg Met Ile Pro Gly Ser Gln Arg His Met Glu Pro Gly
            660                 665                 670

Asn Asn Pro Ile Phe Pro Arg Ile Pro Val Glu Gly Pro Leu Ser Pro
            675                 680                 685

Ser Arg Gly Asp Phe Pro Lys Gly Ile Pro Pro Gln Met Gly Pro Gly
    690                 695                 700

Arg Glu Leu Glu Phe Gly Met Val Pro Ser Gly Met Lys Gly Asp Val
705                 710                 715                 720

Asn Leu Asn Val Asn Met Gly Ser Asn Ser Gln Met Ile Pro Gln Lys
                725                 730                 735

Met Arg Glu Ala Gly Ala Gly Pro Glu Glu Met Leu Lys Leu Arg Pro
            740                 745                 750

Gly Gly Ser Asp Met Leu Pro Ala Gln Gln Lys Met Val Pro Leu Pro
            755                 760                 765

Phe Gly Glu His Pro Gln Gln Glu Tyr Gly Met Gly Pro Arg Pro Phe
```

```
                770             775             780
Leu Pro Met Ser Gln Gly Pro Gly Ser Asn Ser Gly Leu Arg Asn Leu
785                 790                 795                 800

Arg Glu Pro Ile Gly Pro Asp Gln Arg Thr Asn Ser Arg Leu Ser His
                805                 810                 815

Met Pro Pro Leu Pro Leu Asn Pro Ser Ser Asn Pro Thr Ser Leu Asn
                820                 825                 830

Thr Ala Pro Pro Val Gln Arg Gly Leu Gly Arg Lys Pro Leu Asp Leu
                835                 840                 845

Thr Ile Ser Gly Ser Gln Val His Ser Pro Gly Ile Asn Pro Leu Lys
850                 855                 860

Ser Pro Thr Met His Gln Val Gln Ser Pro Met Leu Gly Ser Pro Ser
865                 870                 875                 880

Gly Asn Leu Lys Ser Pro Gln Thr Pro Ser Gln Leu Ala Gly Met Leu
                885                 890                 895

Ala Gly Pro Ala Ala Ala Ala Ser Ile Lys Ser Pro Pro Val Leu Gly
                900                 905                 910

Ser Ala Ala Ser Pro Val His Leu Lys Ser Pro Ser Leu Pro Ala
                915                 920                 925

Pro Ser Pro Gly Trp Thr Ser Ser Pro Lys Pro Leu Gln Ser Pro
930                 935                 940

Gly Ile Pro Pro Asn His Lys Ala Pro Leu Thr Met Ala Ser Pro Ala
945                 950                 955                 960

Met Leu Gly Asn Val Glu Ser Gly Pro Pro Pro Thr Ala Ser
                965                 970                 975

Gln Pro Ala Ser Val Asn Ile Pro Gly Ser Leu Pro Ser Ser Thr Pro
                980                 985                 990

Tyr Thr Met Pro Pro Glu Pro Thr Leu Ser Gln Asn Pro Leu Ser Ile
                995                 1000                1005

Met Met Ser Arg Met Ser Lys Phe Ala Met Pro Ser Ser Thr Pro Leu
                1010                1015                1020

Tyr His Asp Ala Ile Lys Thr Val Ala Ser Ser Asp Asp Ser Pro
1025                1030                1035                1040

Pro Ala Arg Ser Pro Asn Leu Pro Ser Met Asn Asn Met Pro Gly Met
                1045                1050                1055

Gly Ile Asn Thr Gln Asn Pro Arg Ile Ser Gly Pro Asn Pro Val Val
                1060                1065                1070

Pro Met Pro Thr Leu Ser Pro Met Gly Met Thr Gln Pro Leu Ser His
                1075                1080                1085

Ser Asn Gln Met Pro Ser Pro Asn Ala Val Gly Pro Asn Ile Pro Pro
                1090                1095                1100

His Gly Val Pro Met Gly Pro Gly Leu Met Ser His Asn Pro Ile Met
1105                1110                1115                1120

Gly His Gly Ser Gln Glu Pro Pro Met Val Pro Gln Gly Arg Met Gly
                1125                1130                1135

Phe Pro Gln Gly Phe Pro Pro Val Gln Ser Pro Gln Gln Val Pro
                1140                1145                1150

Phe Pro His Asn Gly Pro Ser Gly Gln Gly Ser Phe Pro Gly Gly
                1155                1160                1165

Met Gly Phe Pro Gly Glu Gly Pro Leu Gly Arg Pro Ser Asn Leu Pro
                1170                1175                1180

Gln Ser Ser Ala Asp Ala Ala Leu Cys Lys Pro Gly Gly Pro Gly Gly
1185                1190                1195                1200
```

-continued

```
Pro Asp Ser Phe Thr Val Leu Gly Asn Ser Met Pro Ser Val Phe Thr
                1205                1210                1215

Asp Pro Asp Leu Gln Glu Val Ile Arg Pro Gly Ala Thr Gly Ile Pro
            1220                1225                1230

Glu Phe Asp Leu Ser Arg Ile Ile Pro Ser Glu Lys Pro Ser Gln Thr
            1235                1240                1245

Leu Gln Tyr Phe Pro Arg Gly Val Pro Gly Arg Lys Gln Pro Gln
        1250                1255                1260

Gly Pro Gly Pro Gly Phe Ser His Met Gln Gly Met Met Gly Glu Gln
1265                1270                1275                1280

Ala Pro Arg Met Gly Leu Ala Leu Pro Gly Met Gly Gly Pro Gly Pro
                1285                1290                1295

Val Gly Thr Pro Asp Ile Pro Leu Gly Thr Ala Pro Ser Met Pro Gly
            1300                1305                1310

His Asn Pro Met Arg Pro Pro Ala Phe Leu Gln Gln Gly Met Met Gly
            1315                1320                1325

Pro His His Arg Met Met Ser Pro Ala Gln Ser Thr Met Pro Gly Gln
        1330                1335                1340

Pro Thr Leu Met Ser Asn Pro Ala Ala Ala Val Gly Met Ile Pro Gly
1345                1350                1355                1360

Lys Asp Arg Gly Pro Ala Gly Leu Tyr Thr His Pro Gly Pro Val Gly
                1365                1370                1375

Ser Pro Gly Met Met Met Ser Met Gln Gly Met Met Gly Pro Asn Arg
            1380                1385                1390

Thr Ser
```